(12) United States Patent
Campbell et al.

(10) Patent No.: US 12,403,169 B2
(45) Date of Patent: Sep. 2, 2025

(54) **COMPOSITIONS AND METHODS RELATED TO *RHAMNUS PRINOIDES* (GESHO) EXTRACT FOR THE INHIBITION OF POLYMICROBIAL BIOFILM FORMATION**

(71) Applicant: GEORGIA STATE UNIVERSITY RESEARCH FOUNDATION, INC., Atlanta, GA (US)

(72) Inventors: Mariya Campbell, Suwanee, GA (US); Eric Gilbert, Decatur, GA (US)

(73) Assignee: GEORGIA STATE UNIVERSITY RESEARCH FOUNDATION, INC., Atlanta, GA (US)

( * ) Notice: Subject to any disclaimer, the term of this patent is extended or adjusted under 35 U.S.C. 154(b) by 0 days.

(21) Appl. No.: 18/345,643

(22) Filed: Jun. 30, 2023

(65) Prior Publication Data
US 2024/0041967 A1    Feb. 8, 2024

Related U.S. Application Data

(62) Division of application No. 17/053,496, filed as application No. PCT/US2019/031157 on May 7, 2019, now Pat. No. 11,717,551.

(60) Provisional application No. 62/667,910, filed on May 7, 2018.

(51) Int. Cl.
| | |
|---|---|
| A61K 36/72 | (2006.01) |
| A01N 31/02 | (2006.01) |
| A01N 35/02 | (2006.01) |
| A01N 37/10 | (2006.01) |
| A01N 65/08 | (2009.01) |
| A61K 31/045 | (2006.01) |
| A61K 31/121 | (2006.01) |
| A61K 31/235 | (2006.01) |
| A61L 2/00 | (2006.01) |
| A61L 2/18 | (2006.01) |
| A61L 15/20 | (2006.01) |
| A61L 15/40 | (2006.01) |
| A61P 31/04 | (2006.01) |
| C11D 3/48 | (2006.01) |
| A61L 101/34 | (2006.01) |
| A61L 101/36 | (2006.01) |
| A61L 101/38 | (2006.01) |

(52) U.S. Cl.
CPC ............. *A61K 36/72* (2013.01); *A01N 31/02* (2013.01); *A01N 35/02* (2013.01); *A01N 37/10* (2013.01); *A01N 65/08* (2013.01); *A61K 31/045* (2013.01); *A61K 31/121* (2013.01); *A61K 31/235* (2013.01); *A61L 2/0088* (2013.01); *A61L 2/18* (2013.01); *A61L 15/20* (2013.01); *A61L 15/40* (2013.01); *A61P 31/04* (2018.01); *C11D 3/48* (2013.01); *A61L 2101/34* (2020.08); *A61L 2101/36* (2020.08); *A61L 2101/38* (2020.08); *A61L 2202/24* (2013.01); *A61L 2300/404* (2013.01); *C11D 2111/14* (2024.01)

(58) Field of Classification Search
CPC ... A61K 8/416; A61K 2800/596; A61Q 19/10
See application file for complete search history.

(56) References Cited

U.S. PATENT DOCUMENTS

| | | | | |
|---|---|---|---|---|
| 6,054,504 | A | * | 4/2000 | Dalla Riva Toma .. A01N 25/10 524/537 |
| 2002/0137631 | A1 | * | 9/2002 | Falder ................... A01N 43/80 504/362 |
| 2009/0068247 | A1 | * | 3/2009 | Jay .......................... A61L 29/16 514/2.4 |

FOREIGN PATENT DOCUMENTS

| | | | | |
|---|---|---|---|---|
| CN | 106234439 | A | * 12/2016 | ............ A01N 33/12 |
| JP | H10 81607 | A | 3/1998 | |
| WO | 2017/214691 | A | 12/2017 | |

OTHER PUBLICATIONS

Machine translation of CN-106234439-A, pp. 1-8. (Year: 2016).*
Kaushik, J.J. et al. BJPR, 14(3): 1-9, 2016; Article No. BJPR.30059 (Year: 2016).*
Communication pursuant to Article 94(3) EPC in connection with EP Application 19 799 832.1, dated May 21, 2025.
Xu Zhi-Hong et al. "A New Bicoumarin from Stellera Chamaejasme L," Journal of Asian Natural Products Research. 7 pages.

* cited by examiner

*Primary Examiner* — Andrew S Rosenthal
(74) *Attorney, Agent, or Firm* — Meunier Carlin & Curfman LLC

(57) ABSTRACT

Disclosed are compositions comprising *Rhamnus prinoides* (GESHO) extract or fragments thereof and methods of using Gesho extract for the inhibition of biofilm formation.

23 Claims, 27 Drawing Sheets

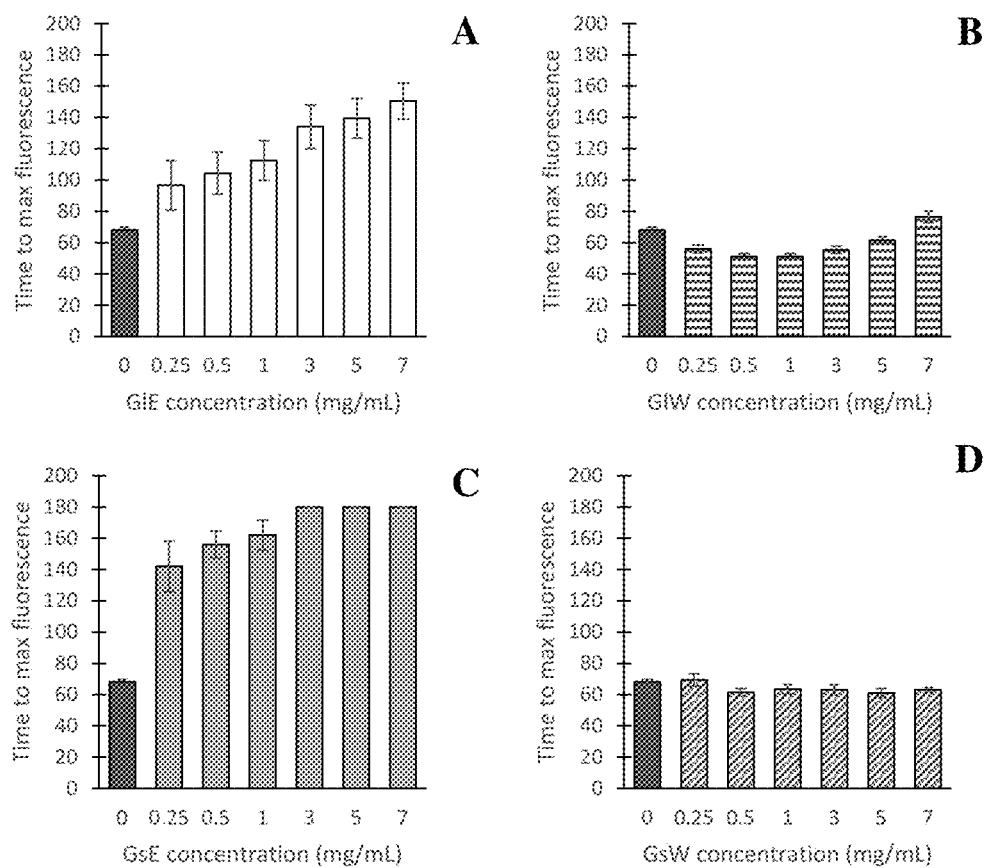
FIG. 11A, FIG. 11B, FIG. 11C, and FIG. 11D

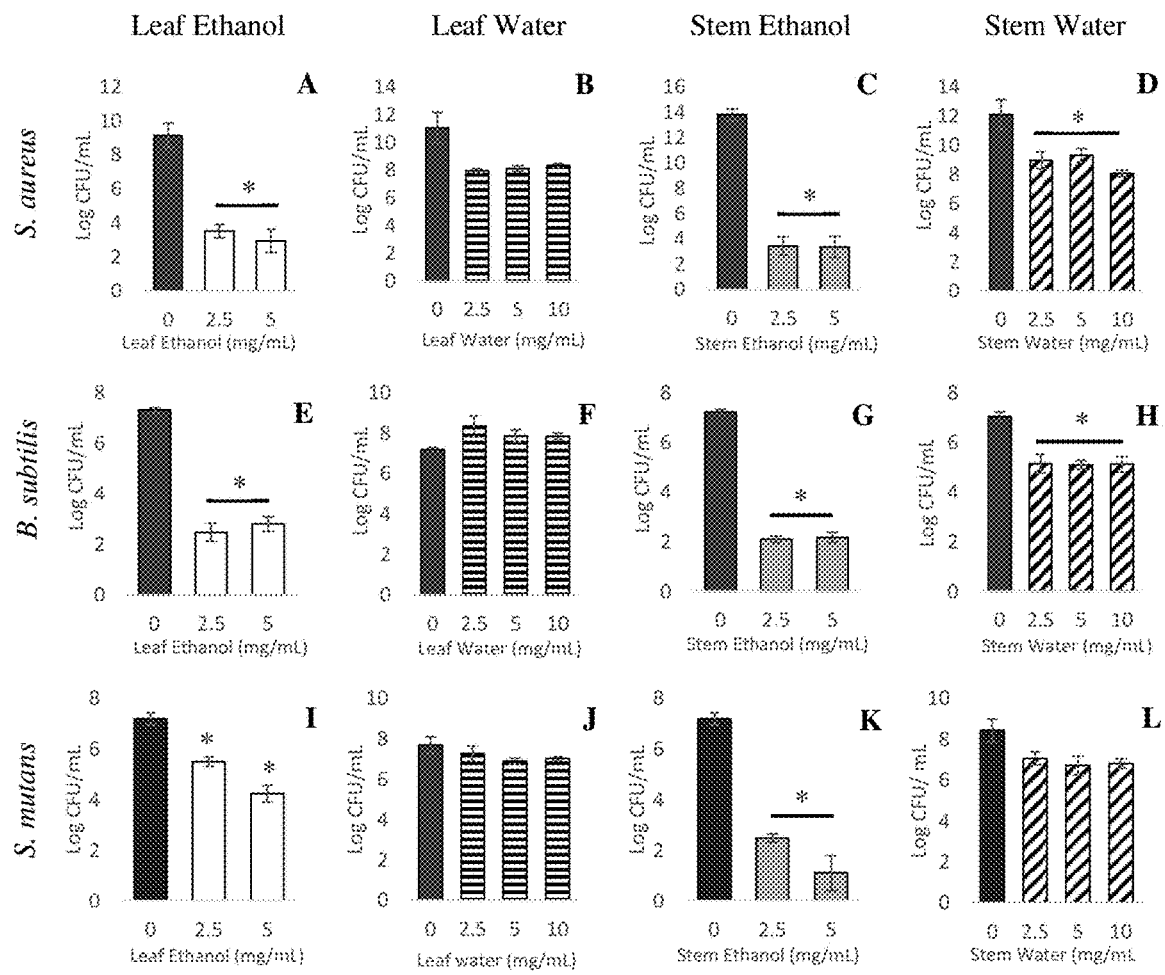
FIG. 13A, FIG. 13B, FIG. 13C, FIG. 13D, FIG. 13E, FIG. 13F, FIG. 13G, FIG. 13H, FIG. 13I, FIG. 13J, FIG. 13K, and FIG. 13L

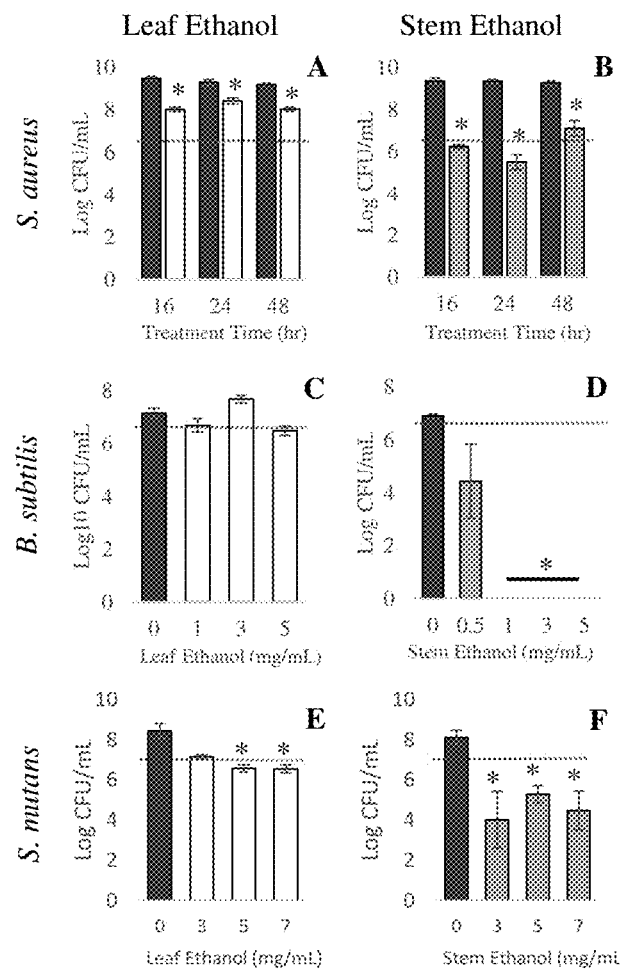
FIG. 14A, FIG. 14B, FIG. 14C, FIG. 14D, FIG. 14E, and FIG. 14F

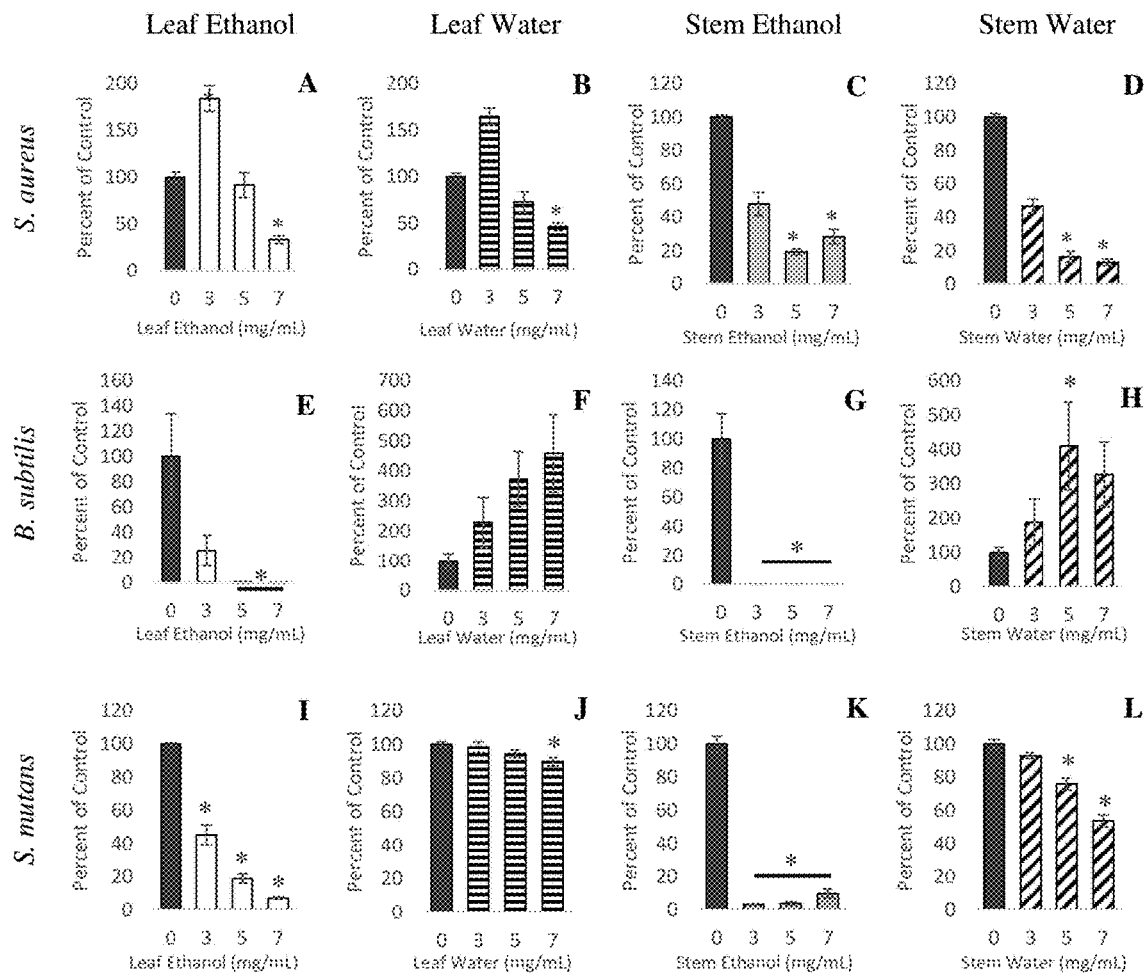
FIG. 15A, FIG. 15B, FIG. 15C, FIG. 15D, FIG. 15E, FIG. 15F, FIG. 15G, FIG. 15H, FIG. 15I, FIG. 15J, FIG. 15K, and FIG. 15L

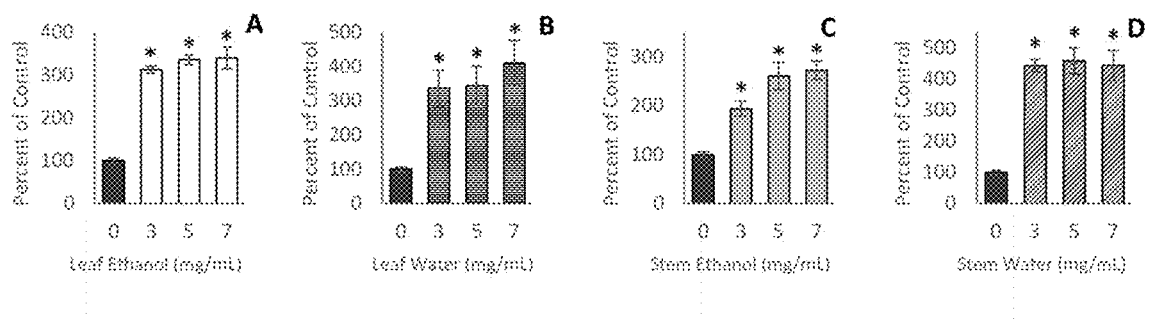
FIG. 16A, FIG. 16B, FIG. 16C, and FIG. 16D

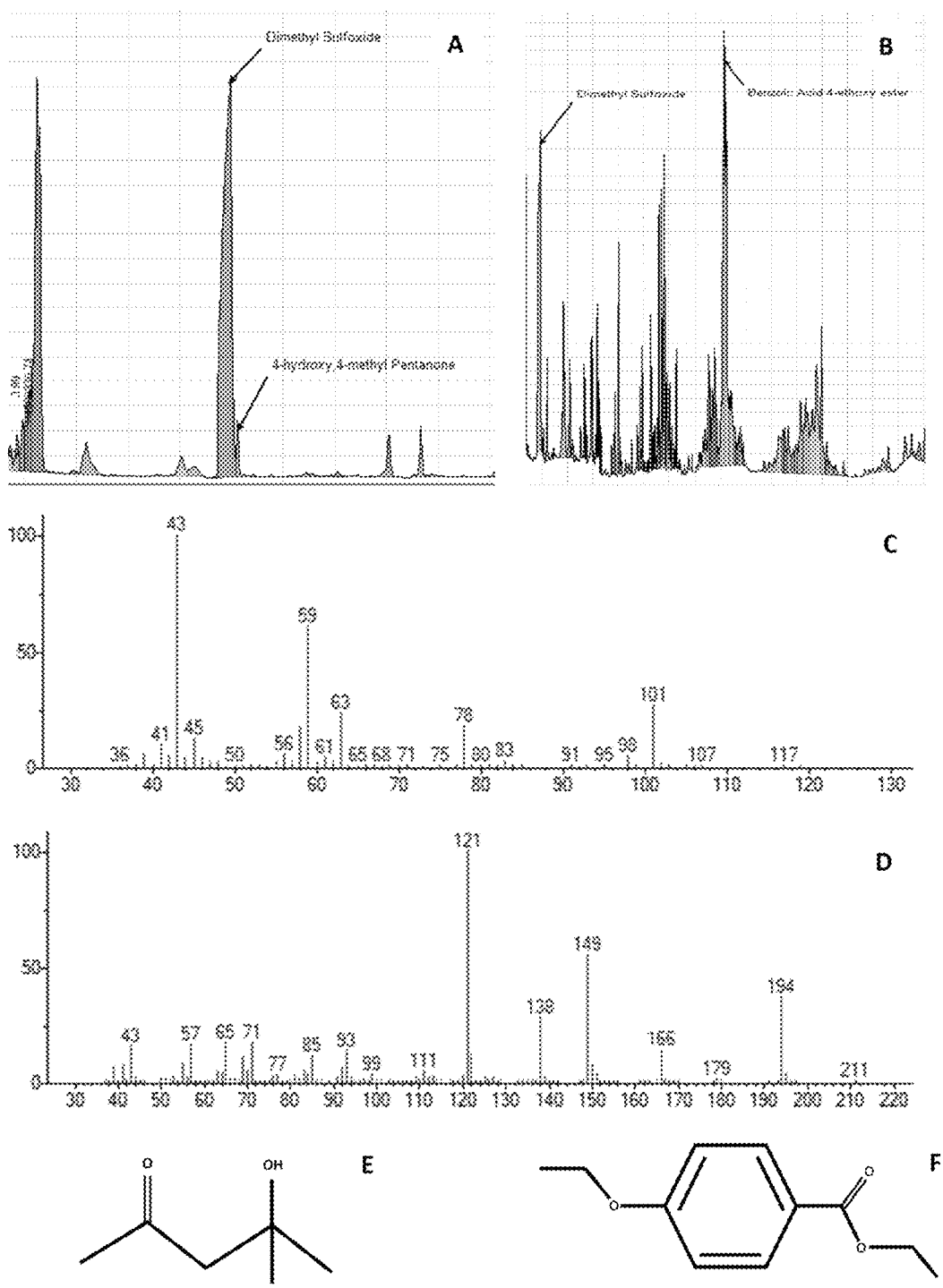
FIG. 20A, FIG. 20B, FIG. 20C, FIG. 20D, FIG. 20E, and FIG. 20F

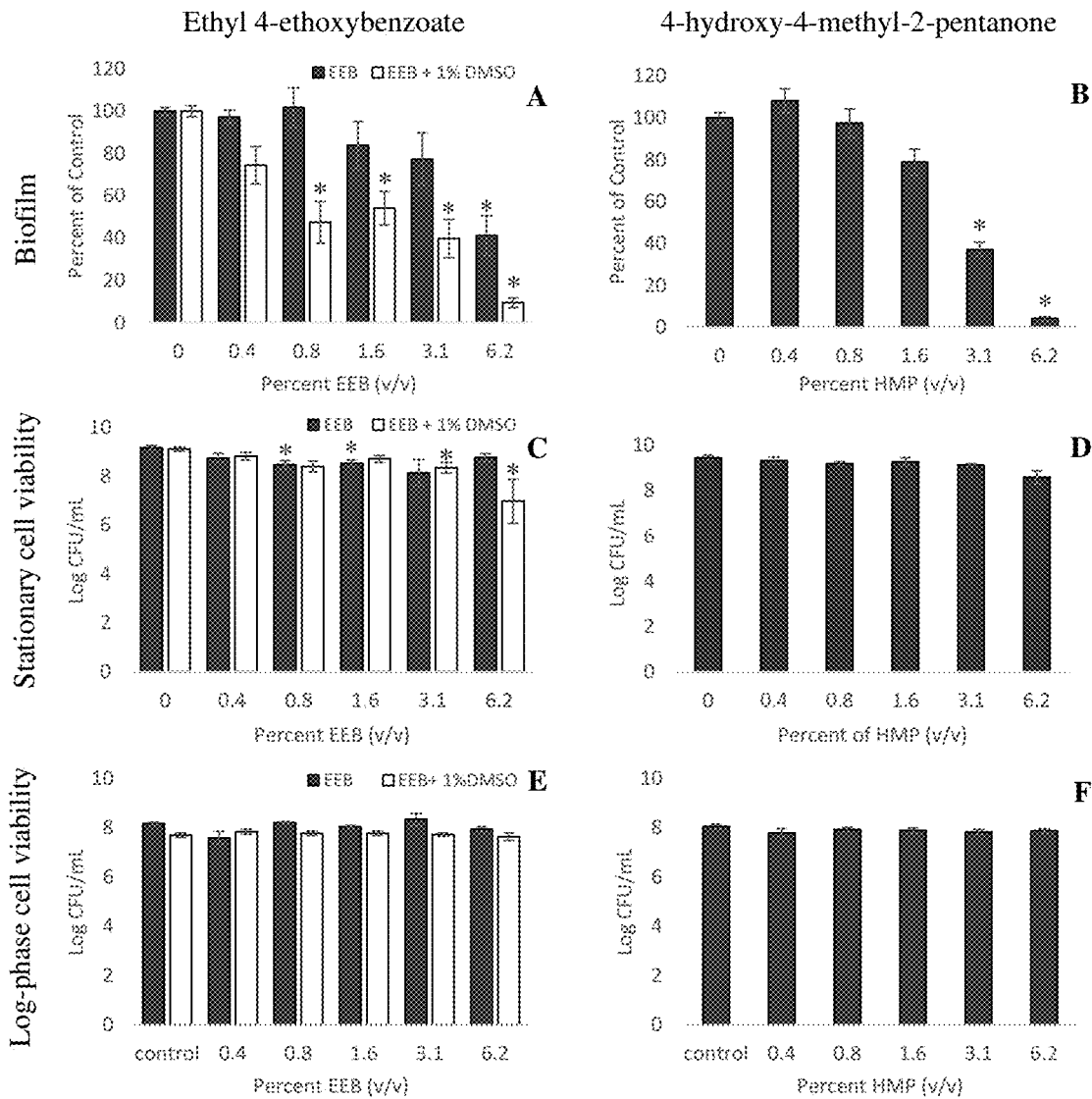
FIG. 21A, FIG. 21B, FIG. 21C, FIG. 21D, FIG. 21E, and FIG. 21F

FIG. 24A
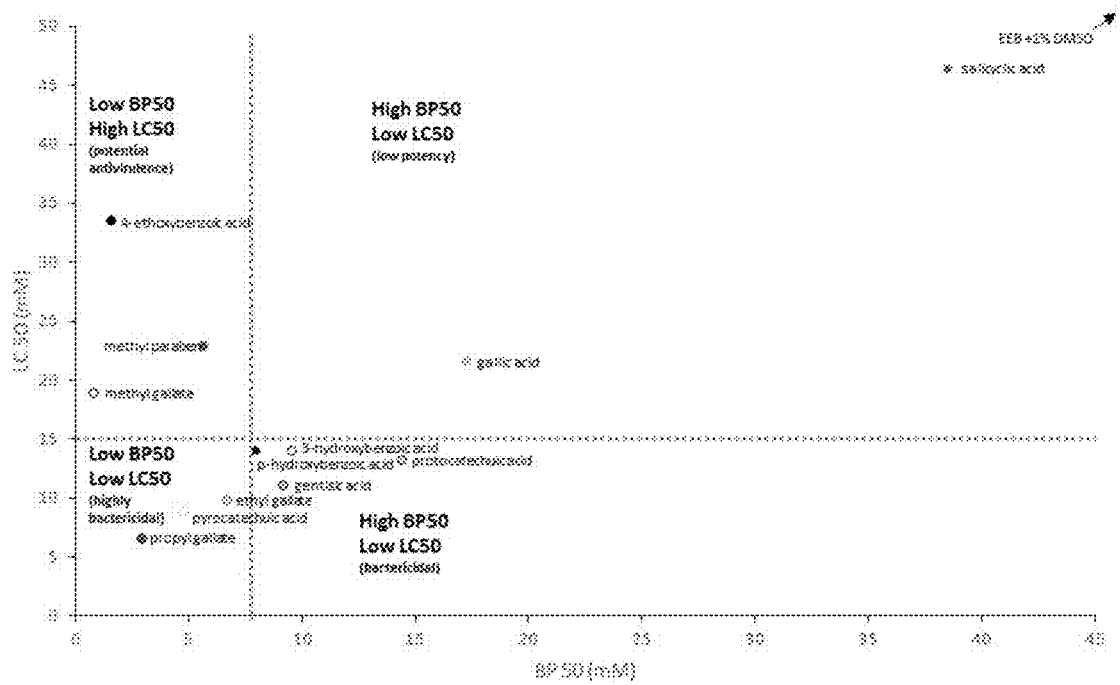
FIG. 24B, FIG. 24C, and FIG. 24D
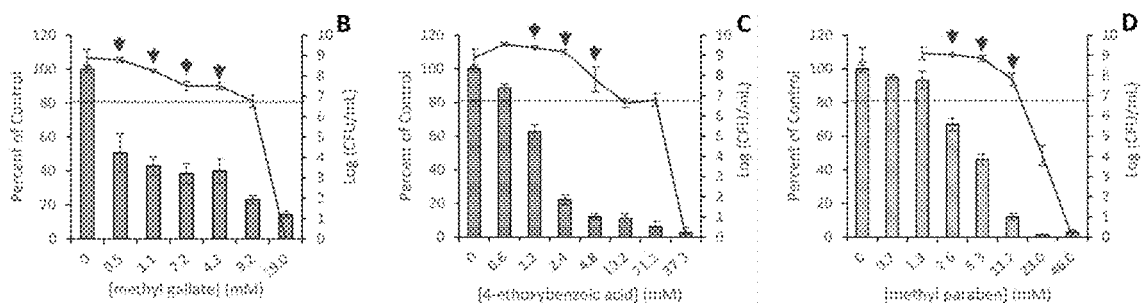

under 35 U.S.C. § 371 of PCT International Application No. PCT/US2019/031157, filed May 7, 2019, entitled "COMPOSITIONS AND METHODS RELATED TO *RHAMNUS PRINOIDES* (GESHO) EXTRACT FOR THE INHIBITION OF POLYMICROBIAL BIOFILM FORMATION," which claims the benefit of U.S. Provisional Application No. 62/667,910, filed on May 7, 2018, applications which are incorporated herein by reference in their entireties.

COMPOSITIONS AND METHODS RELATED TO *RHAMNUS PRINOIDES* (GESHO) EXTRACT FOR THE INHIBITION OF POLYMICROBIAL BIOFILM FORMATION

This is a divisional of U.S. patent application Ser. No. 17/053,496, filed on Nov. 6, 2020, which was a national stage application filed

I. BACKGROUND

Biofilms are communities of microorganisms attached to a surface and consist of microbes encased in an extracellular polymeric substance (EPS) matrix that helps to bind the bacteria to each other and acts as a barrier against numerous stressors including the penetration of antimicrobials. Biofilms form wherever non-sterile fluids interact with surfaces, so with respect to humans, there are many locations in and on the body where biofilms can form. For example, according to the National Center for Health Statistics, 37% of children between ages 2-4 in the United States and 2.4 billion people around the world have dental caries. Dental disease can be difficult to treat and if untreated can cause further systemic complications such as diabetes, pneumonia and heart disease. Dental caries are caused by pathogenic bacteria forming oral biofilms. Oral microbes also metabolize carbohydrates and produce acids as waste, this lead to the development of an overall acidic environment in the mouth, exacerbating the negative impacts of the biofilms. While various methods have been studied for disruption or prevention of biofilms (including oral biofilms), antibiotic therapy has had limited success.

Microbial biofilm infection have been associated with and contribute to the pathology of a variety of diseases including (but not limited to): chronic wounds, atopic dermatitis, endocarditis, and cystic fibrosis airway infections, urinary tract infections, and bacterial prostatitis. Nosocomial infections, those acquired by patients due to hospital stays, are also closely associated with biofilms with medical device-related infections being of particular concern. Indwelling devices such as artificial joints, artificial heart valves, venous and urinary catheters, and ventilators are all potential sources of recurrent infections once colonized by biofilms. Moreover, biofilms comprised of pathogenic microorganisms form on surfaces associated with food handling, drinking water, health care procedures and other day-to-day activities and from there can serve as a source of infection for people.

Numerous novel methods have been investigated for biofilm treatment and control; nanoparticles, phage therapy and photodynamic therapy to name a few. In spite of the various new techniques under investigation, there is still a lack of effective therapeutics that can be applied to combat biofilm infections. Furthermore, the emergence and spread of multi-drug resistance is facilitated by bacterial biofilms and has led to a push for the development of treatments that also reduce the incidence of resistance. What are needed are new compositions and methods to inhibit and/or treat biofilm formation without the negative side effect of increasing or spreading antibiotic resistance.

II. SUMMARY

Disclosed are methods and compositions related to the use of gesho extract in the inhibition of biofilm formation.

Disclosed herein are methods of methods of preventing, inhibiting, and/or reducing biofilm formation and methods of reducing, treating, and/or destroying a biofilm comprising contacting the biofilm with an extract from *Rhamnus prinoides* (gesho) stem, leaf or other plant material, an isolated small molecule derivative thereof (such as, for example, benzoic acid derivatives or gallic acid derivatives including alkylated, carboxylated, alkoxylated, hydroxylated and acetylated compounds, including, but not limited to, salicyclic acid, 3-hydroxybenzoic acid, p-hydroxybenzoic acid, p-hydroxybenzoic acid methyl ester, pyrocatechuic acid, gentisic acid, protocatechuic acid, 4-ethoxy benzoic acid (4EB), ethyl 4-ethoxybenzoate (EEB), gallic acid, methyl gallate, ethyl gallate, propyl gallate), 4-hydroxy-4-methylpentanone (HMP), adipic acid, phytol, methyl paraben, phytol acetate or 2-decanol. In one aspect, the biofilm can be in a subject; thus, also disclosed herein are methods of preventing, inhibiting, and/or reducing biofilm formation and methods of reducing, treating, and/or destroying a biofilm in a subject comprising administering to the subject a composition comprising a therapeutically effective amount of an extract from *Rhamnus prinoides Rhamnus prinoides* (gesho), an isolated small molecule derivative of thereof, (such as, for example, benzoic acid derivatives or gallic acid derivatives including alkylated, carboxylated, alkoxylated, hydroxylated and acetylated compounds, including, but not limited to, salicyclic acid, 3-hydroxybenzoic acid, p-hydroxybenzoic acid, p-hydroxybenzoic acid methyl ester, pyrocatechuic acid, gentisic acid, protocatechuic acid, 4-ethoxy benzoic acid (4EB), ethyl 4-ethoxybenzoate (EEB), gallic acid, methyl gallate, ethyl gallate, propyl gallate), 4-hydroxy-4-methylpentanone (HMP), adipic acid, phytol, methyl paraben, phytol acetate or 2-decanol. Accordingly, in one aspect disclosed herein are methods of sanitizing the surface of a medical instrument or surface susceptible to the development of biofilms comprising contacting the surface of a medical instrument or surfaces susceptible to the development of biofilms with an extract from *Rhamnus prinoides* (gesho) extract, an isolated small molecule derivative of thereof (such as, for example, benzoic acid derivatives or gallic acid derivatives including alkylated, carboxylated, alkoxylated, hydroxylated and acetylated compounds, including, but not limited to, salicyclic acid, 3-hydroxybenzoic acid, p-hydroxybenzoic acid, p-hydroxybenzoic acid methyl ester, pyrocatechuic acid, gentisic acid, protocatechuic acid, 4-ethoxy benzoic acid (4EB), ethyl 4-ethoxybenzoate (EEB), gallic acid, methyl gallate, ethyl gallate, propyl gallate), 4-hydroxy-4-methylpentanone (HMP), adipic acid, phytol, methyl paraben, phytol acetate or 2-decanol.

Also disclosed herein are methods of treating a disease associated with biofilm formation (such as, for example, tooth decay, cystic fibrosis (including, but not limited to cystic fibrosis airway infection), pneumonia, chronic wound infections, urinary tract infections, bacterial prostatitis, or device associated infections) in a subject comprising administering to the subject a composition comprising a therapeutically effective amount of an extract from *Rhamnus prinoides* (gesho), an isolated small molecule derivative of thereof (such as, for example, benzoic acid derivatives or gallic acid derivatives including alkylated, carboxylated, alkoxylated, hydroxylated and acetylated compounds, including, but not limited to, salicyclic acid, 3-hydroxybenzoic acid, p-hydroxybenzoic acid, p-hydroxybenzoic acid methyl ester, pyrocatechuic acid, gentisic acid, protocatechuic acid, 4-ethoxy benzoic acid (4EB), ethyl 4-ethoxybenzoate (EEB), gallic acid, methyl gallate, ethyl gallate, propyl gallate), 4-hydroxy-4-methylpentanone (HMP), adipic acid, phytol, methyl paraben, phytol acetate or 2-decanol.

In one aspect, disclosed herein are methods of preventing, inhibiting, and/or reducing biofilm formation and methods of reducing, treating, and/or destroying a biofilm and/or treating a disease associated with biofilm formation of any preceding aspect, wherein the biofilm is caused by a prokaryotic organism (such as, for example, a Gram positive organism including, but not limited to *Staphylococcus aureus, Streptococcus mutans*, or *Bacillus subtilis*), a Gram negative organism including *Pseudomonas aeruginosa*, and/or a eurkaryotic organism (such as, for example *Candida albicans* or *Malassezia globosa*).

Also disclosed herein are methods of preventing, inhibiting, and/or reducing biofilm formation and methods of reducing, treating, and/or destroying a biofilm and/or treating a disease associated with biofilm formation of any preceding aspect of any preceding aspect, wherein the composition is not bactericidal and/or inhibits one or more virulence factors of the microbial organism aiding in the establishment of the biofilm.

In one aspect, disclosed herein are methods of treating a disease associated with biofilm formation of any preceding aspect, wherein the disease comprises tooth decay, cystic fibrosis (including, but not limited to cystic fibrosis airway infection), pneumonia, urinary tract infections, bacterial prostatitis, pneumonia, device associated infection, endocarditis, atopic dermatitis and chronic wound infections.

Also disclosed herein are surface cleaners, disinfectants, sanitizers, mouth rinses, paints, caulks, adhesives, shampoos, and/or body washes comprising any of the gesho extracts, isolated small molecule derivatives of thereof (such as, for example, benzoic acid derivatives or gallic acid derivatives including alkylated, carboxylated, alkoxylated, hydroxylated and acetylated compounds, including, but not limited to, salicyclic acid, 3-hydroxybenzoic acid, p-hydroxybenzoic acid, p-hydroxybenzoic acid methyl ester, pyrocatechuic acid, gentisic acid, protocatechuic acid, 4-ethoxy benzoic acid (4EB), ethyl 4-ethoxybenzoate (EEB), gallic acid, methyl gallate, ethyl gallate, propyl gallate), 4-hydroxy-4-methylpentanone (HMP), adipic acid, phytol, methyl paraben, phytol acetate or 2-decanol in an amount effective to reduce, inhibit, or treat microbial organisms or biofilm formation.

In one aspect, disclosed herein are sponges, scaffolds, stents, matrixes, grafts, bandages (including adhesive bandages), wound dressings, surgical drapes, sutures, staples, surgical adhesives, salves, creams, or wound adhesives comprising a therapeutically effective amount any of the gesho extracts, isolated small molecule derivatives of thereof (such as, for example, benzoic acid derivatives or gallic acid derivatives including alkylated, carboxylated, alkoxylated, hydroxylated and acetylated compounds, including, but not limited to, salicyclic acid, 3-hydroxybenzoic acid, p-hydroxybenzoic acid methyl ester, pyrocatechuic acid, gentisic acid, protocatechuic acid, 4-ethoxy benzoic acid (4EB), ethyl 4-ethoxybenzoate (EEB), gallic acid, methyl gallate, ethyl gallate, propyl gallate), 4-hydroxy-4-methylpentanone (HMP), adipic acid, phytol, methyl paraben, phytol acetate or 2-decanol disclosed herein.

Also disclosed herein are methods of enhancing the sensitivity of a biofilm to an antibiotic or antimicrobial agent comprising contacting the biofilm with an extract from *Rhamnus prinoides* (gesho), an isolated small molecule derivative of thereof (such as, for example, benzoic acid derivatives or gallic acid derivatives including alkylated, carboxylated, alkoxylated, hydroxylated and acetylated compounds, including, but not limited to, salicyclic acid, 3-hydroxybenzoic acid, p-hydroxybenzoic acid, p-hydroxybenzoic acid methyl ester, pyrocatechuic acid, gentisic acid, protocatechuic acid, 4-ethoxy benzoic acid (4EB), ethyl 4-ethoxybenzoate (EEB), gallic acid, methyl gallate, ethyl gallate, propyl gallate), 4-hydroxy-4-methylpentanone (HMP), adipic acid, phytol, methyl paraben, phytol acetate or 2-decanol and an antimicrobial agent.

In one aspect, disclosed herein are methods of inhibiting, reducing, preventing, and/or killing a microbial organism in a subject or on a surface comprising administering a subject infected with a microbial organism causing a biofilm or contacting a microbial organism forming (or that formed) a biofilm on a surface with a therapeutically effective amount of an extract from *Rhamnus prinoides* (gesho), an isolated small molecule derivative of thereof (such as, for example, benzoic acid derivatives or gallic acid derivatives including alkylated, carboxylated, alkoxylated, hydroxylated and acetylated compounds, including, but not limited to, salicyclic acid, 3-hydroxybenzoic acid, p-hydroxybenzoic acid, p-hydroxybenzoic acid methyl ester, pyrocatechuic acid, gentisic acid, protocatechuic acid, 4-ethoxy benzoic acid (4EB), ethyl 4-ethoxybenzoate (EEB), gallic acid, methyl gallate, ethyl gallate, propyl gallate), 4-hydroxy-4-methylpentanone (HMP), adipic acid, phytol, methyl paraben, phytol acetate or 2-decanol. In one aspect, the method can comprise the further administration of an antimicrobial agent.

III. BRIEF DESCRIPTION OF THE DRAWINGS

The accompanying drawings, which are incorporated in and constitute a part of this specification, illustrate several embodiments and together with the description illustrate the disclosed compositions and methods.

FIGS. 1A, 1B, 1C, and 1D shows effects of ethanol and aqueous extracts on *Streptococcus mutans* biofilm formation. Bars indicate the extent of *S. mutans* biofilm formation after treatment with leaf ethanol (white bars), leaf aqueous (horizontal striped bars), stem ethanol (grey bars) or stem aqueous (slanted striped bars) extracts relative to untreated controls. All assays were performed in triplicate (n=12). Error bars are standard error of the mean. Asterisks (*) indicated a significant difference (p<0.05) between the treated samples and untreated control.

Figures 4A, 4B:
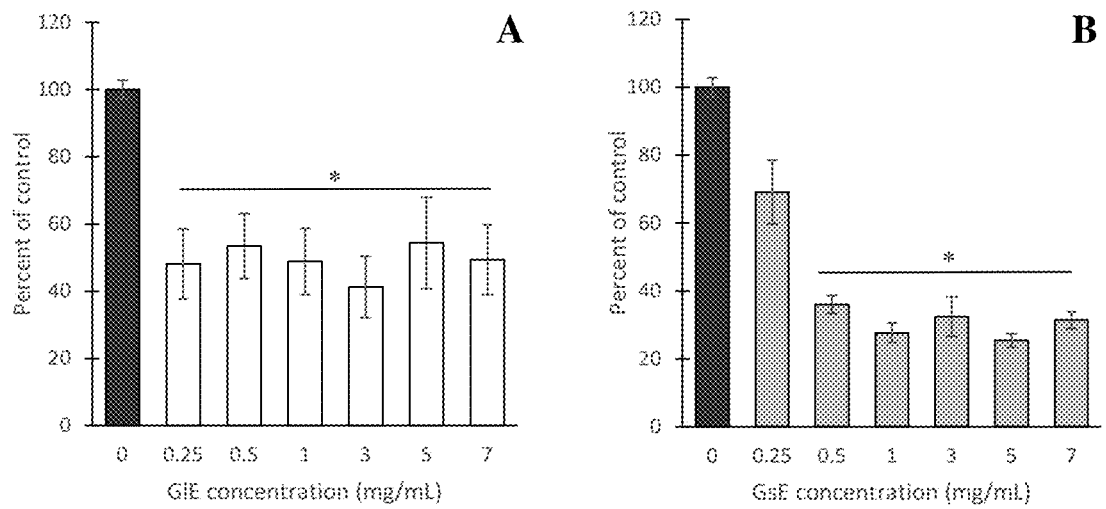

FIGS. 4A and 4B effects of gesho ethanol extracts on *Candida albicans* biofilm formation. Bars indicate the extent of *C. albicans* biofilm formation after treatment with leaf ethanol (white bars) or stem ethanol (grey bars) extracts relative to untreated controls. All assays were performed in triplicate. Error bars are standard error of the mean. Asterisks (*) indicated a significant difference (p<0.05) between the treated samples and untreated control.

Figure 5:
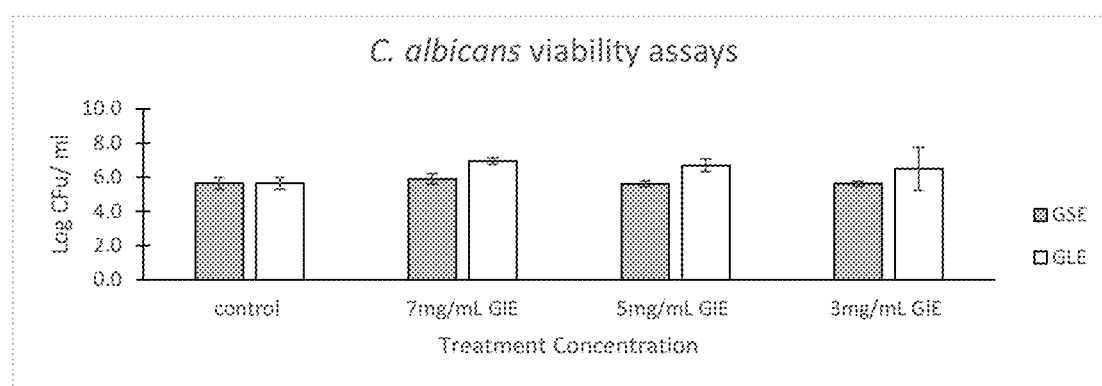

FIG. 5 shows a viability assay showing C. albicans Log CFU/ml increase.

Figure 6:
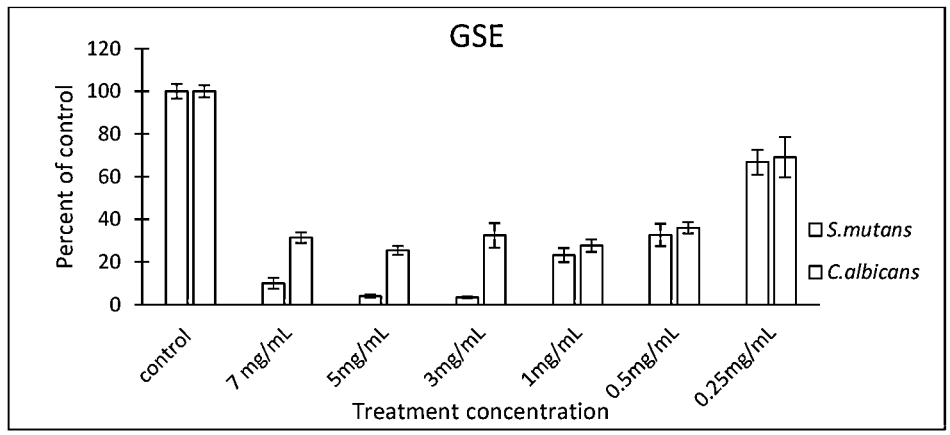

FIG. 6 shows the effect of GSE on both S. mutans and C. albicans showing 3 mg/ml with highest effect on S. mutans.

Figure 7:
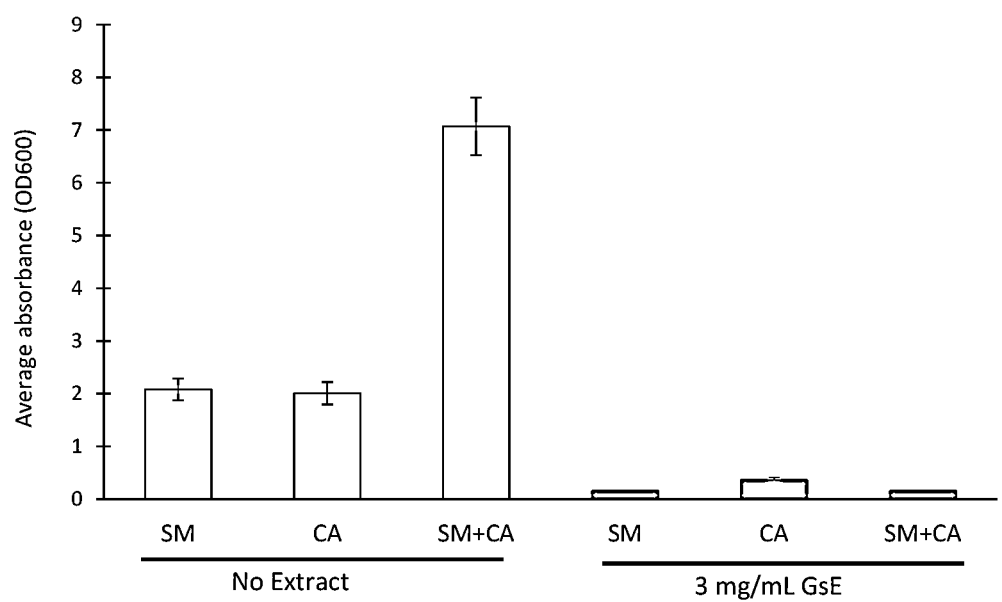

FIG. 7 shows the effect of GSE 3 mg/ml on S. mutans and C. albicans polymicrobial biofilms, each two similar letters represent a significant difference between each other, p<0.05.

Figure 8:
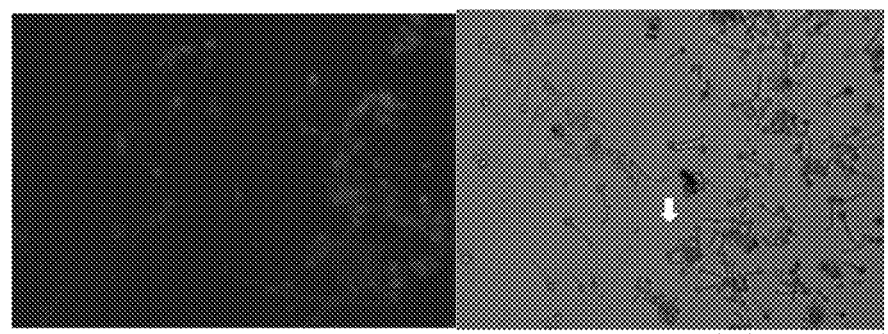

FIG. 8 shows images of treated Dual Species biofilms of C. albicans and S. mutans, white arrow points at S. mutans cells.

Figure 9:
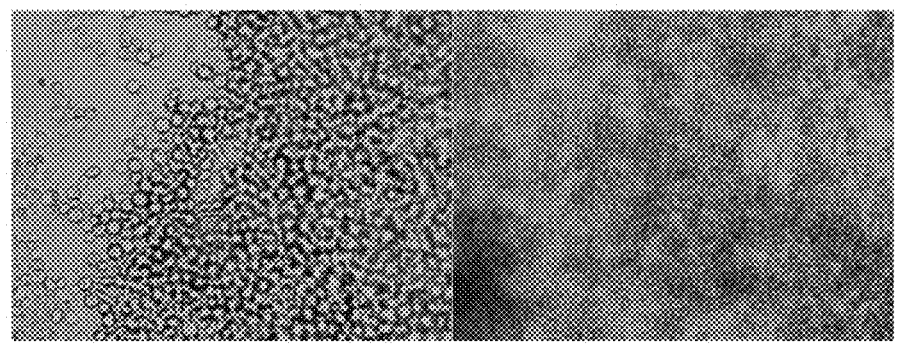

FIG. 9 shows images of untreated polymicrobial biofilms of C. albicans and S. mutans showing dense biofilms.

Figure 10:
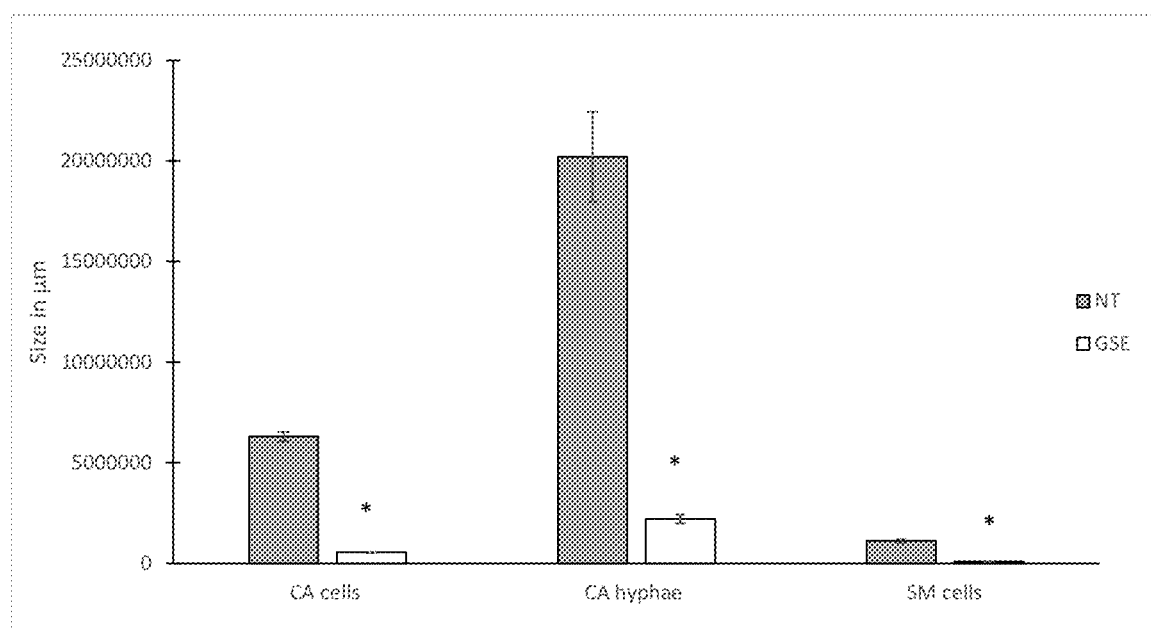
Figure 12A:
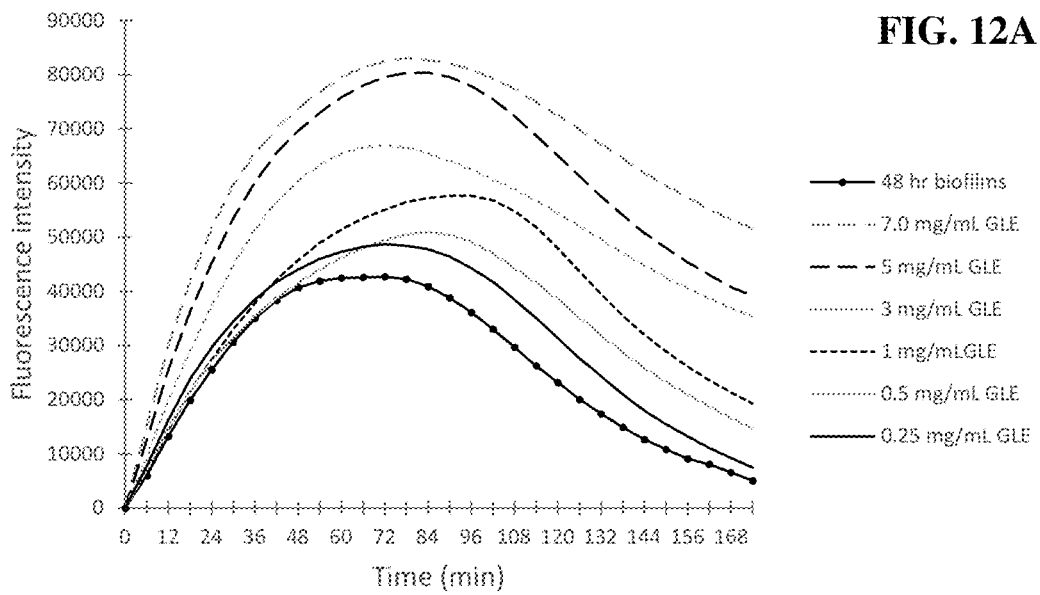
Figure 12B:
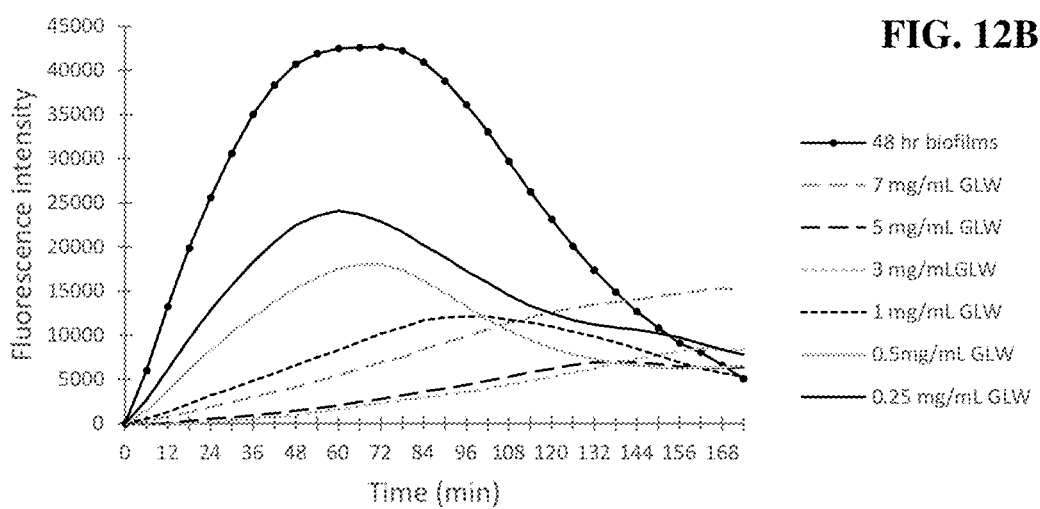
Figure 12C:
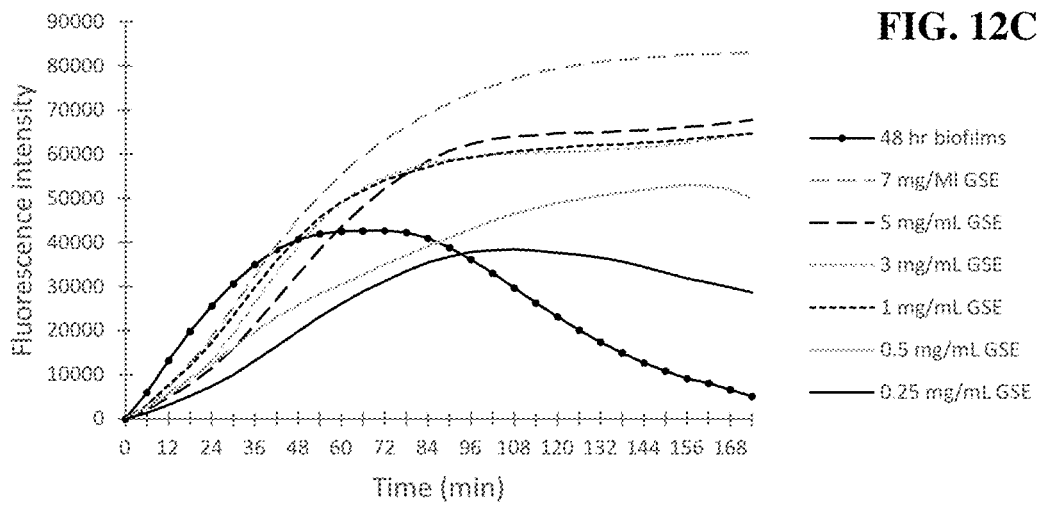
Figure 12D:
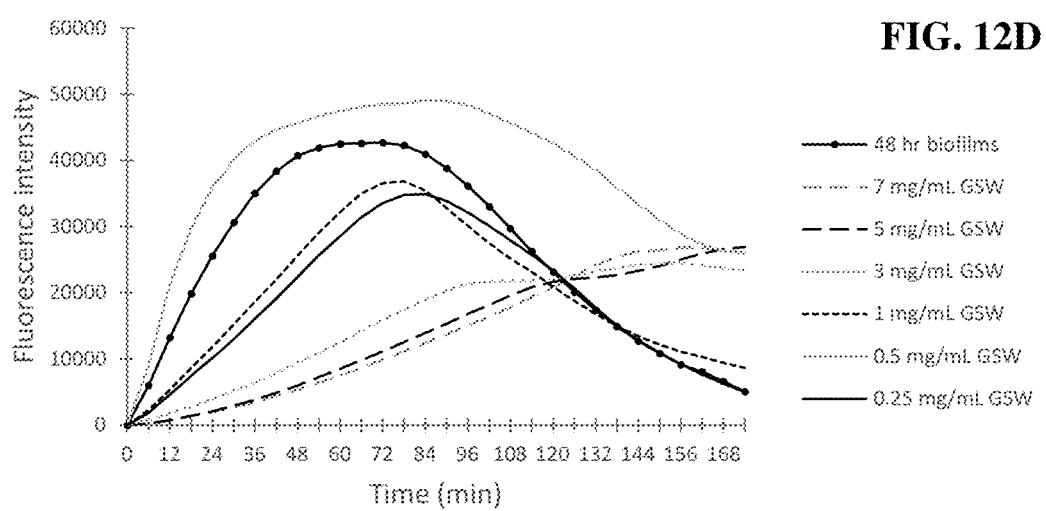

FIG. 10 shows a size measurement of untreated vs. treated polymicrobial biofilms, (*) indicates significant difference (p<0.05) between treated samples and the untreated control.

FIGS. 11A, 11B, 11C, and 11D shows effects of the ethanol and aqueous extracts on Streptococcus mutans biofilm killing. Respiration rates of 24 hr S. mutans biofilms treated with leaf ethanol (white bars), leaf aqueous (horizontal striped bars), stem ethanol (grey bars) or stem aqueous (slanted striped bars) extracts was compared to untreated control samples. Bars indicate the average time for resazurin to reach maximum fluorescence intensity. All assays were performed in triplicate (n=15). Error bars are standard error of the mean. Asterisks (*) indicated a significant difference (p<0.05) between the extract treated samples and untreated control.

FIGS. 12A, 12B, 12C and 12D shows effects of the ethanol and aqueous extracts on Candida albicans biofilm killing. Respiration rates of 24 hr C. albicans biofilms treated with leaf ethanol (12A), leaf aqueous (12B), stem ethanol (12C) or stem aqueous (12D) extracts was compared to untreated control samples. All assays were performed in triplicate (n=12).

FIGS. 13A, 13B, 13C, 13D, 13E, 13F, 13G, 13H, 13I, 13J, 13K, and 13L show the bactericidal effects of aqueous and ethanol extracts on log-phase, planktonic cells. (13A, 13B, 13C, and 13D) Staphylococcus aureus (n=3-6); (13E, 13F, 13G, and 13H) Bacillus subtilis (n=3-4) and (13I, 13J, 13K, and 13L) Streptococcus mutans (n=3-4). Bars indicate number of bacteria present in culture following exposure to extracts for 24 h. Legend: leaf ethanol (white bars), leaf aqueous (horizontal striped bars), stem ethanol (grey bars), stem aqueous (slanted striped bars). Error bars are standard error of the mean. ANOVA and Kruskal-Wallis tests were performed; (*) indicates a significant difference (p<0.05) between treated samples and the untreated control.

FIGS. 14A, 14B, 14C, 14D, 14E, and 14F show the effects of ethanol extracts on stationary phase planktonic cell viability. (14A-14B) Staphylococcus aureus (n=3), (14C-14D) Bacillus subtilis (n=3-4), (14E-14F) Streptococcus mutans (n=3). Bars indicate the number of viable cells after growth for 24 h in the presence of stem (light grey bars) and leaf (white bars) ethanol extracts. Black bars represent untreated controls. The inoculum cell density is indicated by a red dotted line. Error bars are standard error of the mean. ANOVA, T-test, Kruskal-Wallis tests were performed; (*) indicates a significant difference (p<0.05) between treated samples and the untreated control.

FIGS. 15A, 15B, 15C, 15D, 15E, 15F, 15G, 15H, 15I, 15J, 15K, and 15L show the effects of aqueous and ethanol extracts on Gram positive bacterial biofilm formation. (15A, 15B, 15C, and 15D) Staphylococcus aureus (n=10-15), (15E, 15F, 15G, and 15H) Bacillus subtilis (n=3-4) and (15I, 15J, 15K, and 15L) Streptococcus mutans (n=12). Bars indicate the extent of biofilm formation relative to untreated controls. Legend: leaf ethanol (white bars), leaf aqueous (horizontal striped bars), stem ethanol (grey bars), stem aqueous (slanted striped bars). Error bars are standard error of the mean. ANOVA and Kruskal-Wallis tests were performed; (*) indicates a significant difference (p<0.05) between treated samples and the untreated control.

FIGS. 16A, 16B, 16C, and 16D show the effect of aqueous and ethanol extracts of Pseudomonas aeruginosa biofilm formation. Bars indicate the extent of biofilm formation relative to untreated controls. Legend: leaf ethanol (white bars), leaf aqueous (horizontal striped bars), stem ethanol (grey bars), stem aqueous (slanted striped bars). Error bars are standard error of the mean. Kruskal-Wallis tests were performed; (*) indicates a significant difference (p<0.05) between treated samples and the untreated control.

Figure 17:
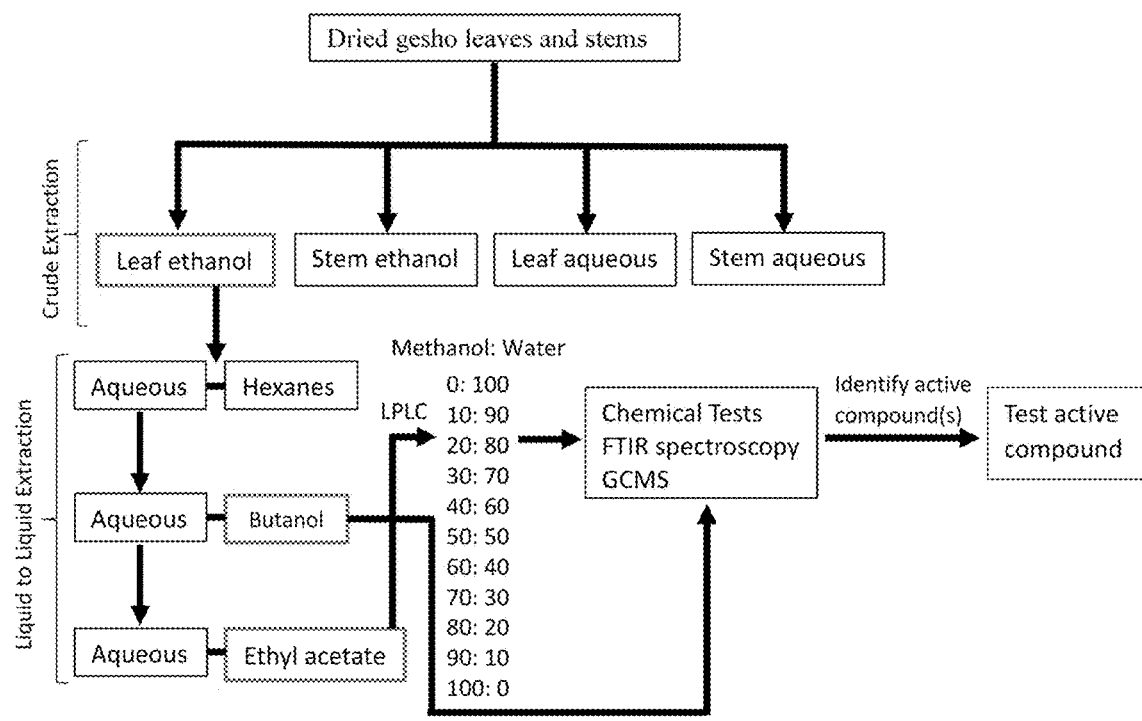

FIG. 17 shows a diagram of gesho leaf ethanol extract fractionation and chemical analysis. Crude ethanol extracts were prepared from ground leaves of R. prinoides, followed by liquid to liquid fractionation using hexanes, butanol and ethyl acetate. Butanol and ethyl acetate fractions were further separated by column chromatography and then analyzed via colorimetric chemical tests, Fourier transform infrared spectroscopy and gas chromatography-mass spectrometry (GCMS). Chemical compounds identified via GCMS were screened for antimicrobial and anti-biofilm activity.

Figures 18A, 18B:
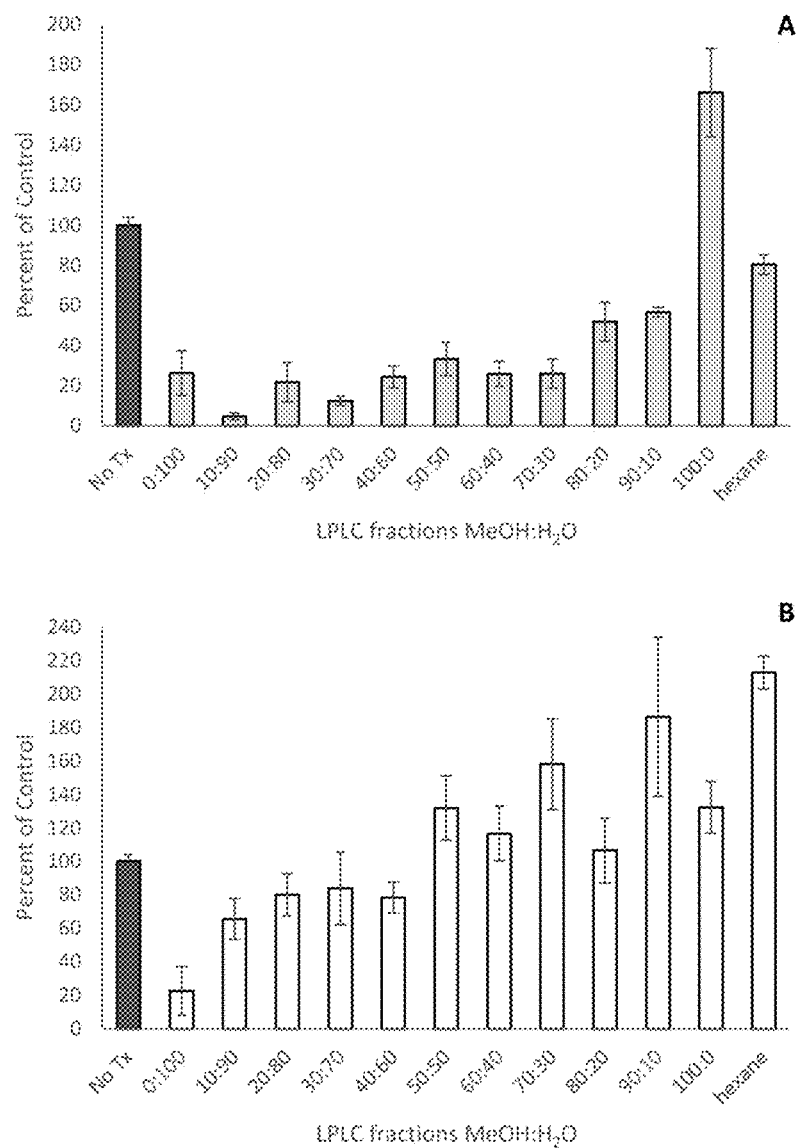

FIGS. 18A and 18B show the effect of low pressure liquid chromatography fractions for Staphylococcus aureus biofilm formation. Bars indicate the extent of biofilm formation relative to untreated controls. Legend: further separation of the butanol liquid to the liquid fraction (grey bars), further separation of the ethyl acetate liquid to liquid fraction (white bars). Error bars are standard error of the mean.

Figures 19A, 19B:
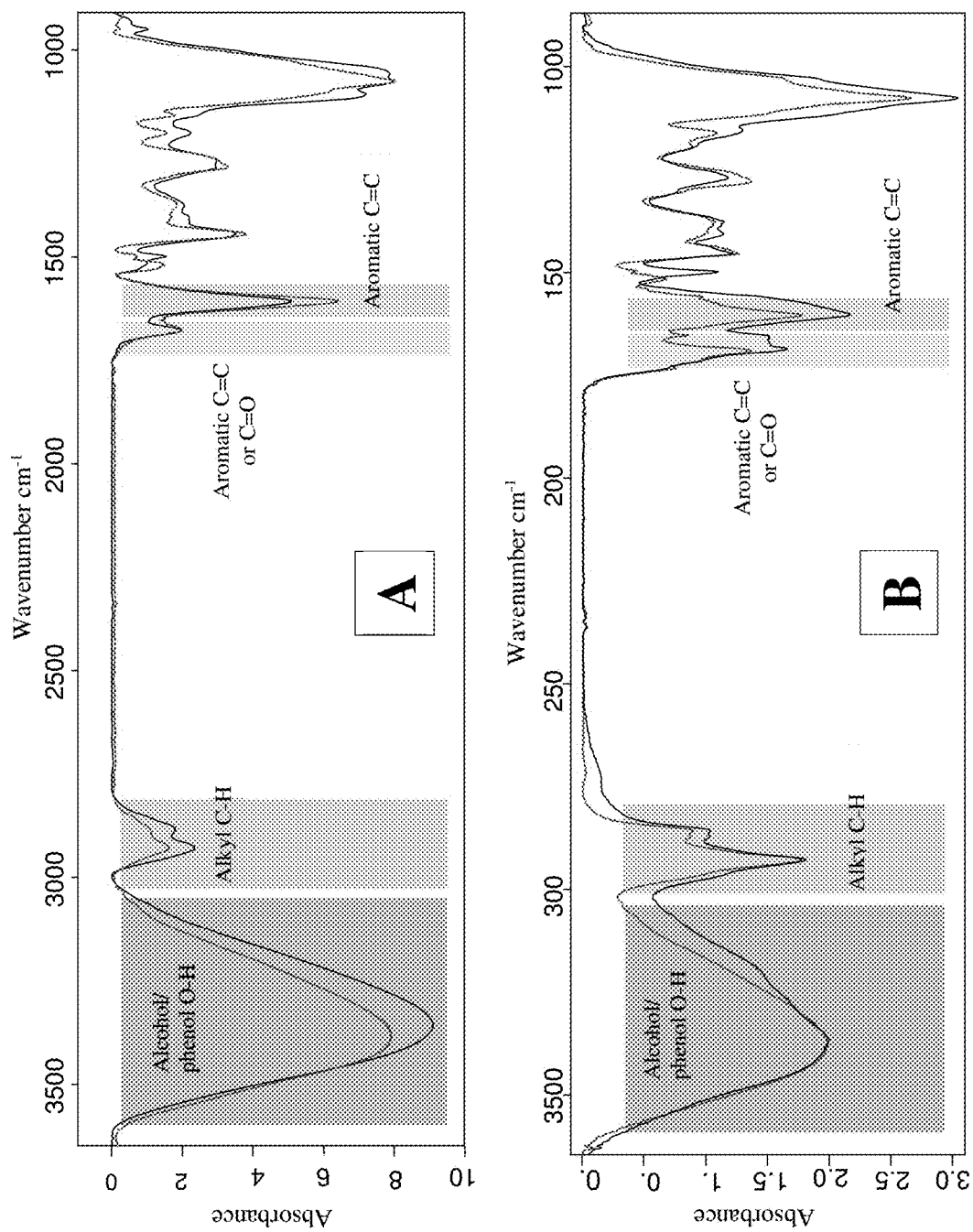

FIGS. 19A and 19B show a Fourier transform infrared spectroscopy of butanol and ethyl acetate fractions. Butanol (19A) and ethyl acetate (19B) fractions prepared on May 26, 2017 (black) and Jun. 15, 2017 (red) exhibit strong hydroxyl (blue box), alkane (green box) and alkene (yellow and grey box) peaks. Peak strength was 4-5 times stronger in the butanol fraction chromatogram than the ethyl acetate.

FIGS. 20A, 20B, 20C, 20D, 20E, and 20F show a gas chromatography mass spectrometry analysis of butanol fraction. 4-hydroxy-4-methyl-2-pentanone (20A, 20C, and 20E) and Ethyl 4-ethoxybenzoate (20B, 20D, and 20F) were identified as compounds present in the butanol fraction. There are numerous additional peaks in the mixture whose identities were not resolved or evaluated for antimicrobial or anti-biofilm activity.

FIGS. 21A, 21B, 21C, 21D, 21E, and 21F show the effects of ethyl 4-ethoxybenzoate and 4-hydroxy-4-methyl-2-pentanone on S. aureus biofilm formation and planktonic cell viability. Top row, effect on biofilm formation. Middle row, effect on stationary phase cell viability. Bottom row, effect on log phase cell viability. Bars indicate the impact of treatments after 24 h. Legend: ethyl 4-ethoxybenzoate (EEB) and 4-hydroxy-4-methyl-2-pentanone (HMP) with (white bars) or without (black bars) the presence of 1% DMSO. Each assay was performed in triplicate and error bars represent the standard error of the mean. An ANOVA test was performed; (*) indicates a significant difference of (p<0.05) between the treated samples and the untreated control.

Figures 22A, 22B:
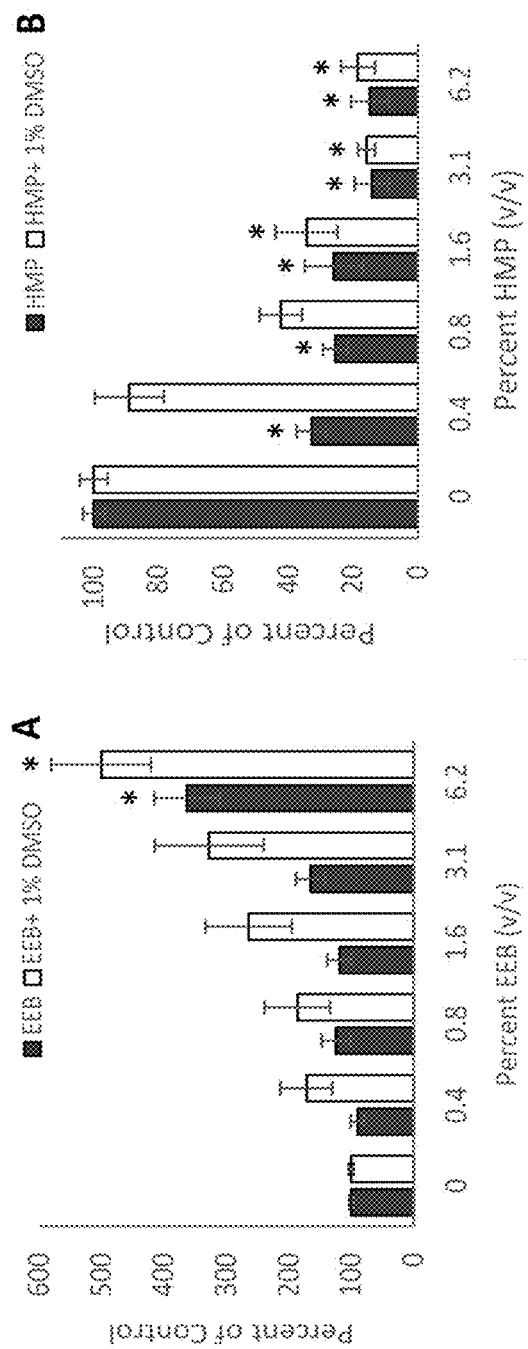

FIGS. 22A and 22B show the effect of ethyl 4-ethoxybenzoate and 4-hydroxy-4-methyl-2-pentanone on Pseudomonas aeruginosa biofilm formation. Bars indicate the extent of biofilm formation relative to untreated controls. Error bars are standard error of the mean. Kruskal-Wallis tests were performed; (*) indicates a significant difference (p<0.05) between treated samples and the untreated control.

Figure 23:
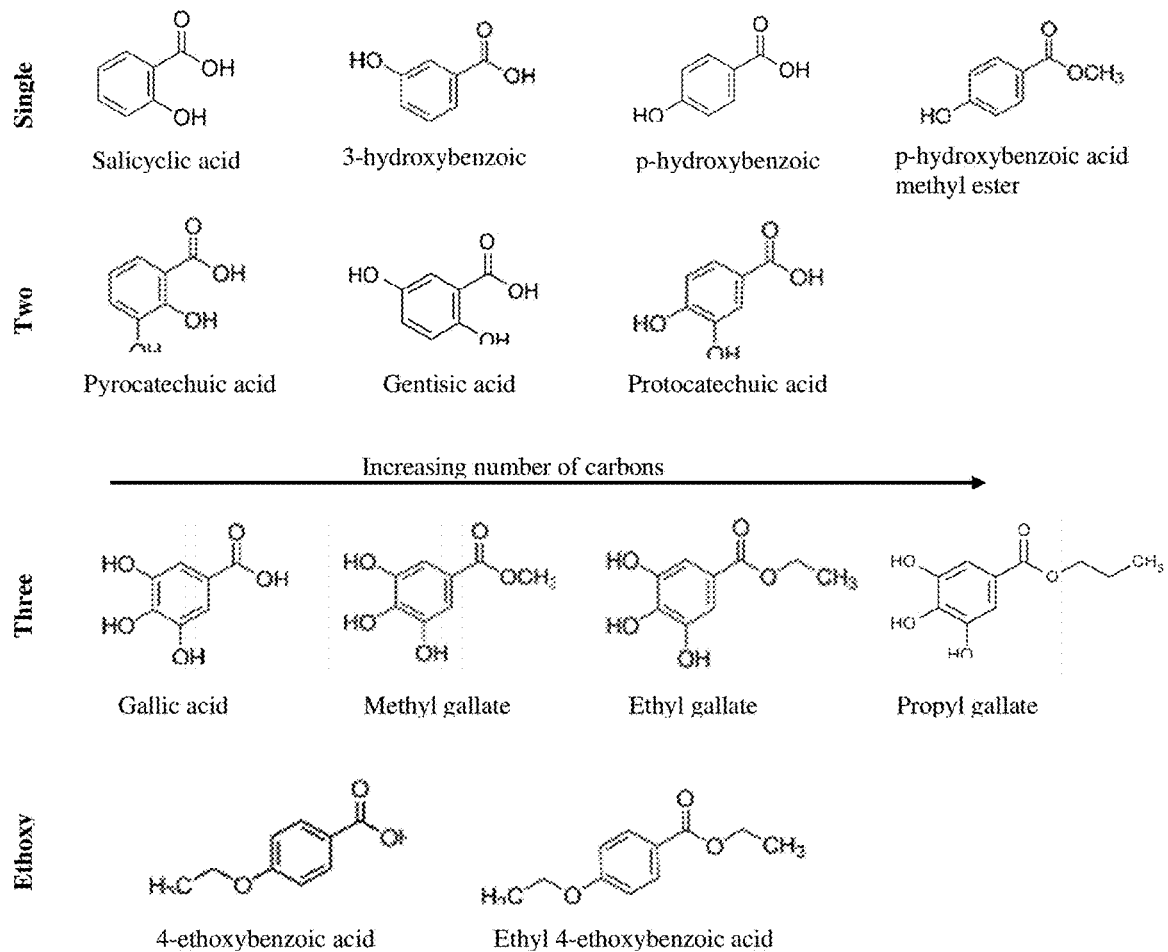

FIG. 23 shows benzoic compounds tested in this study. All compounds used in this study were structurally similar to the gesho derived compound ethyl 4-ethoxybenzoic acid. Compounds were selected to investigate the effects of functional group location on antibiofilm activity.

FIGS. 24A, 24B, 24C, and 24D show the effects of benzoic compounds on *Staphylococcus aureus* biofilm formation and viability. Data points represent the compound concentrations that resulted in half the maximum biofilm formation (BP50) and half the maximum observed planktonic growth (LC50). FIG. 24A shows that compounds were characterized as antivirulent, bactericidal or low potency. Antivirulent concentrations of methyl gallate (24B), 4-ethoxybenzoic acid (24C) and methyl paraben (24D) are indicated by arrow heads (24B, 24C, and 24D). The inoculum cell density is represented by the horizontal dotted line.

Figure 25:
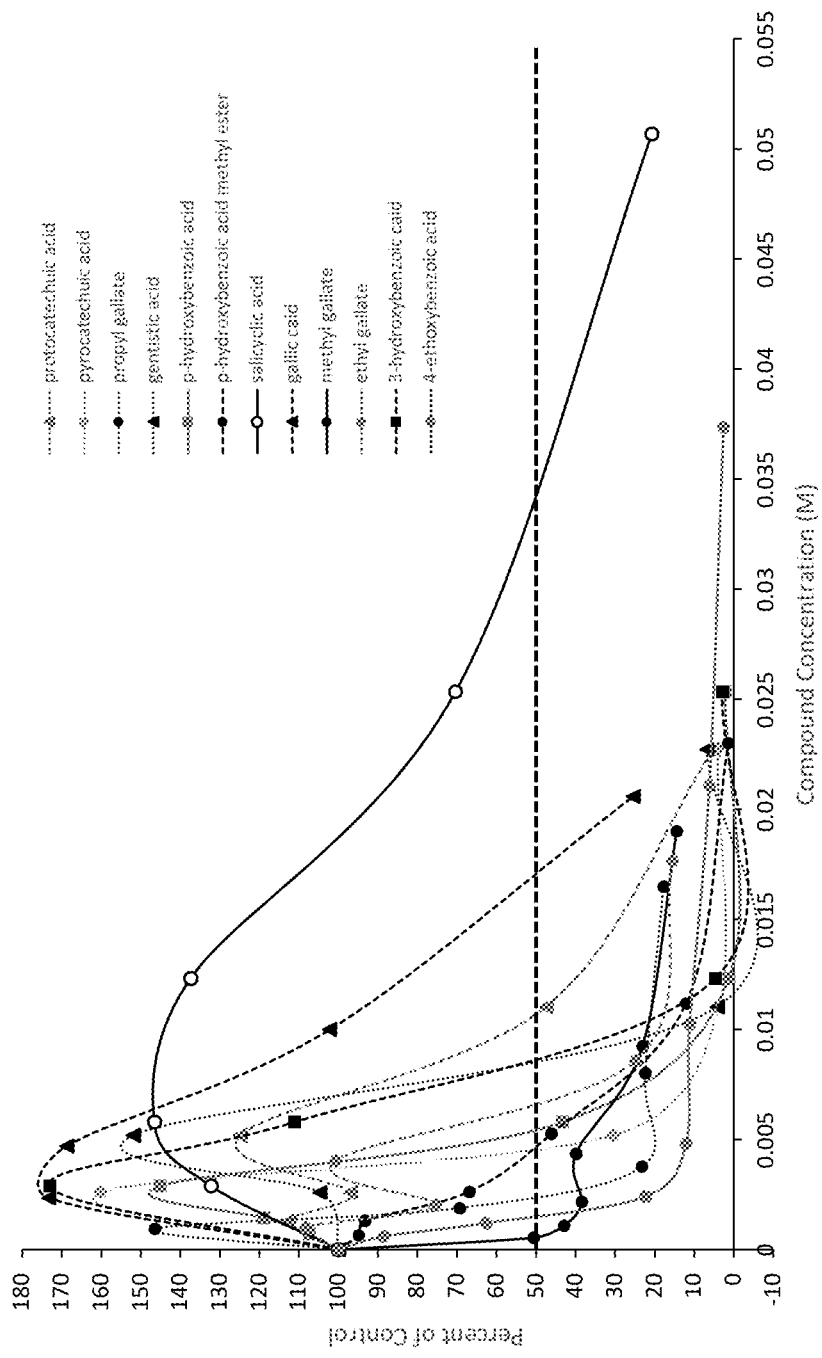

FIG. 25 shows concentration dependent effects of benzoic compounds on *Staphylococcus aureus* biofilm formation. Various concentrations of benzoic compounds were tested for anti-biofilm activity. Data from this analysis was used to calculate the concentration of each compound that resulted in half the maximum biofilm formation (BP50). Data points that lie on the horizontal dotted line indicated the BP50 concentration.

Figure 26:
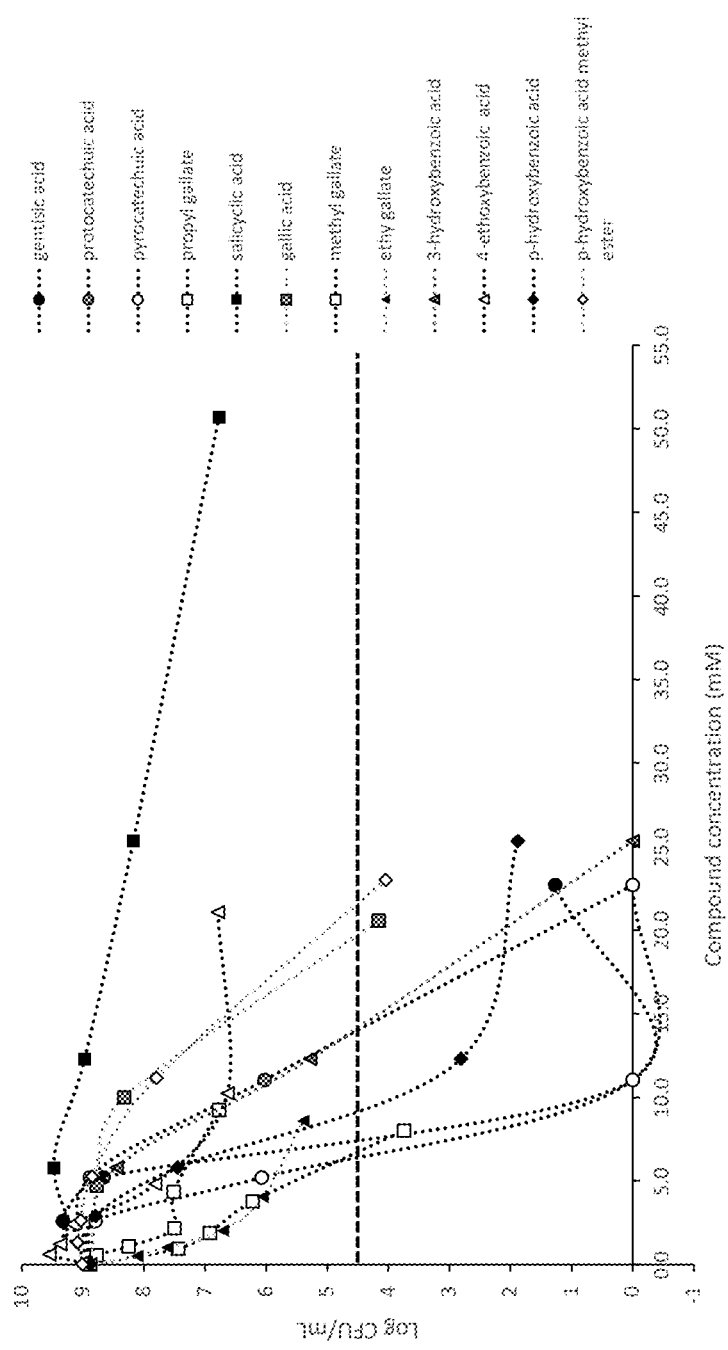

FIG. 26 shows concentration dependent effects of benzoic compounds on stationary phase *Staphylococcus aureus*. Various concentrations of benzoic compounds were tested for biocidal activity. Data from this analysis was used to calculate the concentration of each compound that resulted in half the maximum cell growth (LC50). Data points that lie on the horizontal dotted line indicated the LC50 concentration.

Figure 27:
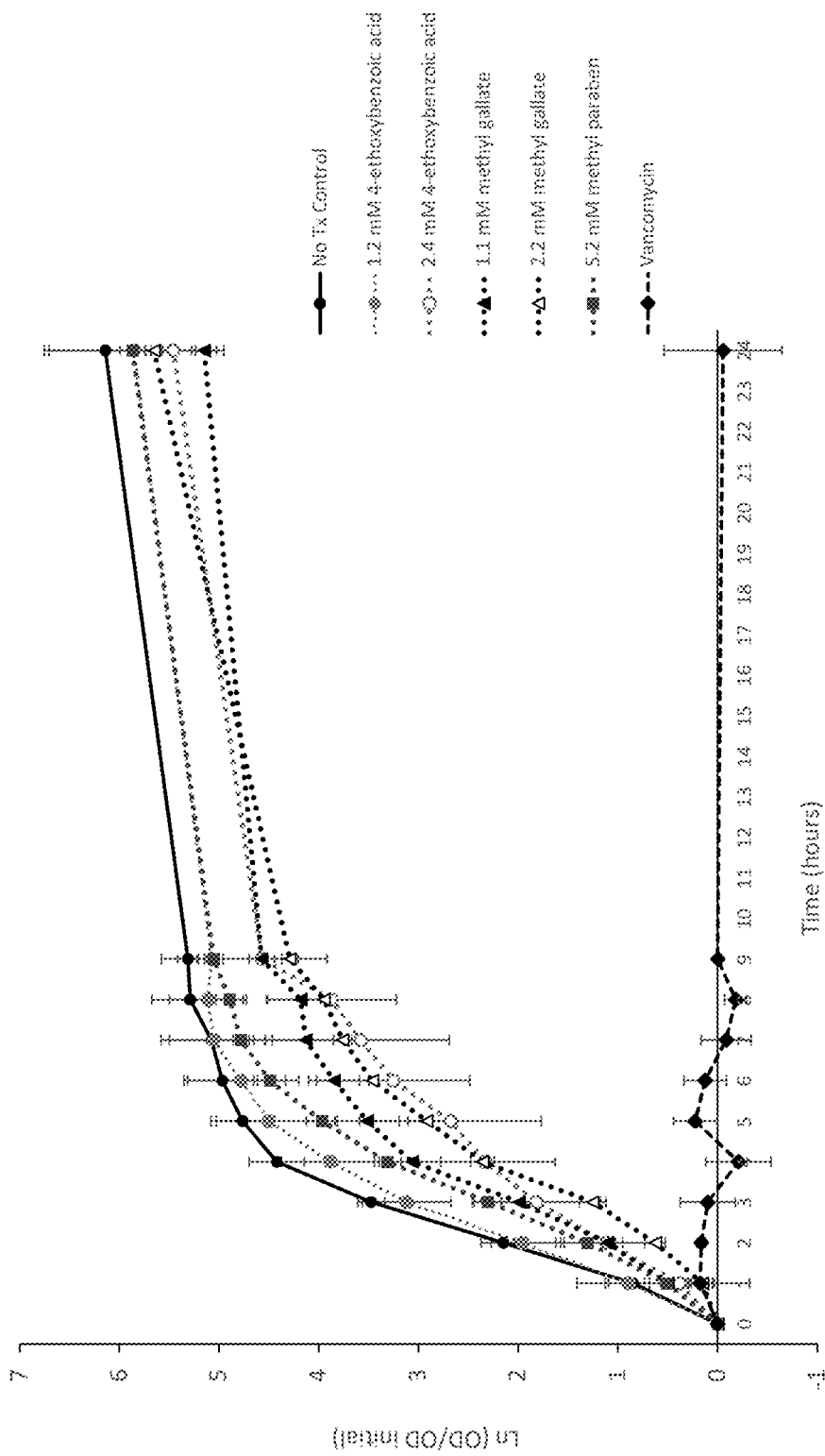

FIG. 27 shows the effects of 4-ethoxybenzoic acid, methyl gallate and methyl paraben on *Staphylococcus aureus* growth. Growth of *S. aureus* in the presence of 1.2 and 2.4 mM 4-ethoxybenzoic acid, 1.1 and 2.2 mM methyl gallate or 5.2 mM methyl paraben was measured over 24 hours. Untreated (No Tx Control) and 1.1 ☐☐☐ vancomycin treated samples served as negative and positive controls, respectively. Growth rates were calculated from t=0 and t=4 and are presented in table 1 along with the percent attenuation.

Figure 28A:
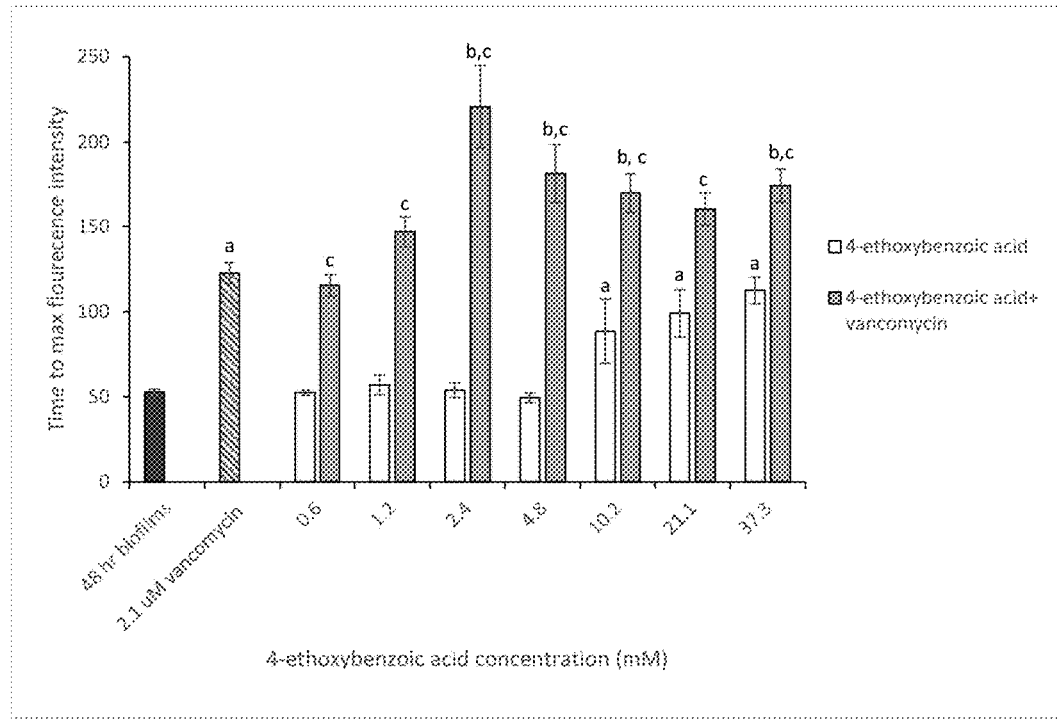
Figure 28B:
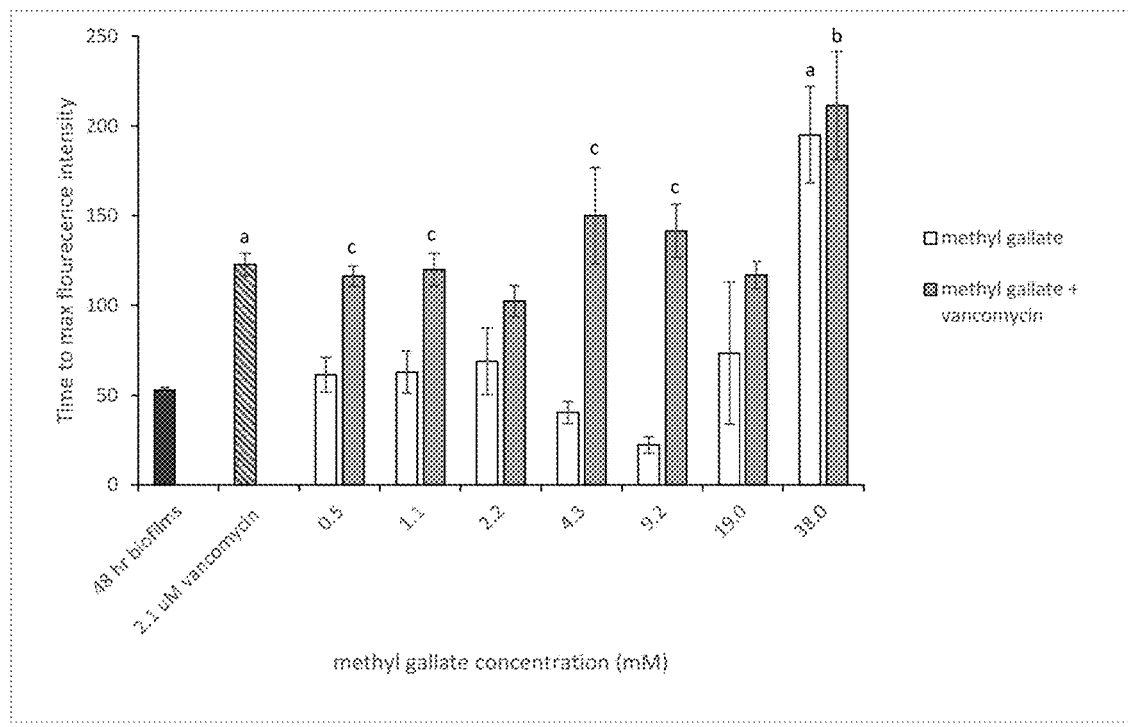

FIGS. 28A and 28B shows biofilm killing activity of compound and vancomycin combination treatments. 4-ethoxybenzoic acid (12A) and methyl gallate (12B) were assess biofilm killing activity alone (white bars) and in combination with 1.1☐☐☐ vancomycin (grey bars). Untreated biofilms (black bar) and 1.1 ☐☐☐ vancomycin (stripped bar) treated samples served as controls. Diamonds indicate samples that did not reach maximum fluorescence intensity during the 3 hour time course.

Figure 29:
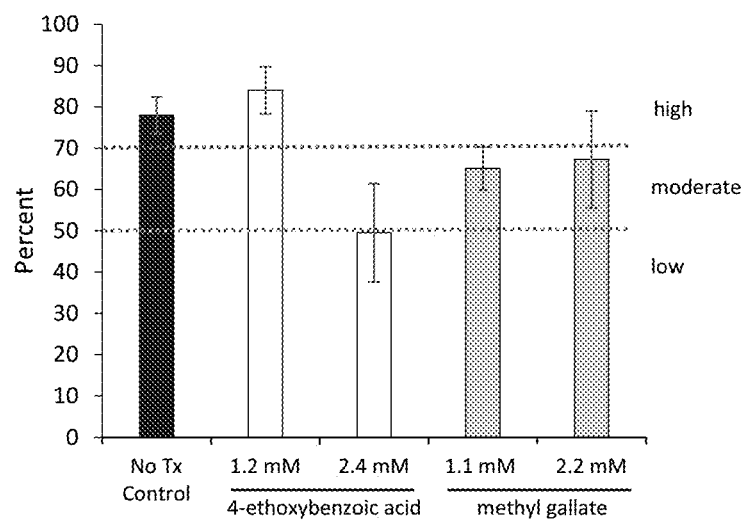

FIG. 29 shows the effects of 4-ethoxybenzoic acid and methyl gallate on *Staphylococcus aureus* hydrophobicity. The hydrophobicity of cells treated with 4-ethoxybenzoic acid (white bars) or methyl gallate (grey bars) were categorized as low (≤50), moderate (50%-70%) or high (≥70%). Untreated (No Tx Control) samples served as a negative control.

Figure 30:
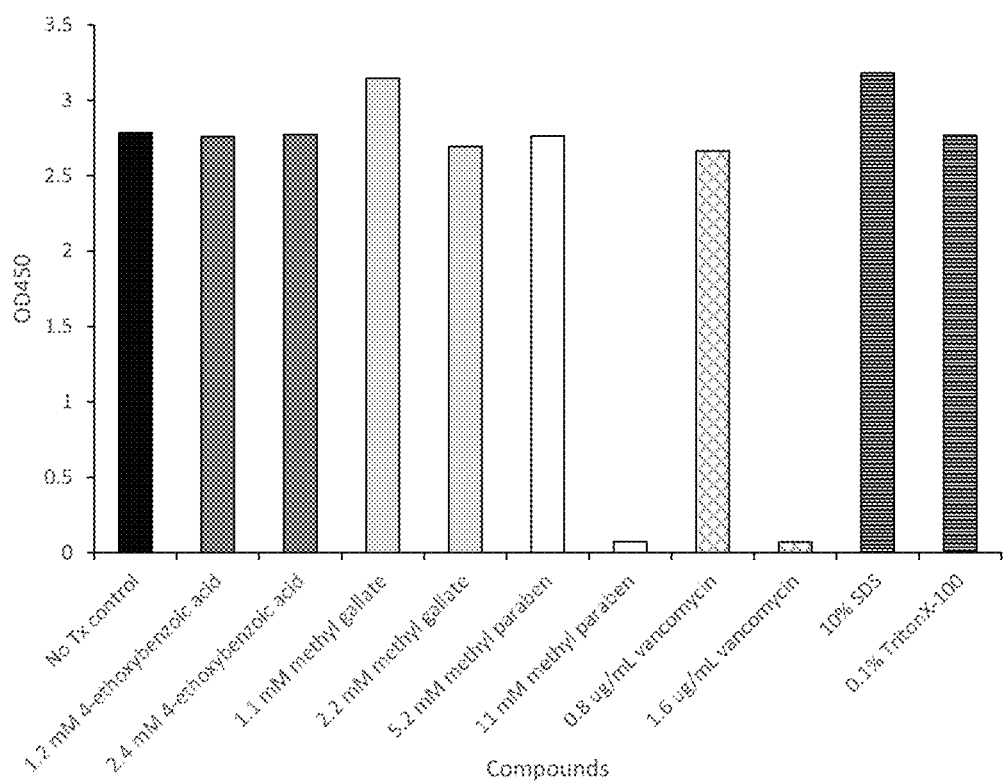

FIG. 30 shows the effects of 4-ethoxybenzoic acid, methyl gallate and methyl paraben on *Staphylococcus aureus* hemolytic activity. Bars represent the presence of hemolytic activity on rabbit red blood cells. The no treatment, 10% SDS and 0.1% TritonX-100 samples acted as positive controls and 1.6 ug/mL vancomycin was the negative control.

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

The term "subject" refers to any individual who is the target of administration or treatment. The subject can be a vertebrate, for example, a mammal. In one aspect, the subject can be human, non-human primate, bovine, equine, porcine, canine, or feline. The subject can also be a guinea pig, rat, hamster, rabbit, mouse, or mole. Thus, the subject can be a human or veterinary patient. The term "patient" refers to a subject under the treatment of a clinician, e.g., physician.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

Biofilms are complex microbial communities attached to surfaces. They are microbial cells encased in an extracellular polymeric matrix composed of proteins, carbohydrates and extracellular DNA that acts as a physical and enzymatic barrier to antibiotic penetration. Biofilms are found to be different from planktonic cells in their different regulation of some of their genes as well as their slow growth rates. Antibiotic treatments are effective against metabolically active cells on the other periphery of the biofilm but the inability of compounds to percolate into the interior of the biofilm matrix prevent more mature cells from exposure. In addition to the extracellular matrix, biofilms contain metabolically dormant persister cells that are intrinsically resistant to antibiotics. Biofilms also acquire and perpetuate the spread of antibiotic resistance due to horizontal gene transfer. The matrix-stabilized environment within biofilms is beneficial for organisms to communicate with each other through quorum sensing as well as transfer of genetic material. Biofilms are most commonly found attached to surfaces to which they cannot easily detach, such as medical devices and pipes in water systems. Biofilms can be beneficial or detrimental, depending on where they form and their inhabitants. For example, environmental biofilms are essential in the operation of wastewater treatment facilities. On the other hand, medical biofilms are the major cause of infections and persistent diseases. Biofilms consist of a variety of microbial species and strains in close proximity to one another; the presence of a resistant strains can lead to resistance in previously susceptible species. Antibiotic resistance in bacterial biofilms has led to investigations into novel compounds and combination therapies to combat infections and restore susceptibility. Antipathogenic compounds are one category of chemicals that act as effective antibiotic adjuvants. Accordingly, in one aspect, disclosed herein are methods of preventing, inhibiting, and/or reducing biofilm formation as well as methods of reducing, treating, and/or destroying a biofilm.

Anti-pathogenic therapeutics are compounds that target pathogen virulence mechanisms while minimizing bactericidal activity. Anti-pathogenic compounds have gained attention in recent years because they apply less selective pressure against microbial pathogens than bactericidal agents and so may delay the development of antibiotic resistance. Anti-pathogenic compounds may be a useful co-therapeutic agents to enhance the effects of antibiotics on biofilms. Combination therapeutics such as this are attractive therapeutics in an age of emerging antibiotic resistance.

*Rhamnus prinoides* is a plant that belongs family rhamnaceae. *R. prinoides* known as gesho was found in Ethiopia and has been widely cultivated. It was also found in Africa in the south countries like Kenya. The plant has an edible fruit and has been used for many medicinal treatments such as infectious diseases. It is known for its ethnomedicinal uses and its parts were used to treat nose, ear and throat infections in Kenya while the leaves are used for tonsillitis in Ethiopia. In addition, gesho has been used in different case of scabies, dandruff and hepatitis. Its decoction was used to treat stomach pain and was used in rheumatism and pneumonia as well. Its root extract was used for rheumatism and gonorrhea. Gesho has been studied for its antimicrobial activities and showed positive results that encouraged its study against diseases.

It is understood and herein contemplated that extract from the leaves, root and/or stem of gesho can inhibit biofilm formation and/or disrupt biofilm. As shown herein, there are various small molecules that have been identified in gesho extract and have an inhibitory effect on biofilm formation. In particular, 4-ethoxy benzoic acid (4EB), ethyl 4-ethoxybenzoate (EEB), gallic acid, methyl gallate, methyl paraben, 4-hydroxy-4-methylpentanone (HMP), adipic acid, phytol, or phytol acetate are chemicals that were identified in gesho extract. As shown herein EEB and HMP have an inhibitory effect on biofilm formation and have the ability to disrupt biofilm. Additionally, looking at the structure of EEB, methyl paraben, salicyclic acid, 3-hydroxybenzoic acid, p-hydroxybenzoic acid, p-hydroxybenzoic acid methyl ester, pyrocatechuic acid, gentisic acid, protocatechuic acid, 4-ethoxy benzoic acid (4EB), ethyl 4-ethoxybenzoate (EEB), gallic acid, methyl gallate, ethyl gallate, and propyl gallate, 4were identified and tested for anti-biofilm activity. Among the other compounds that were screened, 2-decanol had an anti-biofilm effect that has not been previously published on or patented. Additionally, adipic acid is a compound of interest. Thus, in one aspect, disclosed herein are methods of methods of preventing, inhibiting, and/or reducing biofilm formation and methods of reducing, treating, and/or destroying a biofilm comprising contacting the biofilm with an extract from *Rhamnus prinoides* (gesho) extract, an isolated small molecule derivative of thereof (such as, for example, salicyclic acid, 3-hydroxybenzoic acid, p-hydroxybenzoic acid, p-hydroxybenzoic acid methyl ester, pyrocatechuic acid, gentisic acid, protocatechuic acid, 4EB, EEB, gallic acid, methyl gallate, ethyl gallate, propyl gallate, methyl paraben, HMP (also known as diacetone alcohol), adipic acid, phytol, or phytol acetate, 2-decanol). In one aspect, the biofilm can be in a subject; thus, also disclosed herein are methods of preventing, inhibiting, and/or reducing biofilm formation and methods of reducing, treating, and/or destroying a biofilm in a subject comprising administering to the subject a composition comprising a therapeutically effective amount of an extract from *Rhamnus prinoides* (gesho), an isolated small molecule derivative of thereof, 2-decanol, or methyl paraben.

Due to gesho extracts low toxicity, it is understood and herein contemplated that the disclosed compositions comprising a gesho extract, an isolated small molecule derivative of thereof (such as, for example, salicyclic acid, 3-hydroxybenzoic acid, p-hydroxybenzoic acid, p-hydroxybenzoic acid methyl ester, pyrocatechuic acid, gentisic acid, protocatechuic acid, 4EB, EEB, gallic acid, methyl gallate, ethyl gallate, propyl gallate, methyl paraben, HMP (also known as diacetone alcohol), adipic acid, phytol, or phytol acetate) or 2-decanol can be used as a sanitizer or as a component in a sanitizer for use on surfaces susceptible to the development of biofilms. Moreover, the disclosed compositions comprising an extract from *Rhamnus prinoides* (gesho), an isolated small molecule derivative of thereof ((such as, for example, salicyclic acid, 3-hydroxybenzoic acid, p-hydroxybenzoic acid, p-hydroxybenzoic acid methyl ester, pyrocatechuic acid, gentisic acid, protocatechuic acid, 4EB, EEB, gallic acid, methyl gallate, ethyl gallate, propyl gallate, methyl paraben, HMP (also known as diacetone alcohol), adipic acid, phytol, or phytol acetate), or 2-decanol can be used to enhance the sensitivity of a biofilm or microbial organism that can form a biofilm (such as, for example, a Gram positive microbial organism (such as, for example, *Staphylococcus aureus*, *Streptococcus mutans*, *Listeria monocytogenes*, or *Bacillus subtilis*), a Gram negative organism including *Pseudomonas aeruginosa*, and/or a eurkaryotic organism (such as, for example *Candida albicans* or *Malassezia globosa*) to an antibiotic. Accordingly, in one aspect, disclosed herein are methods of enhancing the sensitivity of a biofilm to an antibiotic comprising contacting the biofilm with an extract from *Rhamnus prinoides* (gesho), an isolated small molecule derivative of thereof (such as, for example, salicyclic acid, 3-hydroxybenzoic acid, p-hydroxybenzoic acid, p-hydroxybenzoic acid methyl ester, pyrocatechuic acid, gentisic acid, protocatechuic acid, 4EB, EEB, gallic acid, methyl gallate, ethyl gallate, propyl gallate, methyl paraben, HMP (also known as diacetone alcohol), adipic acid, phytol, or phytol acetate), or 2-decanol and an antimicrobial agent including, but not limited to Abacavir, Acyclovir, Adefovir, Amantadine, Amprenavir, Ampligen, Arbidol, Atazanavir, Atripla, Balavir, Cidofovir, Combivir, Dolutegravir, Darunavir, Delavirdine, Didanosine, Docosanol, Edoxudine, Efavirenz, Emtricitabine, Enfuvirtide, Entecavir, Ecoliever, Famciclovir, Fomivirsen, Fosamprenavir, Foscarnet, Fosfonet, Ganciclovir, Ibacitabine, Imunovir, Idoxuridine, Imiquimod, Indinavir, Inosine, Lamivudine, Lopinavir, Loviride, Maraviroc, Moroxydine, Methisazone, Nelfinavir, Nevirapine, Nexavir, Nitazoxanide, Norvir, Oseltamivir, Peginterferon alfa-2a, Penciclovir, Peramivir, Pleconaril, Podophyllotoxin, Raltegravir, Ribavirin, Rimantadine, Ritonavir, Pyramidine, Saquinavir, Sofosbuvir, Stavudine, Telaprevir, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Zalcitabine, Zanamivir, Zidovudine, Clofazimine; Dapsone; Capreomycin; Cycloserine; Ethambutol (Bs); Ethionamide; Isoniazid; Pyrazinamide; Rifampicin; Rifabutin; Rifapentine; Streptomycin; Arsphenamine; Chloramphenicol (Bs); Fosfomycin; Fusidic acid; Metronidazole; Mupirocin; Platensimycin; Quinupristin/Dalfopristin; Thiamphenicol; Tigecycline (Bs); Tinidazole; Trimethoprim (Bs); aminoglycosides such as, for example, Amikacin, Gentamicin, Kanamycin, Meropenem, Neomycin, Netilmicin, Tobramycin, Paromomycin, Streptomycin, Spectinomycin, Nitazoxanide, Melarsoprol Eflornithine, Metronidazole, Tinidazole, Miltefosine, Mebendazole, Pyrantel pamoate, Thiabendazole, Diethylcarbamazine, Ivermectin, Niclosamide, Praziquantel, Albendazole, Praziquantel, Rifampin, Amphotericin B, Fumagillin, Amphotericin B, Candicidin, Filipin, Hamycin, Natamycin, Nystatin, Rimocidin, Bifonazole, Butoconazole, Clotrimazole, Econazole, Fenticonazole, Isoconazole, Ketoconazole, Luliconazole, Miconazole, Omoconazole, Oxiconazole, Sertaconazole, Sulconazole, Tioconazole, Albaconazole, Efinaconazole, Epoxiconazole, Fluconazole, Isavuconazole, Itraconazole, Posaconazole, Propiconazole, Ravuconazole, Terconazole, Voriconazole, Abafungin, Anidulafungin, Caspofungin, Micafungin, Aurones, Benzoic acid, Ciclopirox, Flucytosine, Griseofulvin, Haloprogin, Tolnaftate, Undecylenic acid, Crystal violet, Balsam of Peru, Orotomide, Miltefosine; ansamycins, such as, for example, geldanamycin, rifaximin, herbimycin; Carbapenems, such as, for example, Ertapenem, Doripenem, Imipenem/Cilastatin, and Meropenem; Cephalosporins, such as, for example, Cefadroxil, Cefazolin, Cephradine, Cephapirin, Cephalothin, Cefalexin, Cefaclor, Cefoxitin, Cefotetan, Cefamandole, Cefmetazole, Cefonicid, Loracarbef, Cefprozil, Cefuroxime, Cefixime, Cefdinir, Cefditoren, Cefoperazone, Cefotaxime, Cefpodoxime, Ceftazidime, Ceftibuten, Ceftizoxime, Moxalactam, Ceftriaxone, Cefepime, Ceftaroline fosamil, and Ceftobiprole; Glycopeptides, such as, for example Teicoplanin, Vancomycin, Telavancin, Dalbavancin, and Oritavancin; Lincosamides (Bs), such as, for example, Clindamycin and Lincomycin; Lipopeptides, such as, for example, Daptomycin; Macrolides (Bs), such as, for example, Azithromycin, Clarithromycin, Erythromycin, Roxithromycin, Telithromycin, and Spiramycin; Monobactams, such as, for example, Aztreonam; Nitrofurans, such as, for example, Furazolidone and Nitrofurantoin (Bs); Oxazolidinones (Bs), such as, for example, Linezolid, Posizolid, Radezolid, and Torezolid; Penicillins, such as, for example, Amoxicillin, Ampicillin, Azlocillin, Dicloxacillin, Flucloxacillin, Mezlocillin, Methicillin, Nafcillin, Oxacillin, Penicillin G, Penicillin V, Piperacillin, Penicillin G, Temocillin, and Ticarcillin; Polypeptides, such as, for example, Bacitracin, Colistin, and Polymyxin B; Quinolones/Fluoroquinolones, such as, for example, Ciprofloxacin, Enoxacin, Gatifloxacin, Gemifloxacin, Levofloxacin, Lomefloxacin, Moxifloxacin, Nadifloxacin, Nalidixic acid, Norfloxacin, Ofloxacin, Trovafloxacin, Grepafloxacin, Sparfloxacin, and Temafloxacin; Sulfonamides (Bs), such as, for example, Mafenide, Sulfacetamide, Sulfadiazine, Silver sulfadiazine, Sulfadimethoxine, Sulfamethizole, Sulfamethoxazole, Sulfanilimide (archaic), Sulfasalazine, Sulfisoxazole, Trimethoprim-Sulfamethoxazole (Co-trimoxazole) (TMP-SMX), and Sulfonamidochrysoidine (archaic); Tetracyclines (Bs), such as, for example, Demeclocycline, Doxycycline, Metacycline, Minocycline, Oxytetracycline, and Tetracycline; monoclonal antibodies such as, for example, Actoxumab, Atidortoxumab, Berlimatoxumab, Bezlotoxumab, Cosfroviximab, Edobacomab, Felvizumab, Firivumab, Foravirumab, Larcaviximab, Motavizumab, Navivumab, Panobacumab, Palivizumab, Porgaviximab, CR6261, Rafivirumab, Pagibaximab, Obiltoxaximab, Ibalizumab, Regavirumab, Rmab, Sevirumab, Rivabazumab pegol, Tefibazumab, Suvratoxumab, and Tuvirumab; and checkpoint inhibitors; Pembrolizumab, Nivolumab, Atezolizumab, Avelumab, Durvalumab, pidilizumab, AMP-224, AMP-514, PDR001, cemiplimab, and Ipilimumab.

Biofilm communities are how bacteria survive in different environments, their ability to overcome stressful conditions increased their persistence and made them a major cause of nosocomial infections, 50% of nosocomial infections are related to indwelling devices such as catheters, dentures and heart valves. Biofilms comprised of pathogens can cause chronic infections. Cystic fibrosis, pneumonia, device associated infections, and chronic wound infections are the most common disease caused by biofilms that can lead to several deaths cases. The severity of infections caused by biofilms and their ability to be chronic is due to their high resistance to antibiotics and their ability to resist and evade the immune system. Accordingly, in one aspect, disclosed herein are methods of treating cystic fibrosis, pneumonia, chronic wound infections, or device associated infections in a subject comprising administering to the subject an extract from *Rhamnus prinoides* (gesho), an isolated small molecule derivative of thereof (such as, for example, salicyclic acid, 3-hydroxybenzoic acid, p-hydroxybenzoic acid, p-hydroxybenzoic acid methyl ester, pyrocatechuic acid, gentisic acid, protocatechuic acid, 4EB, EEB, gallic acid, methyl gallate, ethyl gallate, propyl gallate, methyl paraben, HMP (also known as diacetone alcohol), adipic acid, phytol, or phytol acetate), or 2-decanol.

It is understood and herein contemplated that biofilms are often comprised of multiple species and are referred to as polymicrobial biofilms and can include both prokaryotic and eukaryotic microorganisms. The human body being complex, harboring the human microbiota including bacteria, fungi and archaea lead to the presence of polymicrobial biofilms that has become the more common feature of pathogenic biofilms. Polymicrobial biofilms display a complex environment that can be altered by various changes of host such as immunity. Polymicrobial communities help biofilms become more antibiotic resistant through passive mechanisms; for example, where one organism uses the other's resistance capabilities to protect itself, a concept referred to as indirect pathogenicity. Moreover, members of polymicrobial biofilms enhance their quorum sensing communication as well as increase their metabolic products and the genetic pool where they have access to wider variety and more diverse resources. It has been demonstrated that polymicrobial biofilms were not only formed from multiple bacterial species, but eukaryotic pathogens were involved as well. This emphasizes the importance and necessity for increasing attention towards these biofilms and focus on their essential role in chronic infections.

For example, *Streptococcus mutans* is a primary cause of dental carries (i.e., tooth decay), due to its ability to form biofilms in the oral cavity tissue. *S. mutans* produces adhesins that helps it to bind to the tooth surface as well as other proteins that help in its biofilm formation *S. mutans* biofilm formation mechanisms can be sucrose dependent or independent. The ability of *S. mutans* to form robust biofilms lies in the secretion of an exoenzyme called glucosyltransferase. Through this exoenzyme, *S. mutans* utilizes sucrose supplied from food to produce Extra polysaccharide matrix (EPS). Moreover, *S. mutans* has the ability to overcome stressful and highly acidic environments, enabling it to survive and form biofilms leading to dental carries.

*Candida albicans* represent the most common human fungal pathogen that can form biofilms. According to in vitro studies *Candida* forms biofilms in several stages. It starts with an early phase, where it goes through morphogenesis after adhering to a suitable surface. Formation of hyphae at this stage is essential for *Candida* to form biofilms. The second stage is the intermediate stage where hyphae continue their growth with the production of the extracellular matrix. Finally, the third stage is maturation where the yeast forms are present at the base with the hyphae at the surface of the biofilm and embedded in the polysaccharide matrix. *Candida* infection can be fatal, and studies are focused on their formation on abiotic and biotic surfaces, for example catheters and oral cavity.

*Candida* species were found to be the main pathogen causing infection for denture users leading to denture stomatitis. *Candida albicans* were found to be the most common among the *Candida* species. *C. albicans* can grow in different morphological forms as yeast or pseudohyphae or true hyphae. The elongated hyphae form has been observed to help the yeast penetrate into tissue by escaping from phagocytic cells. The ability of *C. albicans* to form biofilms through interaction with surfaces and formation of extracellular matrix is dependent on its ability to form hyphae.

Fungal and bacterial cooperation in biofilm formation synergizes biofilm activity and growth. They collaborate with each other to exchange metabolites or growth factors. For example, *S. mutans* metabolizes sucrose to glucose and fructose which can be a benefit for *C. albicans*.

*Candida albicans* or *Candida* species were found to be the main pathogen causing infection for denture users leading to denture stomatitis, bacteria were also found to be a factor in biofilm formation in dentures. Another example of fungal-bacterial association in biofilms is in the early-childhood caries (ECC). *Streptococcus mutans* is a main bacterial pathogen for dental caries, especially in early-childhood caries (ECC). It was found that *S. mutans* is not solely present but *Candida albicans* were common in cases of highly infected plaque biofilms with *S. mutans* in children with ECC. *S. mutans* and *C. albicans* biofilms are enhanced by increase of exopolysaccharides by *C. albicans* and hence increasing the biomass. When animals were coinfected, biofilm virulence was synergized. In vitro studies shows that glucosyltransferase EPS derived was a main mediator in development of the dual specious biofilms and that *C. albicans* enhance the virulence genes expression in *S. mutans*.

Accordingly, in one aspect, disclosed herein are methods of preventing, inhibiting, and/or reducing biofilm formation and methods of reducing, treating, and/or destroying a biofilm wherein the biofilm comprises one or more microbial organisms. In one aspect, the microbial organism can be a Gram positive bacteria (such as, for example, *Staphylococcus aureus, Streptococcus mutans, Listeria monocytogenes*, or *Bacillus subtilis*) or Gram negative bacteria (such as, for example, *Pseudomonas aeruginosa*). It is further understood that the microbial organisms of the biofilm can be a eukaryotic organism such as *Candida albicans*. It is understood and herein contemplated that the biofilms associated with the disclosed methods of prevention or methods of treating can comprise only a single species of prokaryotic or eukaryotic microbial organism, multiple species or prokaryotic or eukaryotic organisms, or one or more species of both prokaryotic and eukaryotic organism.

In one aspect, it is understood and herein contemplated that the disclosed compositions comprising a gesho extract, an isolated small molecule derivative of thereof (such as, for example, benzoic acid derivatives or gallic acid derivatives including alkylated, carboxylated, alkoxylated, hydroxylated and acetylated compounds, including, but not limited to, salicyclic acid, 3-hydroxybenzoic acid, p-hydroxybenzoic acid, p-hydroxybenzoic acid methyl ester, pyrocatechuic acid, gentisic acid, protocatechuic acid, 4-ethoxy benzoic acid (4EB), ethyl 4-ethoxybenzoate (EEB), gallic acid, methyl gallate, ethyl gallate, propyl gallate), 4-hydroxy-4-methylpentanone (HMP), adipic acid, phytol, methyl paraben, phytol acetate or 2-decanol while able to inhibit, reduce, prevent, or treat a biofilm or biofilm formation, said extracts are equally effective in reducing the presence of a microbe (such as, for example, a Gram positive microbial organism (such as, for example, *Staphylococcus aureus, Streptococcus mutans, Listeria monocytogenes*, or *Bacillus subtilis*), a Gram negative organism including *Pseudomonas aeruginosa*, and/or a eurkaryotic organism (such as, for example *Candida albicans* or *Malassezia globosa*) in a subject or on a surface. Accordingly, in one aspect, disclosed herein are methods of inhibiting, reducing, preventing, and/or killing a microbial organism (such as, for example, a Gram positive microbial organism (such as, for example, *Staphylococcus aureus, Streptococcus mutans, Listeria monocytogenes*, or *Bacillus subtilis*), a Gram negative organism including *Pseudomonas aeruginosa*, and/or a eurkaryotic organism (such as, for example *Candida albicans* or *Malassezia globosa*) in a subject or on a surface comprising administering a subject infected with a microbial organism causing a biofilm or contact a biofilm on a surface with a therapeutically effective amount of an extract from

*Rhamnus prinoides* (gesho), an isolated small molecule derivative of thereof, 2-decanol, or methyl paraben.

In one aspect, it is understood that given the effectiveness of the disclosed gesho extracts, isolated small molecule derivatives of thereof (such as, for example, salicyclic acid, 3-hydroxybenzoic acid, p-hydroxybenzoic acid, p-hydroxybenzoic acid methyl ester, pyrocatechuic acid, gentisic acid, protocatechuic acid, 4EB, EEB, gallic acid, methyl gallate, ethyl gallate, propyl gallate, methyl paraben, HMP (also known as diacetone alcohol), adipic acid, phytol, or phytol acetate), or 2-decanol to act as a disinfectant, microbicide, bactericide, and/or sanitizer, said gesho extracts, isolated small molecule derivatives of thereof, or 2-decanol can be used alone or as an active component in a surface cleaner, disinfectant, sanitizer, mouth rinse, paint, caulk, adhesive, shampoo, and/or body wash. Accordingly, disclosed herein are surface cleaners, disinfectants, sanitizers, mouth rinses, paints, caulks, adhesives, shampoos, and/or body washes comprising any of the gesho extracts, isolated small molecule derivatives of thereof (such as, for example, benzoic acid derivatives or gallic acid derivatives including alkylated, carboxylated, alkoxylated, hydroxylated and acetylated compounds, including, but not limited to, salicyclic acid, 3-hydroxybenzoic acid, p-hydroxybenzoic acid, p-hydroxybenzoic acid methyl ester, pyrocatechuic acid, gentisic acid, protocatechuic acid, 4-ethoxy benzoic acid (4EB), ethyl 4-ethoxybenzoate (EEB), gallic acid, methyl gallate, ethyl gallate, propyl gallate), 4-hydroxy-4-methylpentanone (HMP), adipic acid, phytol, methyl paraben, phytol acetate or 2-decanol disclosed herein in an amount effective to reduce, inhibit, or treat microbial organisms and/or biofilm formation.

Additionally, the gesho extracts, isolated small molecule derivatives of thereof (such as, for example, benzoic acid derivatives or gallic acid derivatives including alkylated, carboxylated, alkoxylated, hydroxylated and acetylated compounds, including, but not limited to, salicyclic acid, 3-hydroxybenzoic acid, p-hydroxybenzoic acid, p-hydroxybenzoic acid methyl ester, pyrocatechuic acid, gentisic acid, protocatechuic acid, 4-ethoxy benzoic acid (4EB), ethyl 4-ethoxybenzoate (EEB), gallic acid, methyl gallate, ethyl gallate, propyl gallate), 4-hydroxy-4-methylpentanone (HMP), adipic acid, phytol, methyl paraben, phytol acetate or 2-decanol disclosed herein can be used to treat, inhibit, reduce, or prevent microbial infection or biofilm formation or a biofilm at a site of a wound, rash, abrasion, cut, surgical incision, or implant. Thus, it is understood and herein contemplated that the disclosed gesho extracts, isolated small molecule derivatives of thereof (such as, for example, benzoic acid derivatives or gallic acid derivatives including alkylated, carboxylated, alkoxylated, hydroxylated and acetylated compounds, including, but not limited to, salicyclic acid, 3-hydroxybenzoic acid, p-hydroxybenzoic acid, p-hydroxybenzoic acid methyl ester, pyrocatechuic acid, gentisic acid, protocatechuic acid, 4-ethoxy benzoic acid (4EB), ethyl 4-ethoxybenzoate (EEB), gallic acid, methyl gallate, ethyl gallate, propyl gallate), 4-hydroxy-4-methylpentanone (HMP), adipic acid, phytol, methyl paraben, phytol acetate or 2-decanol can be used as a medicated component of sponges, scaffolds, stents, matrixes, grafts, bandages (including adhesive bandages), wound dressings, surgical drapes, sutures, staples, surgical adhesives, salves, creams, or wound adhesives to reduce, inhibit, prevent, or treat a biofilm, biofilm formation, or a microbial infection. Thus, in one aspect, disclosed herein are sponges, scaffolds, stents, matrixes, grafts, bandages (including adhesive bandages), wound dressings, surgical drapes, sutures, staples, surgical adhesives, salves, creams, or wound adhesives comprising a therapeutically effective amount any of the gesho extracts, isolated small molecule derivatives of thereof (such as, for example, benzoic acid derivatives or gallic acid derivatives including alkylated, carboxylated, alkoxylated, hydroxylated and acetylated compounds, including, but not limited to, salicyclic acid, 3-hydroxybenzoic acid, p-hydroxybenzoic acid, p-hydroxybenzoic acid methyl ester, pyrocatechuic acid, gentisic acid, protocatechuic acid, 4-ethoxy benzoic acid (4EB), ethyl 4-ethoxybenzoate (EEB), gallic acid, methyl gallate, ethyl gallate, propyl gallate), 4-hydroxy-4-methylpentanone (HMP), adipic acid, phytol, methyl paraben, phytol acetate or 2-decanol disclosed herein.

Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J.*

Cancer, 58:700-703, (1988); Senter, et al., *Bioconjugate Chem.*, 4:3-9, (1993); Battelli, et al., *Cancer Immunol. Immunother.*, 35:421-425, (1992); Pietersz and Mckenzie, *Immunolog. Reviews*, 129:57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, PA 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines. Accordingly, disclosed herein are compositions comprising a pharmaceutical carrier and a therapeutically effective amount of gesho extract or isolated small molecule therefrom (such as, for example, benzoic acid derivatives or gallic acid derivatives including alkylated, carboxylated, alkoxylated, hydroxylated and acetylated compounds, including, but not limited to, salicyclic acid, 3-hydroxybenzoic acid, p-hydroxybenzoic acid, p-hydroxybenzoic acid methyl ester, pyrocatechuic acid, gentisic acid, protocatechuic acid, 4-ethoxy benzoic acid (4EB), ethyl 4-ethoxybenzoate (EEB), gallic acid, methyl gallate, ethyl gallate, propyl gallate), 4-hydroxy-4-methylpentanone (HMP), adipic acid, phytol, methyl paraben, phytol acetate or 2-decanol.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter indications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

Biofilm treatment has been very difficult and the most effective method is removal of infected area such as the implant or the organ if possible, but in cases where that is not possible the main approaches are by combined antibiotic intake before the biofilm formation or by chronic intake of antibiotics in case the biofilm has already been formed.

In one aspect, it is understood and herein contemplated that polymicrobial biofilms can cause or be associated with disease (such as, for example, tooth decay, cystic fibrosis, pneumonia, device associated infection, and chronic wound infections) and have resistance to antibiotics. Several features of polymicrobial biofilms contribute to their enhanced antibiotic resistance. One important factor is the polymeric matrix surrounding the microorganisms, which acts as a protective shield against both the immune system of the host and antimicrobial medications. Prolonged treatment with various antibiotics can cause resistance through exposure to selective pressure, in addition it allows biofilm bacteria to adapt and acquire resistance through horizontal gene transfer. Other mechanisms have been suggested for biofilm antimicrobial tolerance such as the phenotypic heterogenicity of cells within the biofilm which is directly related to unequal susceptibility to antimicrobial effects.

Several methods have been under trials in effort to develop biofilm treatments. Among those methods are coating devices with antimicrobial agents to prevent the attachment of organisms to their surfaces and hinder their growth into biofilms. Other methods include quorum sensing inhibitors, bacteriophage therapy, oral drug combinations and new antimicrobial agents. Quorum sensing inhibitors proved to have significant antibiofilm effects but the need for further research on their safety as well as the debate on their inability to kill cells and only inhibiting their virulence has stood in the way of their emergence. Bacteriophage therapy concentrate on targeting bacteriophage to bacterial biofilms and thus removing the biofilm. Bacteriophage therapy is one of the recently studied mechanisms due to their safety and cost-effective production. Oral drug combination including quorum sensing inhibitors, enzymes, antifungals, herbs and antimicrobial agents have been investigated but the safety of such treatment is yet to be confirmed. Finally development of antimicrobial such as tigecycline have been under study for their biocidal effects on biofilm associated bacteria with promising effects.

It is understood and herein contemplated that the disclosed compositions comprising *Rhamnus prinoides* (gesho), an isolated small molecule derivative of thereof, 2-decanol, or methyl paraben which can prevent biofilm formation, reduce virulence factors of the microbes in the biofilm, and/or disrupt the biofilm can have a therapeutic effect on a subject comprising a disease associated with a biofilm. This can be in part due to a reduction in evolutionary pressure placed on the bacteria by the host environment upon contact with the gesho extract or isolated small molecule therefrom (such as, for example, salicyclic acid, 3-hydroxybenzoic acid, p-hydroxybenzoic acid, p-hydroxybenzoic acid methyl ester, pyrocatechuic acid, gentisic acid, protocatechuic acid, 4EB, EEB, gallic acid, methyl gallate, ethyl gallate, propyl gallate, methyl paraben, HMP (also known as diacetone alcohol), adipic acid, phytol, or phytol acetate), 2-decanol, or methyl paraben. It can also be as a result of the gesho extract or isolated small molecule therefrom (such as, for example, benzoic acid derivatives or gallic acid derivatives including alkylated, carboxylated, alkoxylated, hydroxylated and acetylated compounds, including, but not limited to, salicyclic acid, 3-hydroxybenzoic acid, p-hydroxybenzoic acid, p-hydroxybenzoic acid methyl ester, pyrocatechuic acid, gentisic acid, protocatechuic acid, 4-ethoxy benzoic acid (4EB), ethyl 4-ethoxybenzoate (EEB), gallic acid, methyl gallate, ethyl gallate, propyl gallate), 4-hydroxy-4-methylpentanone (HMP), adipic acid, phytol, methyl paraben, phytol acetate or 2-decanol inhibiting the microbes ability to adapt to the host environment or making it susceptible to the host immune system. Thus, in one aspect, disclosed herein are methods of treating a disease associated with biofilm formation in a subject comprising administering to the subject a composition comprising a therapeutically effective amount of an extract from *Rhamnus prinoides* (gesho or isolated small molecule therefrom (such as, for example, salicyclic acid, 3-hydroxybenzoic acid, p-hydroxybenzoic acid, p-hydroxybenzoic acid methyl ester, pyrocatechuic acid, gentisic acid, protocatechuic acid, 4EB, EEB, gallic acid, methyl gallate, ethyl gallate, propyl gallate, methyl paraben, HMP (also known as diacetone alcohol), adipic acid, phytol, or phytol acetate), 2-decanol, or methyl paraben.

As noted above, biofilms can comprise one or more microbial organisms. Accordingly, in one aspect, disclosed herein are methods of treating a disease associated with biofilm formation wherein the biofilm comprises one or more microbial organisms. In one aspect, the microbial organism can be a Gram positive (such as, for example, *Staphylococcus aureus, Streptococcus mutans, Listeria monocytogenes*, or *Bacillus subtilis*). It is further understood that the microbial organisms of the biofilm can be a eukaryotic organism such as *Candida albicans* or *Malassezia globosa*. It is understood and herein contemplated that the biofilms associated with the disclosed methods of prevention or methods of treating can comprise only a single species of prokaryotic or eukaryotic microbial organism, multiple species or prokaryotic or eukaryotic organisms, or one or more species of both prokaryotic and eukaryotic organism.

In one aspect, it is understood and herein contemplated that the disclosed gesho extract or isolated small molecule therefrom (such as, for example, benzoic acid derivatives or gallic acid derivatives including alkylated, carboxylated, alkoxylated, hydroxylated and acetylated compounds, including, but not limited to, salicyclic acid, 3-hydroxybenzoic acid, p-hydroxybenzoic acid, p-hydroxybenzoic acid methyl ester, pyrocatechuic acid, gentisic acid, protocatechuic acid, 4-ethoxy benzoic acid (4EB), ethyl 4-ethoxybenzoate (EEB), gallic acid, methyl gallate, ethyl gallate, propyl gallate), 4-hydroxy-4-methylpentanone (HMP), adipic acid, phytol, methyl paraben, phytol acetate or 2-decanol can be further combined with any known antimicrobial in the art to treat a subject with a disease associated with a biofilm.

The term "therapeutically effective" refers to the amount of the composition used is of sufficient quantity to ameliorate one or more causes or symptoms of a disease or disorder. Such amelioration only requires a reduction or alteration, not necessarily elimination.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "inhibit" refers to a decrease in an activity, response, condition, disease, or other biological parameter. This can include but is not limited to the complete ablation of the activity, response, condition, or disease. This can also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

B. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Figures 1A, 1B, 1C, 1D:
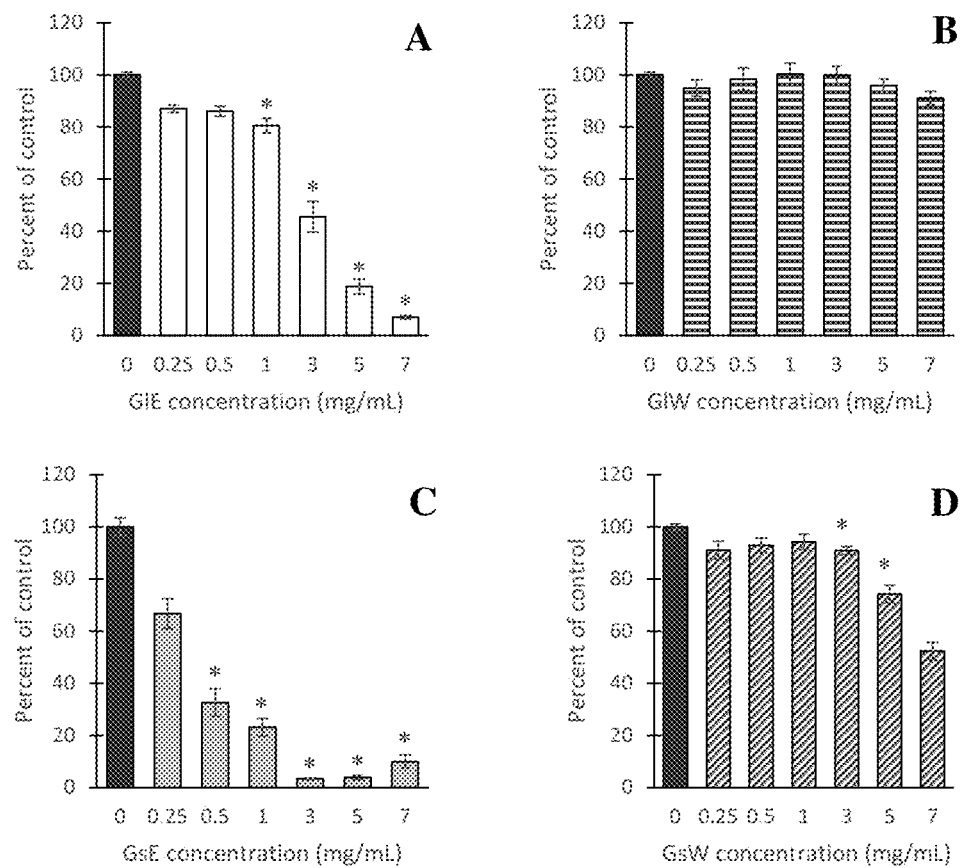
Figure 2:
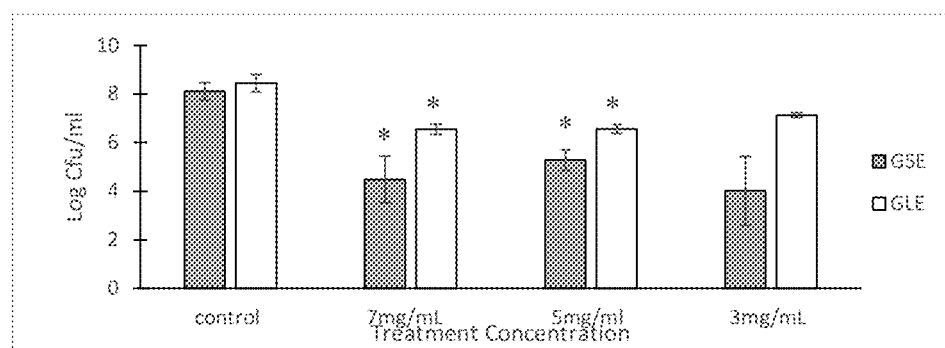
FIG. 2 shows a viability assay showing log reductions of *S. mutans* with gesho ethanol extracts. (*) indicates significant difference (p<0.05) between treated samples and the untreated control.
Figure 3:
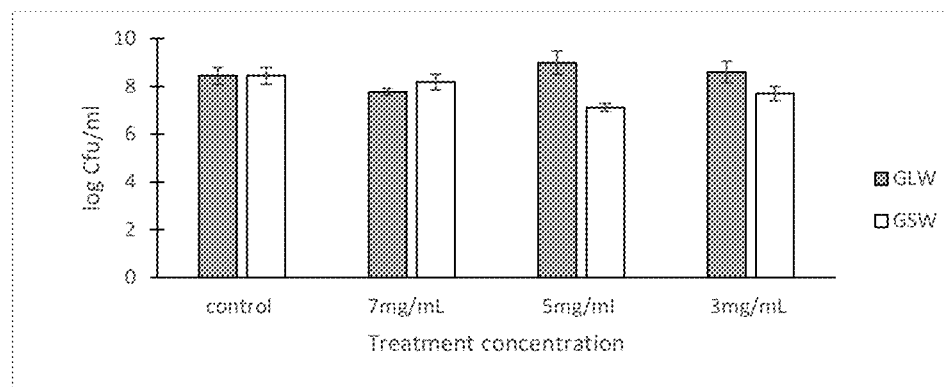
FIG. 3 shows a viability assay showing log reductions of *S. mutans* with gesho water extracts.

Example 1: *Rhamnus prinoides* (Gesho) Extract for the Inhibition of Polymicrobial Biofilm Formation a) Results
(1) Effects of Gesho Extracts on *S. mutans* Biofilm Formation Significant inhibition of biofilm formation for the gesho leaf ethanol (GLE) fraction with gradual increase in biofilm formation with the decrease in extract concentration. The most significant decrease in biofilms were at the 3, 5, and 7 mg/ml concentrations. The GLE 7 mg/ml showed 90% biofilm reduction, 5 mg/ml showed 80% biofilm reduction and 55% reduction for 3 mg/ml concentration. Gesho stem ethanol (GSE) assay resulted in similar effects as GLE with an average 90% biofilm reduction for the 3, 5 and 7 mg/ml concentrations. While for the Gesho stem water (GSW) 50%, 25% and 10% reductions were shown for the 7, 5 and 3 mg/ml, respectively. Gesho leaf water (GLW) had minor inhibitory effects with 10% and 5% reductions for the 5 and 7 mg/ml concentrations respectively. Each assay was repeated 3 times on independent occasions, results were consistent for each fraction concentrations and the average of the three assays were plotted as percent of control (FIG. 1, FIG. 2) *S. mutans* viability assays Viability assays for the *S. mutans* were carried on the 3, 5 and 7 mg/ml concentrations since they represent the concentrations with the most significant effects. When compared to control; GLE showed average 2 log reductions for the 7 mg/ml concentration, 2 log reductions for 5 mg/ml and 1.5 log reduction for 3 mg/ml. GSE showed an average 3 log reduction for the 7 mg/ml compared to its control, 2.5 log reduction for 5 mg/ml and 4 log reductions for 3 mg/ml. GSW and GLW showed minor insignificant log reductions for viability assays with the GSW showing lower reduction than the GLW. Each assay was repeated three times and an average was plotted revealing the stated results (FIGS. 3 and 4).

(2) Effects of Gesho Ethanol Extracts on *C. albicans* Biofilm Formation

Since the goal of this study is determination of gesho extract effects on polymicrobial biofilms work was conducted with the most effective extracts. From the *S. mutans* results gesho ethanol extracts had the significant effects. Hence, the biofilm formation assay was conducted for *C. albicans* only on the ethanol extracts of gesho. Results showed significant inhibition of biofilm formation for the GSE fraction with more consistent results than GLE. The decrease in biofilms was similar through most of the tested concentrations 0.5, 1, 3, 5 and 7 mg/ml. The GSE biofilm reduction ranged from 75-65% among those concentrations. GLE assay resulted in similar effects as GSE with an average 50% biofilm reduction for all concentrations, 0.25, 0.5, 1, 3, 5 and 7 mg/ml. Each assay was repeated 3 times on independent occasions and the average of the three assays were plotted as percent of control (FIG. 5 and FIG. 6).
(3) *C. albicans* Viability Assays Viability assays for *C. albicans* showed an increase to nonsignificant decrease in Log CFU/ml. GSE showed an increase of one log for 7 mg/ml, while the 5 and 3 mg/ml concentration showed a decrease of less than one log. While GLE showed an increase of around one Log for 3, 5 and 7 mg/ml concentrations (FIG. 7). Effects of GSE on *C. albicans* and *S. mutans* polymicrobial biofilms.

Gesho stem extract was chosen due to its more consistent results with *C. albicans*. GSE had similar inhibitory effects among most concentrations with *C. albicans* biofilms, while GSE 3 mg/ml was the lowest concentration with highest effect on *S. mutans* (FIG. 8). Therefore, GSE 3 mg/ml was selected to proceed with performing gesho biofilm assays on polymicrobial biofilms. The design of this assay was performed to compare between polymicrobial biofilms of *C. albicans* and *S. mutans* and their monomicrobial biofilm biomass. FIG. 9 shows the synergism that occurs in polymicrobial biofilms with more than double increase in biofilm biomass, almost 75%, compared to each organism alone. On the other hand, GSE treatment result showed significant decrease in biofilm formation when tested on the polymicrobial biofilm with even more inhibitory effects than each organism alone. Epi-fluorescent microscope images When comparing microscope images of *S. mutans-C. albicans* gesho treated dual species biofilm to untreated ones, the images indicated that gesho ethanol extracts significantly decreased the number of cells for both organisms without observing a prominent decrease in number for one over the other. *C. albicans* hyphae formation remains the same and is not affected. The EPS of the biofilms was extremely demolished, and only scattered cells of *C. albicans* and *S. mutans* (FIG. 10) were observe. The images for untreated biofilms show dense biofilms with thick layers of *C. albicans* and *S. mutans* (FIG. 11).

(4) Cell Size Measurements Results

For each image the size of *C. albicans* yeast cells, the *C. albicans* hyphae and *S. mutans* sizes were measured. Each image 3-4 measurement were taken, and an average of measurements was calculated and plotted into graph (FIG. 12). Non-treated polymicrobial biofilms were compared to GSE 3 mg/ml treated polymicrobial biofilms. A difference in size measurements especially with *C. albicans* hyphae size is observable, which can be an indication that gesho is affecting hyphae formation in *C. albicans*.

b) Discussion (1) Gesho Inhibits *S. mutans* and *C. albicans* Polymicrobial Biofilm Formation Gesho leaf extracts have demonstrated antibacterial activity specifically against Gram positive bacteria. In research provided herein, gesho also successfully caused inhibitory effects on Gram positive bacterial biofilms. In this study, gesho inhibited *C. albicans* biofilms and polymicrobial biofilms comprised of both *C. albicans* and *S. mutans*. To test the hypothesis, the effect of gesho extracts on each organism alone was investigated. Through the results it was confirm that gesho can inhibit the biofilm formation of each organism alone. GSE extracts were the most potent in inhibiting the biofilms of *S. mutans*, while for *C. albicans*, GSE and GLE had similar inhibitory effects, although they were more consistent with GSE. *C. albicans* biofilm formation inhibition percentages were similar GSE at different concentrations, while for *S. mutans* GSE showed the highest inhibition with 3 mg/ml. Therefore, when testing polymicrobial biofilms GSE at 3 mg/ml was chosen as the working concentration.

The biomass of the untreated dual species biofilms was compared to the biomass of *C. albican* and *S. mutans* single species biofilms. The results demonstrated a synergism that resulted in a 70% biomass increase for the *C. albicans* and *S. mutans* dual species biofilm. *C. albicans* enhances the production of glycosyltransferase enzymes in *S. mutans*. Glycosyltransferase enzymes transfer sucrose to glucans, a major component of the EPS, strengthening the *S. mutans* component of the dual species biofilm and hence the overall biomass. Gesho stem extracts displayed significant inhibition of *C. albicans* and *S. mutans* dual species biofilm with GSE 3 mg/ml, even with the synergism gained with the association of the two organisms together. The present study started by testing the leaf and stem extracts separately. The stem extracts had a strong inhibitory effect. Moreover, using gesho as a natural remedy for polymicrobial biofilms formation was a focus. Few studies focused on natural treatments for polymicrobial biofilms, one similar study examined the antimicrobial effects of rosemary, a Mediterranean woody plant, for inhibiting polymicrobial biofilms.

(2) GSE Extracts: Potential Mechanisms

*S. mutans* being a prokaryote and *C. albicans* a eukaryote, the mechanism by which gesho extracts inhibit biofilm formation for each organism is assumed to be different. The viability assay results for *S. mutans* revealed significant log reductions compared to untreated controls, indicating that gesho ethanol extracts possess biocidal effects, inhibiting biofilm formation. On the other hand, *C. albicans* viability assays showed an increase in *C. albicans* growth. An increase or no notable change of CFU/mL was observed in the treated samples compared to the untreated samples. Thus, gesho ethanol extracts do not kill *C. albicans* cells, but they can be quorum sensing inhibitors, inhibiting biofilm formation.

Images of *C. albicans* and *S. mutans* dual species biofilms assisted in exploring the mechanism by which gesho ethanol extract act. Based on the finding that GSE effected *S. mutans* biofilms by 90% compared to 70% for *C. albicans*, the initial hypothesis was that the images would display a lower *S. mutans* biofilms biomass compared to *C. albicans* biofilm biomass. Contradictory to the hypothesis, the images displayed a proportionate reduction in number for both organisms, with no significant reduction of one organism over the other. The second hypothesis was related to a model where gesho bactericidal effects on *S. mutans* can compromise its ability to produce glucans for EPS formation and hence *C. albicans* biofilm formation is affected as well. The images show a significant decrease in the EPS of the dual species biofilms, which indicates that gesho can be acting on the exopolysaccharide matrix formation.

(3) Molecular Analysis (a) *S. mutans* Molecular Analysis

Molecular analysis for genes involved in biofilm formation can enhance knowledge on how gesho works. Each organism has its own genes involved in the biofilm construction process. In polymicrobial biofilms one organism can influence the gene expression of another. *C. albicans* increases the expression of glycosyltransferase genes (gtfB, gtfC), enhancing the EPS matrix formation. This model emphasizes the essential role of the gtf genes in biofilm formation for *S. mutans*. Image analysis indicated a significant reduction in polysaccharide matrix formation in the treated polymicrobial biofilms. This observation is in agreement with the reduction of gtf expression by gesho extract.

(b) *C. albicans* Molecular Analysis

Through the biofilm assays, it was confirmed that gesho ethanol extracts have the ability to inhibit biofilm formation for the dual species biofilms of *C. albicans* and *S. mutans* as well as their corresponding single species biofilms. Through the images, it was shown that both organism's ability to form biofilms is similarly compromised and the EPS biomass is significantly reduced.

C) Materials and Methods
(1) Microbial Strains and Culture Conditions

Two species of microorganism were used in this work: *Streptococcus mutans* and *Candida albicans* 30. *Streptococcus mutans* was a gift from Margaret Gould-Bartlett, Georgia State University and *Candida albicans* 30 was a gift from the lab of Sidney Crow, Georgia State University. *Streptococcus mutans* overnight cultures were cultivated in brain-heart infusion (BHI) (Becton, Dickinson, USA) broth while biofilms were formed in brain-heart infusion broth supplemented with 0.5% sucrose. *Candida albicans* overnight cultures were grow in yeast, peptone dextrose (YPD) broth while biofilms were formed in 1× RPMI 1640 with L-glutamine (Corning, USA) supplemented with 165 mM morpholinepropanesulfonic acid (MOPS).

(2) Biofilm Formation Assays (a) *S. mutans* Biofilms

Formation of in vitro biofilms was done in a 96-well microtiter plate, using 0.5% sucrose to assist *S. mutans* in biofilm formation. Biofilms were grown overnight at 37° C. aerobically on shaker. The biofilm assay was done using brain heart infusion (BHI) broth media for growth of *S. mutans*. *S. mutans* were cultured from −80° C. stocks in BHI broth and culture was grown overnight at 37° C. The following day, the culture concentration was measured at OD 600 and adjusted to 0.01 to be used in biofilm assay. BHI-sucrose media was used for biofilm assay, the BHI-sucrose was filter sterilized before adding *S. mutans* and proceeding with the assay. Gesho extracts were prepared at assigned concentrations and added to 96-well (100 μL per well) and the plate was set for overnight incubation at 37° C. on shaker. The next day, the 96-well plates were washed and stained by crystal violet. Than using 95% ethanol, biofilms were de-stained to measure absorbance using MD plate reader at an optical density (OD) of 595 nm. The experiment was repeated at least three times independently.

(b) *C. albicans* Biofilms

*C. albicans* were grown on a 96-well plate with slight difference, using $1\times10^7$ cells instead of $1\times10^6$ cells by using hemocytometer cell counting and calculation. When using hemocytometer, *C. albicans* was stained by 0.1% v/v methylene blue. *C. albicans* was cultured on yeast peptone dextrose (YPD) agar plate overnight at 37° C. form −80 stock. Then a loopful of colonies were cultured in 25 ml of YPD broth for 14-16 hours at 30° C. were *C. albicans* grows as budding yeast. Then *C. albicans* cells were centrifuged and washed twice with PBS and adjusted to $1\times10^7$ cells using hemocytometer. For biofilm formation in 96-well plates, cells were added to RPMI buffered with 165 mM morpholinepropanesulfonic acid (MOPS). The RPMI-MOPS were filter sterilized before *C. albicans* addition. Once *C. albicans* was added to RPMI-MOPS, gesho extracts were prepared at different concentration of 7, 5, 3, 1, 0.5. 0.25 mg/ml to test its biofilm inhibition effect on *C. albicans* biofilms. Only GSE and GLE were tested with *C. albicans*. Biofilms were stained by crystal violet after washing the plates than measure absorbance by MD plate reader at OD 595.

(c) Dual Species Biofilm

The in-vitro growth of the polymicrobial biofilms were done similar to but with some changes. Biofilms of *S. mutans* and *C. albicans* can be grown using the same growth media used before for each. BHI/sucrose for *S. mutans* and RPMI-MOPS for *C. albicans* using equal volumes of each media (100 μL) with the same initial concentration used for each organism (0.01 OD for *S. mutans* and $1\times10^7$ for *C. albicans*). Gesho ethanol extracts were tested at 3 mg/ml. The polymicrobial assay 96-well plate design included *S. mutans*, *C. albicans* and their dual species biofilms untreated compared to their treated counterparts at 3 mg/ml. The plates were washed and stained for reading as done previously. The biofilm biomass for the nontreated biofilms and the synergistic effect of adding the organisms together surpassed the MD plate reader reading limit, therefore a 1:10 dilution of the nontreated biofilms were done before reading and then multiplied by the dilution factor 10 before plotting the data into graphs.

(3) Viability Assays

These assays were done for each extraction after each biofilm assay, the aim is to test the effect of gesho on the planktonic cells in the suspensions of each well for each fraction. This is done as part of the effort for understanding the plants' mechanism for biofilm formation inhibition. Supernatant of cells from control nontreated cells as well as the 7, 5 and 3 mg/ml were extracted from wells to be tested. Each fraction was diluted 1:10 dilutions from $10^{-1}$ to $10^{-7}$. Using petri dishes divided into 8 quadrants for the dilutions, each quadrant inoculated with two drops of 10 μL each. Plates were incubated at 37° C. overnight. Dilutions showing the least number of colonies were counted and the data plotted on excel sheet to calculate log reductions in comparison to the control plate.

(4) Polymicrobial Biofilms Images (a) Flow Cell Biofilm Growth System

To view and image the biofilms they were grown via flow cell system. The flow cell was done but with few changes to fit the present study. The main parts of the flow cell consist of the flow cell slide covered with glass cover slips which are glued using silicon, forming chambers to allow flow of media. The flow cell slide has two adjacent channels through which the media is pumped from the reservoir bottles and circulated for 24 hours at a rate of 0.9 ml/min at 37° C. The coverslips serve as surface for biofilm attachment. The entire system is pre-sterilized through autoclaving and bleaching. Two media reservoirs were prepared. First one for control with no gesho extracts was prepared with 25 ml of Sucrose/BHI broth with *S. mutans* at 0.01 OD as initial concentration, added to 25 ml of RPMI/MOPs with *C. albicans* to reach a total of 50 ml. The second reservoir bottle was prepared like the first one with addition of GSE extract at a 3 mg/ml concentration. Each bottle was connected to a separate flow cell slide and they were incubated simultaneously for 24 hours at the same flow rate.

(b) Epifluorescent Microscope

*C. albicans* and *S. mutans* polymicrobial biofilms 2D images were taken using calcofluor white as a fluorescent dye for *Candida* and SYTO 9 for nucleic acid staining producing blue fluorescence under microscope for *C. albicans* and green for both *C. albicans* and *S. mutans*. The effect of gesho extracts tested on dual species biofilms can be examined by these images that help primarily in viewing its effect on the biofilms in 2D dimensions.

(c) Cell Size of *C. albicans* and *S. mutans* by Image Analysis

AmScope 3.7 for digital camera (United States) software, was used to estimate the size of *S. mutans* and *C. albicans*. Epifluorescent or light microscopy images of biofilms collected as described above were analyzed. Pixels were converted to μm using the following equation: [(Length in pixels)*(10000 μm/cm)]/[(resolution in pixels/cm)*(magnification)]. Representative images were selected and cell dimensions from a minimum of three images were evaluated for gesho-treated and non-treated biofilms.

(5) Molecular Analysis (a) RNA Purification and Extraction

The expression of the *S. mutans* glycosyltransferase genes (gtfB, gtfC) was measured using the protocol of Falsetta with some modifications. Four biofilm cultures were prepared for RNA extraction: *S. mutans* cultivated alone with and without gesho extract, and dual species biofilms of *S. mutans* and *C. albicans* with and without gesho extract. RNA extraction and purification were done using a Direct-Zol™ RNA MiniPrep kit (Zymo research, USA). RNA was collected for both planktonic and biofilm cells. After DNase treatment, the RNA samples were measured for concentration and purity using a NanoDrop spectrophotometer (Thermo scientific, NanoDrop 2000), then stored at −80° C. PCR reactions were performed on RNA samples to ensure the absence of DNA contamination. Genomic *S. mutans* DNA was extracted using a ZR Fungal/Bacterial DNA MicroPrep kit (Zymo research, USA). Genomic *S. mutans* DNA was used to confirm the primer annealing temperature in PCR reaction protocol, and to serve as a positive control in cDNA PCR gel electrophoresis. *S. mutans*16s rDNA primers were used in the PCR reaction to identify if any DNA was still present after DNase treatment and *S. mutans* genomic DNA was used as a positive control. While for annealing temperature confirmation and cDNA controls, the gtfB, gtfC primers were used for PCR reactions.

(b) RT-qPCR

GtfB,C genes primers were ordered according to the primer sequence used by Klein. The Super Script III First-Strand synthesis system for RT-PCR (Invitrogen) was used to convert RNA samples to cDNA. PCR was used to confirm cDNA formation. Standards are prepared by adding specific gtfB, gtfC primers to cDNA. SYBR green are used for RT-qPCR. Samples concentrations are measured using qPCR.

(6) Statistical Analysis

Non-parametric (Kuskal-Wallis Test and Median Test) analyses were performed. Cell size analysis were done using T-Test. Comparisons were done between control (non-treated) and gesho treated samples. Differences with a p-value<0.05 were considered statistically significant and are noted with asterisk (*).

(7) Applications

Natural products and plant extracts were proven to exhibit antimicrobial, anti-adhesive and anti-biofilm activities against oral pathogens. Plants represent a rich source of novel compounds and chemicals that can be used in pharmaceutical products. An estimated 500,000 species are present around the world with only 1% studied for their phytochemical activity. Herbs, in contrast to synthetic chemical compounds are a safe source of treatment. Many of which have been used traditionally for medicinal purposes, one of which is for oral health. Many herbal products are used as antimicrobials, anti-inflammatory and analgesics in dentistry. The increased resistance to antibiotics as well as their adverse side effects in dentistry raised the need for other treatment options, natural products represented a promising and safe treatment alternative. Gesho, an African plant, exhibited antimicrobial, anti-biofilm activity not only against Gram positive bacterial but also against two of the most common oral pathogens, *C. albicans* biofilms and *S. mutans* biofilms. Gesho represents an addition of a promising herbal treatment against the oral biofilms. It can be a source of natural anti-biofilm prevention source than can be used in many applications as mouthwashes or tooth pastes.

(8) Conclusion

The enhanced resistance of biofilms to antimicrobials helps make them major source of chronic infection. The existence of polymicrobial biofilms increases their strength and their resistance. Gesho ethanol extracts were found to exhibit biofilm formation inhibitory effect. Its effect has been demonstrated on both *S. mutans* and *C. albicans* as well as their polymicrobial biofilms. The mechanism by which it prevents their biofilm formation is still not resolved, but some hypothesis include 1) it exhibits biocidal effects on *S. mutans*, 2) it has anti-quorum sensing effects on *C. albicans* or 3) it has the ability to inhibit formation of the EPS through different mechanisms.

It is shown herein for first time that gesho stem extracts possess inhibitory anti-biofilm effects. Also focused on are polymicrobial biofilms that are formed of dual species of yeast and bacteria. And as part of the study it is shown that gesho inhibits yeast biofilm formation as well as Gram positive bacteria. Gesho's traditional use makes its future use in antibiofilm products applicable, for example toothpaste or mouthwash. Gesho anti-biofilm results make it a promising antibiofilm agent.

Example 2: *Rhamnus prinoides* (Gesho): A Source of Diverse Antimicrobial and Anti-Biofilm Activity Microbial biofilms, or surface-attached communities of microorganisms, are a source of chronic infection. In contemporary medicine, concern over biofilms is frequently elicited by device-related infections such as occur with catheters and joint replacements. A wide range of pathogenic bacteria are reported to establish biofilm infections. These include *Staphylococcus aureus* and *Streptococcus mutans*, two opportunistic pathogens whose biofilms are responsible for diseases including endocarditis and tooth decay, respectively. In traditional settings, biofilm-associated infections would most commonly be encountered in wounds, on the skin and in the mouth. The severity of biofilm infections in combination with the increased prevalence of antibiotic resistance, has led to an ethnopharmacological approach to finding novel anti-biofilm agents.

is a large evergreen shrub native to East Africa that is used as a bittering agent in the traditional East African fermented beverages tella and tej. In addition to its culinary use, gesho has been used historically as a treatment for a variety of illnesses. Aqueous tinctures containing gesho have been used for the treatment of arthritis, back pain, brucellosis, flu, common cold, indigestion, loss of appetite, pneumonia, fatigue, sexually transmitted diseases, stomach ache and ear, nose and throat infections. Notably, a mixture of ground *R. prinoides* leaves and butter has been used as an ointment for the treatment of atopic dermatitis, a skin condition occasionally associated with *Staphylococcus aureus* infections. Gesho contains a complex mixture of potentially therapeutic biocidal chemicals active against planktonic pathogens, notably geshoidin, quercetin, emodin, and various anthracene derivatives. Based on this background information, we hypothesized that gesho could be a source of anti-biofilm compounds effective against *S. aureus* and other Gram positive bacteria.

A) Results and Discussion (1) Gesho Ethanol Extracts have Biocidal Activity Against Log Phase Planktonic Cells Ethanol and aqueous extracts of gesho were tested for their ability to kill log-phase, planktonic cells of *Staphylococcus aureus*, *Streptococcus mutans* and *Bacillus subtilis*. Ethanol extract treatments resulted in a 2 to 10 log reduction in colony forming units (CFU) per mL; whereas aqueous extract treatments resulted in a 1 to 3 log reduction in CFU per mL (FIG. 13). Both stem and leaf ethanol extracts exhibited significant biocidal activity against all three species tested. The effects of aqueous extracts were more variable with only the stem extract showing activity against S. aureus and B. subtilis but not S. mutans.

(2) Gesho Ethanol Extracts Influence the Growth of Stationary Phase Cells

Gesho ethanol extracts exhibit biocidal or bacteriostatic activity against stationary phase cells. The number of viable cells present in the inocula, indicated by a dotted red line, were quantified to allow for comparisons of growth relative to starting conditions (FIG. 14). Treatments of B. subtilis or S. mutans with stem ethanol extract resulted in a decrease in biomass when compared to the untreated inoculum, signifying biocidal activity. Stem ethanol treatment of S. aureus and leaf ethanol treatments of S. mutans and B. subtilis exhibited a bacteriostatic effect, showing little change in cell number from the inocula. Leaf ethanol extract impaired S. aureus growth in comparison to growth of the untreated control, possibly due to slight bactericidal activity or toxicity of the treatment. The variability of these findings indicates that the gesho ethanol extracts contain a mixture of chemicals that impact Gram positive bacteria in a species specific manner. Overall, these findings indicated that the stem ethanol extract was a good source of biocidal, anti-biofilm compounds, whereas the leaf ethanol extract was a good source of non-biocidal antibacterial (i.e. antipathogenic) compounds. Due to the superior inhibition of biofilm formation caused by the ethanol extracts, we elected not to assess the activity of the aqueous extracts on stationary phase cells (FIG. 15).

(3) Gesho Ethanol Extracts Prevent Gram Positive Bacterial Biofilm Formation

Gesho ethanol extracts strongly inhibited Gram positive bacterial biofilm formation. Both ethanol stem and leaf extracts significantly inhibited S. aureus, S. mutans and B. subtilis biofilm formation up to 99% relative to untreated control biofilms (FIG. 15). The extent of inhibition was species dependent with S. aureus showing less susceptibility to treatment than B. subtilis and S. mutans. Aqueous extracts inhibited S. aureus and S. mutans biofilms but increased B. subtilis biofilm formation. B. subtilis biofilm formation may have been stimulated by the presence of sugars or Bacillus-specific biofilm-inducing compounds in the extract. As noted above, the effects of aqueous extracts were more variable in activity, resulting in inhibition of S. aureus and S. mutans but not B. subtilis biofilms. Stem extracts generally resulted in greater biofilm inhibition than their leaf counterparts, indicating a difference in chemical composition between the two tissues. All extracts were ineffective at disrupting existing biofilms or inhibiting Gram negative bacterial biofilm formation (FIG. 16).

(4) Gesho-Derived Small Molecules Inhibit Gram Positive Biofilm Formation

Further work on the leaf ethanol extract was pursued because the data in FIGS. 14 and 15 indicated that compounds contained within prevented biofilm formation with minimal bactericidal activity. Liquid to liquid fractionation was used to separate the extract on the basis of polarity, followed by chemical tests, Fourier Transform infrared spectroscopy (FTIR) and gas chromatography-mass spectrometry (GC-MS) (FIG. 17). Low pressure liquid chromatography of the butanol and ethyl acetate liquid to liquid fractions indicated that the most effective compounds were present in the more polar liquid phases (FIG. 18). Colorimetric chemical tests indicated the presence of polyphenolic and alcoholic compounds (Table 1). FTIR supported these findings, showing a strong hydroxyl peak and several alkyl or alkene peaks (FIG. 19). GC-MS analysis found numerous peaks within the butanol fraction (FIG. 20); compound identities were determined using the NIST11 chemical library. Compounds resulting in a certainty score greater than 85% were selected for further analysis. Activity screens identified two compounds with anti-biofilm activity: ethyl 4-ethoxybenzoate (CAS #23676-09-7) and 4-hydroxy-4-methyl pentanone (CAS #123-42-2) (FIG. 20). Ethyl 4-ethoxybenzoate (EEB) and 4-hydroxy-4-methyl pentanone (HMP) are naturally occurring compounds that have been previously been extracted from plants. 4-hydroxy-4-methyl pentanone, also known as diacetone alcohol (DAA), is commonly used as an industrial solvent; however, HMP was not used as a solvent in this study, suggesting that it occurs naturally in gesho. Benzoic acid and 2-pentanone, compounds that are structurally similar to EEB and HMP respectively, were evaluated for anti-biofilm activity at 0.8% and 3%. Neither benzoic acid nor 2-pentanone had a statistically significant effect on biofilm formation. These data support the concept that the observed anti-biofilm activity of EEB and HMP was caused by their chemical structures rather than by non-specific effects.

TABLE 1

Chemical tests indicate the presence of alcohol- and phenol-containing compounds in the butanol and ethyl acetate fractions

| Chemical Test | Functional group | Test result |
| --- | --- | --- |
| Ninhydrin test | Amines | Negative |
| Folin-Ciocalteu test | Polyphenols | Positive |
| Beyer/Potassium permanganate test | Alkenes and Alkynes | Negative |
| Jones Oxidation/ Sodium Chromate test | Alcohols | Positive |
| Carboxylic acid test | Carboxylic acid | Negative |
| Biuret test | Peptide bonds | Negative |

A major peak in the butanol fraction was identified as dimethyl sulfoxide (DMSO). DMSO is commonly used in laboratories as a solvent, but, in this study, it was a component of the GC-MS output (FIG. 20). We considered several hypotheses to explain its presence. First, we analyzed all of the solvents used in this work to determine whether it was a contaminant. GC-MS analyses indicated that it was not found in the solvents (data not shown). Second, we considered whether it could be a natural product; however, we could not find any published reports that support this idea. Lastly, we hypothesized that DMSO could be a rearrangement product that formed as an artifact during GC-MS analysis. Regardless, we hypothesized that the presence of DMSO increased the anti-biofilm activity of EEB by increasing its solubility; this idea was supported by laboratory experiments (FIG. 21A). DMSO was combined with HMP to assess if DMSO would result in enhanced anti-biofilm activity as occurred with EEB, but DMSO did not enhance HMP activity.

EEB and HMP treatments exhibited significant anti-biofilm activity but did not show antibacterial activity against log or stationary phase cells; these are hallmark characteristics of "antipathogenic" compounds (FIGS. 21C, 21D, 21E, and 21F). Antipathogenic therapeutics are compounds that target pathogen virulence mechanisms while minimizing bactericidal activity. Antipathogenic compounds have gained attention in recent years because they apply less selective pressure against pathogens than bactericidal agents and so may delay the development of antibiotic resistance. The anti-biofilm activity of HMP may derive from its structural similarity to autoinducer-2 (AI-2), a quorum sensing signaling molecule that affects diverse bacterial phenotypes including biofilm formation. HMP may act as a competitive inhibitor of AI-2 signaling. Notably, HMP inhibited biofilm formation by *P. aeruginosa* PA01, although this activity was not observed with the crude gesho extracts (FIG. 22). The mode of action behind the anti-biofilm activity of EEB is unknown, but its structural similarity to parabens suggest that it may influence biofilm formation through a common mechanism.

There are several novel features in the presented work. This is the first research project to focus on gesho for its anti-biofilm activity. This work complements existing findings on the antibacterial and anti-parasitic properties of gesho. Second, the extracts used in this research were unique compared to those used in prior works; they were prepared using ethanol rather than methanol in an effort to extract chemical compounds that were likely to be present in traditional brews and tinctures. Third, this project tested both leaf and stem extracts independently for antibacterial and anti-biofilm activity, which proved informative as their characteristics and efficacies were different. Overall, our findings support the traditional use of gesho for health benefits and also indicate that gesho-derived compounds could potentially have applications as therapeutics and as hygiene products.

b) Materials and Methods (1) Bacterial Strains and Culture Conditions

Four species of microorganisms were employed in this work: *Staphylococcus aureus* ATCC 6538, *Bacillus subtilis* ATCC 23059, *Pseudomonas aeruginosa* PA01 and *Streptococcus mutans*. *Streptococcus mutans* was a gift from Margaret Gould-Bartlett, Georgia State University. *Pseudomonas aeruginosa* PA01 was obtained from the laboratory of Jay Keasling, University of California, Berkeley. *S. aureus* was grown in Luria-Bertani (LB) broth (Becton Dickinson, USA). *B. subtilis* was cultivated in LB broth supplemented with 150 mM ammonium sulfate, 100 mM potassium phosphate, 34 mM sodium citrate, 1 mM $MgSO_4$ and 0.1% glucose. *S. mutans* was grown in Brain-Heart Infusion (BHI) medium (Becton, Dickinson, USA) supplemented with 0.5% sucrose. *P. aeruginosa* was cultivated in *Pseudomonas* basal mineral (PBM) medium containing 80 mM glucose.

(2) Chemicals and Reagents

The following reagents were purchased from Fisher Scientific (USA): crystal violet, potassium phosphate, magnesium sulfate, ammonium sulfate, hexanes, methanol, and sodium carbonate. Reagents purchased from Sigma Aldrich (USA) include: sucrose, butanol, Folin-Ciocalteu reagent, ninhydrin reagent, sodium bicarbonate, cupric sulfate. Sodium citrate, glucose and ethyl acetate were purchased from EM Science (USA), OmniPur (Germany) and Pharmco-Aaper (USA), respectively. 95% ethanol was purchased from Decon Labs (USA).

(3) Extract Preparation

*Rhamnus prinoides* stem and leaf material was purchased from a local Ethiopian market (Buford, Georgia, USA). Twenty-four grams of *R. prinoides* pre-ground leaves or fractured stems were added to 150 ml of sterile water or 95 percent ethanol in a 250 mL flask. Flasks were shaken in the absence of light at 200 rpm at room temperature for four days. Extraction liquid was then collected and particulate matter removed via centrifugation at 15,000 rpm at 4° C. for 5 minutes; clarified supernatants were recovered for further processing. Aqueous extracts were frozen at −80° C. and lyophilized to remove all water. Ethanol extracts were air-dried under vacuum to evaporate solvent before suspension in water and lyophilization. Extracts were stored at −80° C.

(4) Log-Phase Cell Antimicrobial Assay

Bacteria were inoculated in 20 ml of growth media at an initial optical density ($OD_{600}$) of 0.01 and incubated at 37° C., 200 rpm until log-phase was reached. One milliliter of log-phase cells was transferred to 1.5 ml microfuge tubes and growth media removed via centrifugation. Pelleted cells were washed twice with phosphate buffered saline (PBS) before resuspending the pellets in 1 ml of extract dissolved in PBS. Treatments were incubated at 37° C. for 1 hour then serially diluted in PBS and radially plated on growth agar. Plate counts were used to assess biocidal activity.

(5) Stationary-Phase Cell Viability Assay

To assess the viability of stationary phase planktonic cell, a growth agar based assay was conducted. Spent media containing stationary phase planktonic cells was collected after a biofilm formation assay. Collected cells were serially diluted in PBS and dilutions were radially plated in 10 μl volumes on growth medium. Agar plates were incubated at 37° C. overnight to allow for colony formation. Plate counts were used to assess viability.

(6) *Staphylococcus aureus* and *Streptococcus mutans* Biofilm Formation Assay

*Staphylococcus aureus* and *Streptococcus mutans* biofilms were grown in Luria-Bertani (LB) broth and brain-heart infusion (BHI) medium containing 0.5% sucrose, respectively. Biofilm formation was assessed using a polystyrene 96 well microtiter plate crystal violet assay. Overnight broth cultures were diluted to an initial optical density ($OD_{600}$) of 0.01 in fresh media and combined with gesho extract to obtain a final concentration of 7 mg/ml. Treatments were then serially diluted to final extract concentrations of 5, 3, 1, 0.5 and 0.25 mg/ml. Negative controls consisted of cells diluted to an initial optical density ($OD_{600}$) of 0.01 in growth media without plant extract. 100 μl of treated and untreated samples were added to each well of a microtiter plate and incubated at 37° C. for 24 hours. After 24 hours, planktonic cells and spent growth media were removed from each well and the plate was washed three times in sterile water. Biofilms were then stained with 150 μl of 0.1% crystal violet for 15 minutes at 200 rpm. Excess dye was removed via washing in sterile water and the plate was allowed to air dry. Crystal violet was solubilized in 150 μl of 95% ethanol and absorbance measurements at 595 nm ($OD_{595}$) were taken using an MD SPECTRAmax plate reader (Molecular Devices Corporation, California).

(7) *Bacillus subtilis* Biofilm Formation Assay

*Bacillus subtilis* biofilms were grown in LB broth supplemented with 0.15 M ammonium sulfate, 100 mM potassium phosphate, 34 mM sodium citrate, 1 mM $MgSO_4$ and 0.1% glucose. Overnight broth cultures were diluted to an initial optical density ($OD_{600}$) of 0.01 in fresh supplemented LB media and combined with gesho extract to obtain a final concentration of 7 mg/ml. Treatments were then serially diluted to final concentrations of 5, 3, 1, 0.5 and 0.25 mg/ml. Negative controls consisted of cells diluted to an initial optical density ($OD_{600}$) of 0.01 in growth media alone. 1 ml of treated and untreated samples were added to 10 ml glass culture tubes and statically incubated at 30° C. for 48 hours. After 2 days, planktonic cells and spent growth media were removed from below the pellicle that formed at the air to liquid interface. Pellicles were vortexed and pipetted for resuspension in PBS then serially diluted in PBS and radially plated on LB agar plates. Plate counts were used to quantify the number of biofilm cells.

(8) Pure Compounds on *Staphylococcus aureus* and *Pseudomonas aeruginosa* Biofilm Formation Assay

*Staphylococcus aureus* and *Pseudomonas aeruginosa* biofilms were grown in LB broth and PBM-glucose, respectively. Biofilm formation was assessed using a polystyrene 96 well microtiter plate crystal violet assay. Overnight broth cultures were diluted to an initial $OD_{600}$ of 0.01 in fresh media and combined with pure compounds to obtain a final concentration of 6.2% (v/v). Treatments were then serially diluted to final concentrations of 3.1, 1.7, 0.8 and 0.4% (v/v). DMSO was added to solubilize the treatments. Negative controls consisted of cells diluted to an initial $OD_{600}$ of 0.01 in growth media without treatment. 100 μl of treated and untreated samples were added to each well of a microtiter plate and incubated at 37° C. for 24 h. After 24 h, planktonic cells and spent growth media were removed from each well and the plate was washed 3 times in sterile water. Biofilms were then stained with 150 μl of 0.1% crystal violet for 15 min at 200 rpm. Excess dye was removed via washing in sterile water and the plate was allowed to air dry. Crystal violet was solubilized in 150 μl of 95% ethanol and absorbance measurements at 595 nm were taken using an MD SPECTRAmax plate reader (Molecular Devices Corporation, USA).

(9) Liquid to Liquid Extraction

Liquid to liquid extraction was conducted to separate the various components of the gesho leaf ethanol extract. A 1:1 ratio of water and hexanes was added to a separatory funnel. 500 mg of gesho leaf ethanol extract solubilized in 10 ml of 95% ethanol was added to the separatory funnel. Solvents were thoroughly mixed via inversion then allowed to separate before fraction collection in 250 ml flasks. Aqueous fractions were reintroduced to the separatory funnel and an additional 10 ml hexanes was added. Solvents were mixed via inversion and allowed to separate for fraction collection. A final hexane separation was conducted using an additional 10 ml of hexane. Subsequent extractions were performed with water saturated butanol and ethyl acetate following the aforementioned method. All fractions were dried to remove solvents, re-suspended in water and lyophilized.

(10) Low Pressure Liquid Chromatography (LPLC)

LPLC was performed using Bondapack C18/Corasil as the stationary phase. 10 mg/ml and 7 mg/ml of the butanol and ethyl acetate fractionations, respectively, were dissolved in 1 ml of ethanol and applied to the column. Gradient separations were performed changing mobile phase at 10% intervals from 100% methanol to 100% water. Eluted fractions were collected in polystyrene culture tubes at 5 ml intervals and stored at 4° C.

(11) Chemical Tests

Chemical tests were used to help identify the chemical components present in *R. prinoides* ethanol extracts. The tests conducted were as follows:

(a) Ninhydrin Test for Amines:

10 μl of sample was added to chromatography paper and dried. 10 μl of ninhydrin reagent was applied to each sample and allowed to dry. A purple coloration indicated a positive result.

(b) Folin-Ciocalteu Test for Phenols:

18 μl of samples and 36 μl of Folin-Ciocalteu reagent were added to wells of a microtiter plate and allowed to incubate at room temperature for 5 minutes at 200 rpm. 145 μl of 20% sodium carbonate was added to each well and absorbance measurements at 750 nm were made using an MD plate reader.

(c) Baeyer/Potassium Permanganate Test for Alkenes and Alkynes:

500 μl of acetone was added to glass test tubes followed by the addition of 1 drop of each sample. Samples were thoroughly mixed and one drop of 1% aqueous potassium permanganate was added to each tube and shaken vigorously. A positive result was indicated by a color change from purple to brown.

(d) Jones Oxidation/Sodium Chromate Test for Alcohols:

5 drops of acetone and chromate solution were added to glass test tubes followed by 4 drops of each Low pressure liquid chromatography (LPLC) fraction; mixture was thoroughly mixed. Positive results were indicated by a color change from orange to green/blue.

(e) Carboxylic Acid Test:

3 drops of each LPLC fraction were added to a glass test tube. 1 ml of 100 mg/ml sodium bicarbonate solution was slowly added to each tube. Positive results were indicated by the appearance of gas bubbles.

(f) Biuret Test for Peptide Bonds:

3 drops of sample and 10 drops of sodium hydroxide was added to glass test tubes and mixed thoroughly. Two drops of 25 mg/ml cupric sulfate were added to each tube and shaken vigorously. A dark blue/purple coloration indicated a positive result.

(12) Gas Chromatography-Mass Spectrometry (GC-MS)

Gas chromatography-mass spectrometry (GC-MS) analysis was performed using an Agilent Technology 7890A gas chromatograph equipped with an Agilent Technology 5977A mass spectrometer. A sample volume of 5 μL was manually injected into an Agilent (30 m, 0.530 mm) DB-FFAP column. The oven method began at 60° C. for 5 min, then was raised to 100° C. at 25° C./min. The temperature was stabilized at 100° C. for 1 min then raised to 200° C. at 25° C./min and held at 200° C. for 1 min. Temperature was raised to 250° C. at a rate of 5° C./min then held at the final baking temperature of 250° C. for 7 min. Agilent MassHunter software was used for mass spectrometry data acquisition and analysis.

(13) Fourier Transform Infrared Spectroscopy (FTIR)

A Varian UMA 600 FTIR microscope equipped with He—Ne laser and MCT detector was used for analysis. 3 μL of LPLC samples were vacuum desiccated onto zinc solenoid windows. Data were collected in the 3750-925 $cm^{-1}$ region at a 4 $cm^{-1}$ spectral resolution.

(14) Statistical Analysis

Non-parametric (Kuskal-Wallis Test and Median Test) or parametric (ANOVA followed by Tukey HSD test or t-test) analyses of variance were conducted based on the characteristics of the data. Comparisons were conducted between the extract treated samples and the untreated control. Differences with a p-value<0.05 were considered statistically significant and are designated with an asterisk (*).

Example 3: Effects of 4-Ethoxybenzoic Acid and Methyl Gallate on *Staphylococcus aureus* Biofilm Formation and Vancomycin Sensitivity/Susceptibility

*Staphylococcus aureus* biofilms are the etiological agent associated with atopic dermatitis, osteomyelitis, endocarditis and various chronic infections. *S. aureus* infections have been made more difficult to treat due to the increased prevalence of methicillin and vancomycin resistance. Benzoic compounds including tannic acid, vanillic acid, syringic acid have been found to exhibit biocidal activity against both planktonic and biofilm-associated *S. aureus*; however, the effects of some benzoic compound impacts on biofilms in combination with antibiotics remains unknown. In this study, we investigated the effects of various benzoic compounds on *S. aureus* biofilms and susceptibility to antibiotic treatments. Our work suggest that benzoic compounds can act as adjuvants to vancomycin treatments decreasing the antibiotic's effective concentration which could prolong vancomycin's use on the market.

A) Results and Discussion (1) 4-Ethoxybenzoic Acid, Methyl Gallate and Methyl Paraben Exhibit Antipathogenic Anti-Biofilm Activity Benzoate derivative compounds have antibacterial and anti-biofilm effects on *Staphylococcus aureus*. Numerous benzoic compounds were assessed for *S. aureus* anti-biofilm activity (FIG. 23). Concentrations of compound required to inhibit fifty percent biofilm formation (BP50) and fifty percent of resting cell viability (LC50) were calculated and each compound was categorized as low potency (BP50≥7.5 mM; LC50≥15 mM), biocidal (LC50≤0.44-15 mM) or antipathogenic (BP50≤7.5; LC50≥15) based on the calculated BP and LC50 values (FIGS. 24, 25, and 26, table 2). 3-hydroxybenzoic acid, paraben, pyrocatechuic acid, gentisic acid, protocatechuic acid, ethyl gallate and propyl gallate all possessed low LC50 values and thus were all categorized as biocidal regardless of their BP50. These compounds were toxic and primarily inhibited biofilm formation through a biocidal mechanism. Low potency compounds included gallic acid, salicylic acid and ethyl 4-ethoxybenzoic. These compounds were relatively non-toxic, exhibited by their high LC50; however, high concentrations were required to inhibit biofilm formation. 4-ethoxybenzoic acid, methyl gallate and methyl paraben were also minimally toxic, but unlike the low potency compounds, they inhibited *S. aureus* biofilm formation at low concentrations. These compounds were categorized as antipathogenic, as the absence of growth inhibition accompanied by biofilm inhibition is a defining characteristic of an antipathogenic compound (citation) (FIG. 24). The antipathogenic activity of 4-ethoxybenzoic acid, methyl gallate and methyl paraben after 24 hours of growth led us to investigate the impacts of these compounds on the *S. aureus* growth rate.

TABLE 2

BP50 and LC50 of benzoic compounds on *Staphylococcus aureus* biofilm formation and viability

| Compound | BP50 (mM) | LC50 (mM) |
|---|---|---|
| methyl gallate | 0.82 | 18.8 |
| ethyl gallate | 6.7 | 9.8 |
| propyl gallate | 2.9 | 6.6 |
| 4-ethoxybenzoic acid | 1.6 | 33.5 |
| p-hydroxybenzoic acid | 8 | 14 |
| methyl paraben | 5.7 | 22.9 |
| 3-hydroxybenzoic acid | 9.6 | 14 |
| gentisic acid | 9.2 | 11 |
| pyrocatechuic acid | 4.8 | 8.9 |
| protocatechuic acid | 14.4 | 13.2 |
| gallic acid | 17.3 | 21.6 |
| salicylic acid | 38.5 | 46.4 |
| EEB+ 1% DMSO | 103.6 | 818 |

(2) 4-Ethoxybenzoic Acid, Methyl Gallate and Methyl Paraben Exhibit Attenuate the Growth of *Staphylococcus aureus*

*Staphylococcus aureus* cells were exposed to antipathogenic concentrations of 4-ethoxybenzoic acid, methyl gallate and methyl paraben to assess the effects of the compounds on growth rate. Optical densities of test tube cultures were measured at one hour intervals for nine hours and a final measurement was taken at 24 hrs. All compounds negatively impacted the *S. aureus* growth rate with the lower concentrations of compound resulting in less attenuation then their higher counterparts (FIG. 27 and Table 3). Differences in growth diminished after 24 hours with the turbidity of each culture becoming indistinguishable. The impact of growth rate suggests that 4-ethoxybenzoic acid, methyl gallate and methyl paraben possessed some level of toxicity that the cells overcame over time. Due to the recent societal health concerns around the use of parabens and high concentration of methyl paraben needed to observe an antipathogenic phenotype, we elected to continue our studied with only 4-ethoxybenzoic acid and methyl gallate.

TABLE 3

Effects of 4-ethoxybenzoic acid, methyl gallate and methyl paraben on *Staphylococcus aureus* growth rate

| Treatment | Growth rate (log replications/hr) | Percent attenuation |
|---|---|---|
| Untreated control | 1.11 | 0 |
| 1.2 mM 4-ethoxybenzoic acid | 0.97 | 12 |
| 2.4 mM 4-ethoxybenzoic acid | 0.58 | 47 |
| 1.1 mM methyl gallate | 0.77 | 30 |
| 1.2 mM methyl gallate | 0.59 | 46 |
| 5.2 mM methyl paraben | 0.83 | 25 |
| 1.1 µM vancomycin | 0.0 | 100 |

(3) 4-Ethoxybenzoic Acid and Methyl Gallate Enhance the Antimicrobial and Anti-Biofilm Activities of Vancomycin The synergistic effects of compound and vancomycin treatments on biocidal activity and anti-biofilm activity were assessed using the minimum biofilm eradication concentration (MBEC) of vancomycin and various concentrations of 4-ethoxybenzoic acid or methyl gallate. Vancomycin and 4-ethoxybenzoic acid combination treatments exhibited synergistic effects, killing more biofilm cells than vancomycin or 4-ethoxybenzoic acid treatments alone (FIG. 28). Methyl gallate and vancomycin combination treatments did not exhibit synergism, indicating the effects of these treatments were due to vancomycin or methyl gallate alone (FIG. 28).

(4) 4-Ethoxybenzoic Acid and Methyl Gallate Alters *Staphylococcus aureus* Hydrophobicity.

The effects of 4-ethoxybenzoic acid and methyl gallate on *S. aureus* physiology is unknown. 4-ethoxybenzoic acid and methyl gallate decreased the hydrophobicity of *S. aureus*. Hydrophobic interactions between a solid surface and the cell wall plays an important role in attachment, am early stage of biofilm formation. The decrease in hydrophobicity seen by methyl gallate and 4-ethoxybenzoic acid suggests that their anti-biofilm activities are in part due to obstruction of *S. aureus* attachment to the polystyrene 96 well plate.

b) Materials and Methods (1) Bacterial Culture Conditions and Reagents

*Staphylococcus aureus* ATCC 6538 was grown in Luria-Bertani (LB) broth (Becton Dickinson, USA). Compounds assessed in this study include: 2-hydroxybenzoic acid (salicyclic acid), 3-hydroxybenzoic acid, 4-hydroxybenzoic acid (paraben), 4-hydroxybenzoic acid methyl ester(methyl paraben), 2,3-dihydroxybenzoic acid (pyrocatechuic acid), 2,5-dihydroxybenzoic acid (gentisic acid), 3,4-dihydroxybenzoic acid (protocatechuic acid), gallic acid, methyl gallate, ethyl gallate, propyl gallate, 4-ethoxybenzoic acid and ethyl 4-ethoxybenzoic acid. The following reagents were purchased from Fisher Scientific (USA): crystal violet, dimethyl sulfoxide, 4-ethoxybenzoic acid, ethyl gallate, gallic acid, hexadecane, 3-hydroxybenzoic acid, methyl gallate, potassium chloride, dibasic potassium phosphate, monobasic potassium phosphate and sodium chloride. Reagents purchased from Sigma, Aldrich or Sigma-Aldrich (USA) include: hexadecane, gentisic acid, p-hydroxybenzoic acid, methyl paraben, protocatchuic acid, pyrocatechuic acid, resazurin, salicylic acid and vancomycin. Bactro agar, yeast extract and tryptone were purchased from BD biosciences (USA). Ethyl 4-ethoxybenzoic acid, 95% ethanol, propyl gallate, and rabbits were was purchased from Combi-blocks (USA), Decon Labs (USA), Nutritional Biochemical Corporation (USA) and Hemostat Laboratories (USA)

(2) Biofilm Formation Assay

Biofilm formation was assessed using a polystyrene 96 well microtiter plate crystal violet assay.[23] Overnight broth cultures were diluted to an initial $OD_{600}$ of 0.01 in fresh LB and combined with a target compound to obtain a final concentration of 7 mg/ml. Treatments were then serially diluted to final extract concentrations of 5, 3, 1, 0.5 and 0.25 mg/ml. No vehicles were added to solubilize the treatments. Untreated cells served as negative controls. 100 µl of treated and untreated samples were added to each well of a microtiter plate and incubated at 37° C. for 24 h. After 24 h, planktonic cells and spent growth media were removed from each well and the plate was washed 3 times in sterile water. Biofilms were then stained with 150 µl of 0.1% crystal violet for 15 min at 200 rpm. Excess dye was removed via washing in sterile water and the plate was allowed to air dry. Crystal violet was solubilized in 150 µl of 95% ethanol and absorbance measurements at 595 nm were taken using an MD SPECTRAmax plate reader (Molecular Devices Corporation, USA). The molarity of each treatment was calculated using excel.

(3) Resting Cell Viability Assay

To assess the viability of stationary phase planktonic cells, a growth agar-based assay was conducted. Spent media containing stationary phase planktonic cells were collected from microtiter plates after the conclusion of each biofilm formation assay. The collected cells were serially diluted (1:10) in PBS and dilutions were radially plated in 10 µl volumes on growth medium. Agar plates were incubated at 37° C. overnight to allow for colony formation and plate counts were used to assess viability. Colony forming units per milliliter of culture (CFU/mL) was calculated by dividing the colony counts (C) by the volume added (V) multiplied by the dilution factor (D): $CFU/mL=C/(V \times D)$ (4) Staphylococcus aureus Growth Curve Overnight broth cultures were diluted to an initial $OD_{600}$ of 0.01 in fresh LB media combined with 4-ethoxybenzoic acid (0.2 or 0.4 mg/mL), methyl gallate (0.2 or 0.4 mg/mL) or methyl paraben (0.8 or 1.7 mg/mL). 2 mL of each treatment was added to 19 culture tubes and the samples were incubated for 24 h at 37° C. with shaking at 200 rpm. 1 mL of each sample was transferred to a cuvette and the absorbance measurements at 600 nm were taken every hour for 9 hours. 24 h measurements were taken the following day. Untreated samples and samples containing 1.6 µg/mL vancomycin served as a negative and positive controls, respectively. Growth rates were calculated using the slope of the log phase of growth (t=0 h and t=4 h).

(5) Log-Phase Cell Antimicrobial Assay

Bacteria were inoculated in 20 ml of growth media at an initial optical density ($OD_{600}$) of 0.01 and incubated for 4±1 h at 37° C. with shaking at 200 rpm until log phase ($OD_{600} \approx 0.35$) was reached. 1 ml of log-phase cells was transferred to 1.5 ml microfuge tubes and the growth medium was removed via centrifugation. Pelleted cells were washed twice with phosphate buffered saline (PBS) before resuspending the pellets in 1 ml of 4-ethoxybenzoic acid or methyl gallate with or without vancomycin dissolved in PBS. Treatments were incubated at 37° C. for 1 h and then serially diluted in PBS and radially plated on growth agar. Plate counts were used to assess biocidal activity.

(6) Staphylococcus aureus Biofilm Killing Assay

Staphylococcus aureus biofilms were formed as described above. Staphylococcus aureus biofilms were grown in LB broth. Overnight broth cultures were diluted to an initial $OD_{600}$ of 0.01 in fresh media and 100 µL of culture was added to each well of a 96 well polystyrene microtiter plate; biofilms were allowed to form at 37° C. for 24 hrs. After incubation, spent media was removed and biofilms were washed twice with 150 µL of PBS. Methyl gallate, 4-ethoxybenzoic acid and methyl paraben were suspended in LB media to a final concentration of 7 mg/mL. Treatments were then serially diluted to final concentrations of 3.5, 1.7, 0.8, 0.4, 0.2 and 0.1 mg/mL. Vancomycin treatments were diluted to a final concentration of 3.1 ug/mL. No vehicles were added to solubilize the treatments. Negative controls consisted of 100 µL of fresh LB without compound or antibiotic. 100 µl of each treatment was added to each well of a microtiter plate and incubated at 37° C. for 24 h. After 24 h, planktonic cells and spent growth media were removed from each well and the biofilms were washed twice with 150 µL of PBS. 100 µL of 10 µg/mL resazurin in LB was added to each biofilm and the plate was statically incubated at 37° C. for 3 hrs. During incubation, fluorescence intensity was measured at $\lambda_{ex}=570$ nm $\lambda_{em}=590$ nm every 6 minutes using an Enspire fluorescence plate reader. Data was normalized to the emission at t=0 and the rates of resazurin conversion to resorufin was calculated to identify the time at which maximum fluorescence was achieved.

(7) Staphylococcus aureus Hemolysis Assay

Hemolysis activity was assessed according to Lee, et al, 2014 with a few modifications. Overnight Staphylococcus aureus broth cultures were diluted to an initial $OD_{600}$ of 0.01 in fresh LB containing 4-ethoxybenzoic acid (0.2 or 0.4 mg/mL), methyl gallate (0.2 or 0.4 mg/mL) or methyl paraben (0.8 or 1.7 mg/mL). Cultures were then incubated for 24 h at 37° C. with shaking at 200 rpm. 1 ml of each sample was transferred to 1.5 mL microfuge tubes and centrifuged at 10,000 rcf for 2 minutes. 100 µL of supernatant was added to 900 µL of 4% rabbit's blood (previously washed twice with 1×PBS via centrifugation at 800 rcf for 2 min). Hemolysis samples were incubated for 1 h at 37° C., shaking at 200 rpm. PBS and 10% SDS treated samples served as negative and positive controls, respectively. Samples were then centrifuged at 2,000×g for 5 min to pellet any intact blood cells. 100 µL of each supernatant was added to a 96 well microtiter plate and absorbance measurements at 450 nm were taken using an MD SPECTRAmax plate reader (Molecular Devices Corporation, USA).

(8) Hydrophobicity Test (Microbial Adherence to Hydrocarbon Test)

Hydrophobicity analysis was conducted according to Ciccio, et al., 2015 with a few modifications. Three milliliters of Staphylococcus aureus cultures were grown in the presence of 4-ethoxybenzoic acid (0.2 or 0.4 mg/mL) or methyl gallate (0.2 or 0.4 mg/mL) for 24 h at 37° C. with shaking at 200 rpm. Cultures were diluted to an $OD_{600}$ of 0.6 and washed with 1 mL PBS. 5 mL of the inoculum was produced, 1 mL was removed for plating on growth agar and 1 mL of hexadecane was applied to the air-liquid interface or the remaining 4 mL. Hexadecane samples were vortexed for 1 min and the phases allowed to separate for 15 minutes at room temperature. 1 mL of the aqueous layer was removed and plated on growth agar. Agar plates were incubated at 37° C. overnight and plate counts were conducted the following day. Results were interpreted as the percent of cells present in the aqueous layer prior to ($A_0$) and after ($A_1$) the addition of hexadecane $[(A_0-A_1)/A_0]*100$.

(9) Statistical Analysis

Statistical analysis was performed using IBM SPSS Statistics 22.0 software. Non-parametric (Kuskal-Wallis Test and Median Test) or parametric (ANOVA followed by Tukey HSD test or t-test) analyses of variance were conducted based on the characteristics of the data. Comparisons were conducted between the extract treated samples and the untreated control. Differences with a p-value<0.05 were considered statistically significant and are designated with an asterisk (*).

C. REFERENCES

Abegaz, B., Kebede, T., 1995. Geshoidin: a bitter principle of *Rhamnus prinoides* and other constituents of the leaves. Bullitin Chem. Soc. Ethiop. 9, 107-114.

Adukwu, E. C., Allen, S. C. H., Phillips, C. A., 2012. The anti-biofilm activity of lemongrass (*Cymbopogon flexuosus*) and grapefruit (*Citrus paradisi*) essential oils against five strains of *Staphylococcus aureus*. J. Appl. Microbiol. 113, 1217-1227. doi:10.1111/j.1365-2672.2012.05418.x Águila-Arcos, S. et al. Biofilm-forming clinical *Staphylococcus* isolates harbor horizontal transfer and antibiotic resistance genes. *Front. Microbiol.* 8, 1-12 (2017).

Ahn, S. J., Ahn, S. J., Wen, Z. T., Brady, J., & Burne, R. A. (2008). Characteristics of biofilm formation by *Streptococcus mutans* in the presence of saliva. Infection and Immunity, 76 (9), 4259-4268.

Akiyama, H. Antibacterial action of several tannins against *Staphylococcus aureus*. *J. Antimicrob. Chemother.* 48, 487-491 (2002).

Albayaty, Y. N., Thomas, N., Hasan, S. & Prestidge, C. A. Penetration of topically used antimicrobials through *Staphylococcus aureus* biofilms: A comparative study using different models. *J. Drug Deliv. Sci. Technol.* 48, 429-436 (2018).

Aljamali, N. M., Salih, N. S., 2015. Primary identification of unknowns via reagents. Int. Technol. Innov. Res. J. 1, 1-11.

Allen, H. B. et al. The presence and impact of biofilm-producing staphylococci in atopic dermatitis. *JAMA Dermatology* 150, 260-265 (2014).

Alves, M. J. et al. Antimicrobial activity of phenolic compounds identified in wild mushrooms, SAR analysis and docking studies. *J. Appl. Microbiol.* 115, 346-357 (2013).

Amabye, T. G., 2015. Evaluation of Phytochemical, Chemical Composition, Antioxidant and Antimicrobial Screening Parameters of *Rhamnus prinoides* (Gesho) Available in the Market of Mekelle, Tigray, Ethiopia. Nat. Prod. Chem. Res. Amabye 4, 1-6. doi: 10.4172/2329-6836.1000198

Anderl, J. N., Franklin, M. J. & Stewart, P. S. Role of Antibiotic Penetration Limitation in *Klebsiella pneumoniae* biofilm resistance to ampicillin and ciprofloxacin. *Antimicrob. Agents Chemother.* 44, 1818-1824 (2000).

Araniti, F., Sunseri, F., Abenavoli, M. R., 2014. Phytotoxic Activity and Phytochemical Characterization of *Lotus ornithopodioides* L., a Spontaneous Species of Mediterranean Area. Phytochem. Lett. 8, 179-183. doi: 10.1016/j.phytol.2013.08.019

Archer, N. K., Mazaitis, M. J., William Costerton, J., Leid, J. G., Powers, M. E., Shirtliff, M. E., 2011. *Staphylococcus aureus* biofilms: properties, regulation and roles in human disease. Virulence 2, 445-459.

Ashenafi, M., 2006. Review Article: A Review on the Microbiology of Indigenous Fermented Foods and Beverages of Ethiopia. *Ethiop. J. Biol. Sci.* 5, 189-245. doi: 10.4314/ejbs.v512.39036

Bassler, B., 2002. Small talk: Cell-to-Cell Communication in Bacteria. Cell 109, 421-424. doi: 10.1016/S0092-8674 (02) 00749-3

Berhanu, A., 2014. Microbial Profile of Tella and the Role of Gesho (*Rhamnus prinoides*) as Bittering and Antimicrobial Agent in Traditional Tella (beer) Production. Int. Food Res. J. 21, 357-365.

Bjarnsholt, T. (2013). The role of bacterial biofilms in chronic infections. *APMIS.Supplementum*, (136): 1-51 (136), 1-51.

Blankenship, J. R., & Mitchell, A. P. (2006). How to build a biofilm: a fungal perspective. *Current Opinion in Microbiology*, 9 (6), 588-594.

Choundhary, S., 2016. Biochemical tests of different food products used frequently by the human population.

Ciccio, P. Di et al. Biofilm formation by *Staphylococcus aureus* on food contact surfaces: Relationship with temperature and cell surface hydrophobicity. *Food Control* 50, 930-936 (2015).

Costerton, J. W., 1999. Bacterial biofilms: a common cause of persistent infections. Science (80-.). 284, 1318-1322.

Cueva, C. et al. Antimicrobial activity of phenolic acids against commensal, probiotic and pathogenic bacteria. *Res. Microbiol.* 161, 372-382 (2010).

de Oliveira, J. R., de Jesus, D., Figueira, L. W., de Oliveira, F. E., Pacheco Soares, C., Camargo, S. E. A., . . . de Oliveira, L. D. (2017). Biological activities of *Rosmarinus officinalis* L. (rosemary) extract as analyzed in microorganisms and cells. *Experimental Biology and Medicine*, 242 (6), 625-634.

Donlan, R. M. (2002). Biofilms: microbial life on surfaces. Emerg Infect Diseases. 8 (9), 881-890.

Donlan, R., 2001a. Biofilms and device-associated infections. Emerg. Infect. Dis. 7, 277-281.

Donlan, R., 2001b. Biofilm formation: a clinically relevant microbiological process. *Clin. Infect. Dis.* 33, 1387-1392.

Doron, S., Friedman, M., Falach, M., Sadovnic, E., Zvia, H., 2001. Antibacterial effect of parabens against planktonic and biofilm *Streptococcus sobrinus*. *Int. J. Antimicrob. Agents* 18, 575-578.

Everette, J., Bryant, Q., Green, A., Abbey, Y., Wangila, G., Walker, R., 2010. A thorough study of reactivity of various compound classes towards the Folin-Ciocalteu reagent. J. Agric. Food Chem. 58, 8139-8144.

Falsetta, M. L., Klein, M. I., Colonne, P. M., Scott-Anne, K., Gregoire, S., Pai, C. H., . . . . Koo, H. (2014). Symbiotic relationship between *Streptococcus mutans* and *Candida albicans* synergizes virulence of plaque biofilms in vivo. *Infection and Immunity*, 82 (5), 1968-1981.

Fernandes, T., Bhavsar, C., Sawarkar, S., & D'souza, A. (2018). Current and novel approaches for control of dental biofilm. *International Journal of Pharmaceutics*, 536 (1), 199-210.

Fisher, R. A., Gollan, B. & Helaine, S. Persistent bacterial infections and persister cells. *Nat. Rev. Microbiol.* 15, 453-464 (2017).

Fux, C. A., Costerton, J. W., Stewart, P. S., & Stoodley, P. (2005). Survival strategies of infectious biofilms. *Trends in Microbiology*, 13 (1), 34-40.

Gill, E. E., Franco, O. L. & Hancock, R. E. W. Antibiotic adjuvants: diverse strategies for controlling drug-resistant pathogens. *Chem. Biol. Drug Des.* 85, 56-78 (2015).

Hailemariam, A. G., 2017. Chemical characterization and estimation of cheka: a traditional food and drink. Am. J. Appl. Chem. 5, 73-83.

Hamon, M. A., Lazazzera, B. A., 2001. The Sporulation Transcription Factor Spo0A is Required for Biofilm Development in *Bacillus subtilis*. *Mol. Microbiol.* 42, 1199-1209. doi: 10.1046/j.1365-2958.2001.02709.x Harriott, M. M., & Noverr, M. C. (2011). Importance of *Candida*-bacterial polymicrobial biofilms in disease. *Trends in Microbiology*, 19 (11), 557-563.

He, J., Kim, D., Zhou, X., Ahn, S. J., Burne, R. A., Richards, V. P., & Koo, H. (2017). RNA-seq reveals enhanced sugar metabolism in *Streptococcus mutans* co-cultured with *Candida albicans* within mixed-species biofilms. Frontiers in Microbiology, 8 (JUN), 1-15.

Hobby, G. H., Quave, C. L., Nelson, K., Compadre, C. M., Karen, E., Smeltzer, M. S., 2012. *Quercus cerris* extracts limit *Staphylococcus aureus* Biofilm Formation. J. Ethnopharmacol. 144, 812-815. doi: 10.1016/j.jep.2012.10.042.

Høiby, N., Ciofu, O., Johansen, H. K., Song, Z., Moser, C., Jensen, P. Ø., . . . . Bjarnsholt, T. (2011). The clinical impact of bacterial biofilms. *International Journal of Oral Science*, 3 (2), 55-65.

James, G. A., Swogger, E., Wolcott, R., Pulcini, E. deLancey, Secor, P., Sestrich, J., Costerton, J. W., Stewart, P. S., 2008. Biofilms in Chronic Wounds. Wound Repair Regen. 16, 37-44. doi: 10.1111/j.1524-475X.2007.00321.x Karygianni, L., Al-Ahmad, A., Argyropoulou, A., Hellwig, E., Anderson, A. C., & Skaltsounis, A. L. (2016). Natural antimicrobials and oral microorganisms: A systematic review on herbal interventions for the eradication of multispecies oral biofilms. *Frontiers in Microbiology*, 6 (JAN), 1-17.

Kim, D., Sengupta, A., Niepa, T. H. R., Lee, B. H., Weljie, A., Freitas-Blanco, V. S., . . . . Koo, H. (2017). *Candida albicans* stimulates *Streptococcus mutans* microcolony development via cross-kingdom biofilm-derived metabolites. *Scientific Reports*, 7 (December 2016), 1-14.

Kiran, M. D. et al. Discovery of a Quorum-Sensing Inhibitor of Drug-Resistant Staphylococcal Infections by Structure-Based Virtual Screening. *Mol. Pharmacol.* 73, 1578-1586 (2008).

Kiran, M. D., Giacometti, A., Cirioni, O. & Balaban, N. Suppression of biofilm related, device-associated infections by staphylococcal Quorum sensing inhibitors Suppression of biofilm related, device-associated infections by staphylococcal quorum sensing inhibitors. *Int. J. Articicial Organs* 31, 761-770 (2008).

Kiringe, J., 2006. A Survey of Traditional Health Remedies Used by the Maasai of Southern Kaijiado District, Kenya. Ethnobot. Res. Appl. 4, 61-73.

Klein, M. I., Xiao, J., Lu, B., Delahunty, C. M., Yates, J. R., & Koo, H. (2012). *Streptococcus mutans* Protein Synthesis during Mixed-Species Biofilm Development by High-Throughput Quantitative Proteomics. *PLOS ONE*, 7 (9).

Kong, K. F., Vuong, C., Otto, M., 2006. *Staphylococcus* Quorum Sensing in Biofilm Formation and Infection. Int. J. Med. Microbiol. 296, 133-139. doi: 10.1016/j.ijmm.2006.01.042

Kumar, G., Jalaluddin, M., Rout, P., Mohanty, R., & Dileep, C. L. (2013). Emerging trends of herbal care in dentistry. Journal of Clinical and Diagnostic Research, 7 (8), 1827-1829.

Kunze, B., Reck, M., Dötsch, A., Lemme, A., Schummer, D., Irschik, H., Steinmetz, H., Wagner-Döbler, I., 2010. Damage of *Streptococcus mutans* biofilms by carolacton, a secondary metabolite from the myxobacterium *Sorangium cellulosum*. BMC Microbiol. 10.

Lee, K., Lee, J. H., Kim, S. Il, Cho, M. H. & Lee, J. Anti-biofilm, anti-hemolysis, and anti-virulence activities of black pepper, cananga, myrrh oils, and nerolidol against *Staphylococcus aureus*. *Appl. Microbiol. Biotechnol.* 98, 9447-9457 (2014).

Lee, M., Regu, M., Seleshe, S., 2015. Uniqueness of Ethiopian traditional alcoholic beverage of plant origin, tella. J. Ethn. Foods 2, 110-114.

Lew, D. & Waldvogel, F. Osteomyelitis. *Lancet* 364, 369-379 (2004).

Little, J. L., 2014. Artifacts in Trimethylsilyl Derivatization Reactions and Ways to Avoid Them, Journal of Chromatography.

Liu, Y., Ren, Z., Hwang, G., & Koo, H. (2018). Therapeutic Strategies Targeting Cariogenic Biofilm Microenvironment. *Advances in Dental Research*, 29 (1), 86-92.

Ma, Y., Marquis, R. E., 1996. Irreversible paraben inhibition of glycolysis by *Streptococcus mutans* GS-5. *Lett. Appl. Microbiol.* 23, 329-333.

Madrera, R. R., Bedriñana, R. P., Valles, B. S., 2015. Production and Characterization of Aroma Compounds from Apple Pomace by Solid-State Fermentation with Selected Yeasts. LWT-Food Sci. Technol. 64, 1342-1353. doi: 10.1016/j.lwt.2015.07.056

Marsh, P. D., 2006. Dental Plaque as a biofilm and a microbial community-implications for health and disease. BMC Oral Health 6, 1-7.

Mattos-graner, R. O., Napimoga, M. H., Duncan, M. J., Smith, D. J., & Fukushima, K. (2004). Comparative Analysis of Gtf Isozyme Production and Diversity in Isolates of *Streptococcus mutans* with Different Biofilm Growth Phenotypes Comparative Analysis of Gtf Isozyme Production and Diversity in Isolates of *Streptococcus mutans* with Different Biofi, 42 (10), 4586-4592.

Maura, D., Ballok, A. & Laurence, R. Considerations and caveats in anti-virulence drug development. *Curr. Opin. Microbiol.* 33, 41-46 (2016).

Merck, E., 1980. Dyeing reagents for thin-layer and paper chromatography, Amines Amino acids Amino acids. Darmstadt.

Molla, Y., 2015. Evaluation of the Antibacterial Activity of the Solvent Fractions of the Leaves of *Rhamnus prinoides* L'Herit (Rhamnaceae).

Molla, Y., Nedi, T., Tadesse, G., Alemayehu, H., & Shibeshi, W. (2016). Evaluation of the in vitro antibacterial activity of the solvent fractions of the leaves of *Rhamnus prinoides* L'Herit (Rhamnaceae) against pathogenic bacteria. BMC Complementary and Alternative Medicine, 16 (1), 1-9.

Mulaw, G., Tesfaye, A., 2017. Technology and microbiology of traditionally fermented food and beverage products of Ethiopia: A review. African J. Microbiol. Res. 11, 825-844.

Muregi, F. W., Chhabra, S. C., Njagi, E. N. M., Lang'at-Thoruwa, C. C., Njue, W. M., Orago, A. S. S., Omar, S. A., Ndiege, I. O., 2003. In vitro Antiplasmodial Activity of Some Plants Used in Kisii, Kenya Against Malaria and their Chloroquine Potentiation Effects. J. Ethnopharmacol. 84, 235-239.

Muregi, F. W., Ishih, A., Miyase, T., Suzuki, T., Kino, H., Amano, T., Mkoji, G. M., Terada, M., 2007. Antimalarial Activity of Methanolic Extracts from Plants Used in Kenyan Ethnomedicine and their Interactions with Chloroquine (CQ) Against a CQ-Tolerant Rodent Parasite, in Mice. J. Ethnopharmacol. 111, 190-195. doi: 10.1016/j.jep.2006.11.009

Muregi, F. W., Ishih, A., Suzuki, T., Kino, H., Amano, T., Mkoji, G. M., Miyase, T., Terada, M., 2007. In Vivo Antimalarial Activity of Aqueous Extracts from Kenyan Medicinal Plants and their Chloroquine (CQ) Potentiation Effects Against a Blood-Induced CQ-Resistant Rodent Parasite in Mice. Phyther. Res. 21, 337-343. doi: 10.1002/ptr Nindi, M. M., Kgarebe, B. V., Wolfender, J. L., Abegaz, B. M., 1999. Electrospray liquid chromatography-mass spectrometry of the leaf extract of *Rhamnus prinoides*. Phytochem. Anal. 69-75.

Niu, C., Robbins, C. M., Pittman, K. J., Osborn, jo D. L., Stubblefield, B. A., Simmons, R. B., & Gilbert, E. S. (2013). LuxS influences *Escherichia coli* biofilm formation through autoinducer-2-dependent and autoinducer-2-independent modalities. *FEMS Microbiology Ecology*, 83 (3), 778-791.

Njoroge, G. N., Bussmann, R. W., 2006. Traditional Management of Ear, Nose and Throat (ENT) Diseases in Central Kenya. J. Ethnobiol. Ethnomed. 2, 1-9. doi: 10.1186/1746-4269-2-54

Nobile, C. J., & Johnson, A. D. (2016). *Candida albicans* Biofilm and Human Disease. *HHS Public Access*, 71-92.

O'Connell, H. A., Kottkamp, G. S., Eppelbaum, J. L., Stubblefield, B. A., Gilbert, S. E., & Gilbert, E. S. (2006). Influences of biofilm structure and antibiotic resistance mechanisms on indirect pathogenicity in a model polymicrobial biofilm. *Applied and Environmental Microbiology*, 72 (7), 5013-5019.

O'Toole, G. A. *Microtiter dish biofilm formation assay. Journal of Visualized Experiments* 10-11 (2011). doi: 10.3791/2437

Olsen, I. Biofilm-specific Antibiotic Tolerance and Resistance. *Eur. J. Clin. Microbiol. Infect. Dis.* 34, 877-886 (2015).

Palombo, E. A. (2011). Traditional medicinal plant extracts and natural products with activity against oral bacteria: Potential application in the prevention and treatment of oral diseases. *Evidence-Based Complementary and Alternative Medicine*, 2011.

Pereira-Cenci, T., Deng, D. M., Kraneveld, E. A., Manders, E. M. M., Del Bel Cury, A. A., ten Cate, J. M., & Crielaard, W. (2008). The effect of *Streptococcus mutans* and *Candida glabrata* on *Candida albicans* biofilms formed on different surfaces. *Archives of Oral Biology*, 53 (8), 755-764.

Peters, B. M., Jabra-rizk, M. A., Costerton, J. W., & Shirtliff, M. E. (2012). Polymicrobial Interactions: Impact on Pathogenesis and Human Disease, 193-213.

Peterson, C. J., Cosse, A., Coats, J. R., 2000. Insecticidal Components in the Meal of *Crambe abyssinica*. J. Agric. Urban Entomol. 17, 27-35.

Quave, C. L., Plano, L. R. W., Pantuso, T., Bennett, B. C., 2008. Effects of extracts from Italian medicinal plants on planktonic growth, biofilm formation and adherence of methicillin-resistant *Staphylococcus aureus*. NIH 118, 418-428.

Roder, B. et al. Clinical features of *Staphylococcus aureus* endocarditis. *Arch Intern Med* 159, 462-469 (1999).

Roy, R., Tiwari, M., Donelli, G., & Tiwari, V. (2017). Strategies for combating bacterial biofilms: A focus on anti-biofilm agents and their mechanisms of action. *Virulence*, 9 (1), 00-00.

Sahile, S., 1990. The Microbiology of Tella Fermentation.

Sanchez, C. J., Mende, K., Beckius, M. L., Kevin, A., Desiree, R. R., Joseph, W. C., Clinton, M. K., 2013. Biofilm formation by clinical isolates and the implications in chronic infections. *BMC Infect. Dis.* 13, 1-12.

Santiago, A., Ahmed, M., Wang, S., Damera, K., Tai, P. C., Gilbert, E., Derby, C. D., 2016. Inhibition and dispersal of *Pseudomonas aeruginosa* biofilms by combination treatment with escapin intermediate products and hydrogen peroxide. Antimicrob. Agents Chemother. 60, 5554-5562.

Savage, V. J., Chopra, I. & O'Neill, A. J. *Staphylococcus aureus* Biofilms Promote Horizontal Transfer of Antibiotic Resistance. *Antimicrob. Agents Chemother.* 57, 1968-1970 (2013).

Savini, V., Catavitello, C., Astolfi, D., Balbinot, A., Masciarelli, G., Pompilio, A., . . . . Iacone, A. (2010). Bacterial contamination of platelets and septic transfusions: review of the literature and discussion on recent patents about biofilm treatment. *Recent Pat Antiinfect Drug Discov,* 5 (2), 168-176.

Schierle, C. F., De la Garza, M., Mustoe, T. A., Galiano, R., 2009. Staphylococcal Biofilms Impair Wound Healing by Delaying Reepithelialization in a Murine Cutaneous Wound Model. Wound Repair Regen. 17, 354-359. doi: 10.1111/j.1524-475X.2009.00489.x Singh, R., Ray, P., Das, A. & Sharma, M. Penetration of antibiotics through *Staphylococcus aureus* and *Staphylococcus epidermidis* biofilms. *J. Antimicrob. Chemother.* 65, 1955-1958 (2010).

Somchit, M. N., Reezal, I., Elysha Nur, I., Mutalib, A. R., 2003. In vitro antimicrobial activity of ethanol and water extracts of *Cassia alata*. J. Ethnopharmacol. 84, 1-4.

Spoering, A. & Lewis, K. Biofilms and planktonic cells in *Pseufdomonas aeruginosa* have similar resistance to killing by antimicrobials. *J. Bacteriol.* 183, 6746-6751 (2001).

Stacy, A., McNally, L., Darch, S. E., Brown, S. P., & Whiteley, M. (2016). The biogeography of polymicrobial infection. *Nature Reviews Microbiology*, 14 (2), 93-105.

Stalder, T. & Top, E. Plasmid transfer in bifilms: a perspective on limitations and opportunities. *Biofilms and Microbiomes* 51, 1625-1627 (2016).

Stepanovic, S., Vukovic, D., Hola, V., Bonaventura, G. Di, Djukic', S., Irkovic', I. C., Ruzicka, F., 2007. Quantification of biofilm in microtiter plates: overview of testing conditions and practical recommendations for assessment of biofilm production by staphylococci. Apmis 115, 891-899.

Stewart, P. S., & William Costerton, J. (2001). Antibiotic resistance of bacteria in biofilms. *The Lancet,* 358 (9276), 135-138.

Sushma, J., Raju, D. P., B, M., Priya, U., Sam, P., 2016. Phytochemical screening and in vitro antioxidant activity of Bacopa monniera stabilized silver and gold nanoparticles. Int. J. Res. Eng. Appl. Sci. 6, 24-34.

Teklehaymanot, T., Giday, M., 2007. Ethnobotanical Study of Medicinal Plants Used by People in Zegie Peninsula, Northwestern Ethiopia. J. Ethnobiol. Ethnomed. 3, 1-11. doi: 10.1186/1746-4269-3-12

Wolcott, R., Costerton, J. W., Raoult, D., & Cutler, S. J. (2013). The polymicrobial nature of biofilm infection. *Clinical Microbiology and Infection*, 19 (2), 107-112.

Woo, S.-G., Lee, S.-M., Lee, S.-Y., Lim, K.-H., Ha, E.-J., Kim, S.-H., Eom, Y.-B., 2017. The Effectiveness of Antibiofilm and Anti-virulence Properties of Dihydrocelastrol and Dihydrocelastryl diacetate in Fighting Against Methicillin-resistant *Staphylococcus aureus*. Arch. Microbiol. 199, 1151-1163. doi: 10.1007/s00203-017-1386-x Wright, G. Antibiotic adjuvants: rescuing antibiotics from resistance. *Trends Microbiol.* 24, 862-871 (2016).

Zhang, J., Biggs, I., Sirdaarta, J., White, A., Edwin Cock, I., 2016. Antibacterial and Anticancer Properties of *Boswellia carteri* Birdw. and *Commiphora molmol* Engl. Oleo-Resin Solvent Extractions. Pharmacogn. Commun. 6, 120-136. doi: 10.5530/pc.2016.3.2

Zhang, J., Rui, X., Wang, L., Guan, Y., Sun, X., Dong, M., 2014. Polyphenolic extract from *Rosa rugosa* tea inhibits bacterial quorum sensing and biofilm formation. Food Control 42, 125-131.

What is claimed is:

1. A method of inhibiting biofilm formation on a surface comprising contacting a surface susceptible to biofilm formation with a composition consisting of 4-hydroxy-4-methylpentanone (HMP) and a pharmaceutically acceptable carrier or a composition consisting of a pharmaceutically acceptable carrier, HMP, and at least one small molecule selected from the group consisting of: an extract of *Rhamnus prinoides* (gesho), 4-ethoxy benzoic acid (4EB), ethyl 4-ethoxybenzoate (EEB), methyl gallate, methyl paraben, adipic acid, phytol, or phytol acetate; and wherein the biofilm is not caused by *Staphylococcus aureus*.

2. The method of claim 1, wherein the surface is in a subject and the method comprises administering to the subject a composition comprising a therapeutically effective amount of a composition comprising 4-hydroxy-4-methylpentanone (HMP).

3. The method of claim 1, wherein the surface is selected from the group consisting of: a medical instrument, artificial joint, artificial heart valve, venous catheter, urinary catheter, ventilator, food handling, water handling, pipes, tooth, oral cavity, denture, body, wound, rash, abrasion, cut, surgical incision, implant, and nose.

4. The method of claim 1, wherein the biofilm is caused by a prokaryotic organism.

5. The method of claim 4, wherein the prokaryotic organism is a Gram positive organism.

6. The method of claim 5, wherein the Gram positive organism comprises *Streptococcus mutans*, or *Bacillus subtilis*.

7. The method of claim 4, wherein the prokaryotic organism is a Gram negative organism.

8. The method of claim 7, wherein the Gram negative organism comprises *Pseudomonas aeruginosa*.

9. The method of claim 8, which further comprises contacting the surface with a composition comprising vancomycin.

10. The method of claim 1, wherein the biofilm is caused by a eukaryotic organism.

11. The method of claim 10, wherein the eukaryotic organism comprises *Candida albicans*.

12. The method of claim 1, wherein the biofilm is caused by prokaryotic organism and a eukaryotic organism.

13. The method of claim 1, wherein the method inhibits one or more virulence factors.

14. A method of enhancing the sensitivity of a biofilm to an antibiotic comprising contacting the biofilm with a composition consisting of 4-hydroxy-4-methylpentanone (HMP) and a pharmaceutically acceptable carrier.

15. A method of claim 14, further comprising contacting the biofilm with a composition comprising an antibiotic.

16. A composition useful for biofilm inhibition, consisting of 4-hydroxy-4-methylpentanone (HMP) and a pharmaceutically acceptable carrier.

17. A composition of claim 16, which further comprises an antibiotic.

18. A composition of claim 17, wherein the antibiotic is vancomycin.

19. A composition of claim 16, wherein the composition is selected from the group consisting of: surface cleaner, disinfectant, sanitizer, mouth rinse paint, caulk, adhesive, shampoo, body wash, medicated sponges, scaffolds, stents, matrixes, grafts, bandages, adhesive bandages, wound dressings, surgical drapes, sutures, staples, surgical adhesives, salves, creams, wound adhesives, and pharmaceutical composition.

20. The composition of claim 16, further comprising an isolated small molecule derivative comprising at least one composition selected from the group consisting of: an extract of *Rhamnus prinoides* (gesho), 4-ethoxy benzoic acid (4EB), ethyl 4-ethoxybenzoate (EEB), methyl gallate, methyl paraben, adipic acid, phytol, or phytol acetate.

21. A method of inhibiting biofilm formation in a subject comprising administering to the subject the composition of claim 16 and inhibiting biofilm formation in the subject.

22. The method of claim 21, wherein the subject has at least one biofilm-associated disease selected from the group consisting of: tooth decay, cystic fibrosis, pneumonia, device associated infection, and chronic wound infections.

23. A method of inhibiting biofilm formation on a surface comprising contacting a surface susceptible to biofilm formation with a composition consisting of 4-hydroxy-4-methylpentanone (HMP) or a composition comprising HMP and at least one small molecule selected from the group consisting of: an extract of *Rhamnus prinoides* (gesho), 4-ethoxy benzoic acid (4EB), ethyl 4-ethoxybenzoate (EEB), methyl gallate, methyl paraben, adipic acid, phytol, or phytol acetate; wherein the biofilm is not caused by *Staphylococcus aureus*; and wherein the composition does not further include one or more active ingredients such as antimicrobial agents, anti-inflammatory agents, or anesthetics.

* * * * *